United States Patent
Chan

(10) Patent No.: US 6,995,283 B2
(45) Date of Patent: Feb. 7, 2006

(54) BENZOPHENONES AS INHIBITORS OF REVERSE TRANSCRIPTASE

(75) Inventor: Joseph Howing Chan, Durham, NC (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 10/469,104

(22) PCT Filed: Feb. 28, 2002

(86) PCT No.: PCT/US02/06037

§ 371 (c)(1),
(2), (4) Date: Feb. 5, 2004

(87) PCT Pub. No.: WO02/070470

PCT Pub. Date: Sep. 12, 2002

(65) Prior Publication Data

US 2004/0122064 A1 Jun. 24, 2004

Related U.S. Application Data

(60) Provisional application No. 60/272,953, filed on Mar. 2, 2001.

(51) Int. Cl.
C07C 311/16 (2006.01)
C07C 231/02 (2006.01)
A61K 31/18 (2006.01)

(52) U.S. Cl. ........................ 564/86; 514/238.2; 514/317; 514/408; 514/413; 514/423; 514/483; 514/522; 514/603; 544/160; 546/230; 548/537; 548/567; 560/13; 558/413

(58) Field of Classification Search .............. 514/238.2, 514/317, 408, 413, 423, 483, 522, 603; 544/160; 546/230; 548/537, 567; 560/13; 558/413; 564/138, 86
See application file for complete search history.

(56) References Cited

FOREIGN PATENT DOCUMENTS

JP 03198050 * 8/1991

OTHER PUBLICATIONS

Wyatt, PG, et al. "Benzophenone Derivatives: A Novel Series of Potent and Selective Inhibitors of Human Immunodeficiency Virus Type 1 Reverse Transcriptase." Journal of Medicinal Chemistry, vol. 38, No. 10, 1995, pp. 1657–1665.

* cited by examiner

Primary Examiner—Shailendra Kumar
(74) Attorney, Agent, or Firm—Kimberly H. Parker

(57) ABSTRACT

The present invention is directed to beazophenone compounds useful in the inhibition of HIV reverse transcriptase, particularly its resistant varieties.

33 Claims, 1 Drawing Sheet

BENZOPHENONES AS INHIBITORS OF REVERSE TRANSCRIPTASE

This application is filed pursuant to 35 U.S.C. §371 as a United States National Phase Application of International Application No. PCT/US02/06037 filed Feb. 28, 2002 which claims priority from U.S. 60/272,953 filed Mar. 2, 2001 in the United States.

BACKGROUND OF THE INVENTION

The human immunodeficiency virus ("HIV") is the causative agent for acquired immunodeficiency syndrome ("AIDS"), a disease characterized by the destruction of the immune system, particularly of CD4$^+$ T-cells, with attendant susceptibility to opportunistic infections, and its precursor AIDS-related complex ("ARC"), a syndrome characterized by symptoms such as persistent generalized lymphadenopathy, fever and weight loss. HIV is a retrovirus; the conversion of its RNA to DNA is accomplished through the action of the enzyme reverse transcriptase. Compounds that inhibit the function of reverse transcriptase inhibit replication of HIV in infected cells. Such compounds are useful in the prevention or treatment of HIV infection in humans.

Non-nucleoside reverse transcriptase inhibitors (NNRTIs), in addition to the nucleoside reverse transcriptase inhibitors gained a definitive place in the treatment of HIV-1 infections. The NNRTIs interact with a specific site of HIV-1 reverse transcriptase that is closely associated with, but distinct from, the nucleoside binding site on reverse transcriptase. NNRTIs, however, are notorious for rapidly eliciting resistance due to mutations of the amino acids surrounding the NNRTI-binding site (E. De Clercq, *Il Famaco* 54, 26–45, 1999). Failure of long-term efficacy of NNRTIs is often associated with the emergence of drug-resistant virus strains (J. Balzarini, *Biochemical Pharmacology*, Vol 58, 1–27, 1999). Moreover, the mutations that appear in the reverse transcriptase enzyme frequently result in a decreased sensitivity to other reverse transcriptase inhibitors, which results in cross-resistance.

JP 59181246 disclosed certain benzopbenones useful as anticancer agents. Certain benzophenone derivatives as inhibitors of HIV-1 reverse transriptase were disclosed in Wyatt et al. (J. Med. Chem. 38:1657–1665, 1995). However, these compounds were primarily active against wild-type HIV-1 reverse transcriptase, rapidly induced resistant virus, and were inactive against a common resistant strain. Benzophenone compounds disclosed in WO 01/17982 exhibit activity against both wild-type and mutant HIV, but have limited aqueous solubility and oral bioavailibilty.

We have now discovered a series of benzophenone derivatives that when administered in vivo provide compounds that are useful as inhibitors of both wild type and mutant variants of HIV reverse transcriptase. In addition, the compounds of the present invention have certain pharmaceutic and pharmacokinetic properties that render them advantageous as therapeutic agents.

BRIEF DESCRIPTIONS OF THE INVENTION

A first aspect of the invention features compounds of formulas IA, IA', and IB (hereinafter known as compounds of formula I). These compounds are useful as prodrugs that, when administered in vivo, provide compounds that are useful in the inhibition of HIV reverse transcriptase, particularly its resistant varieties, the prevention of infection by HIV, the treatment of infection by HIV and in the treatment of AIDS and/or ARC, either as pharmaceutically acceptable salts or pharmaceutical composition ingredients. A second aspect of the invention features methods of treating AIDS, methods of preventing infection by HIV, and methods of treating infection by HIV as monotherapy or in combination with other antivirals, anti-infectives, immunomodulators, antibiotics or vaccines. A third aspect of the invention features pharmaceutical compositions comprising the above-mentioned compounds and which are suitable for the prevention or treatment of HIV infection. A fourth aspect of the invention features processes for making the above-mentioned compounds.

DETAILED DESCRIPTION OF THE INVENTION

Figure 1:
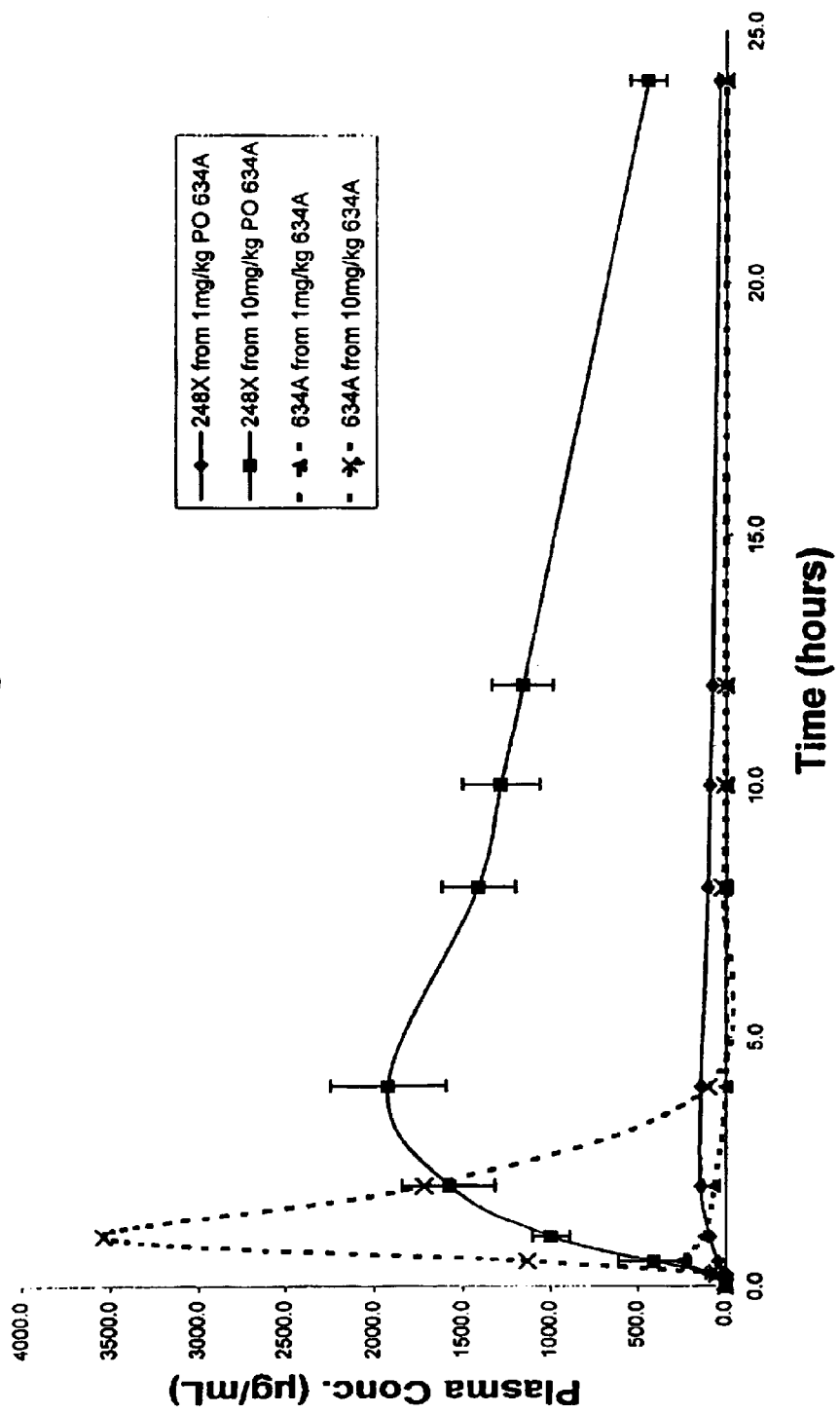
FIG. 1: Plasma concentrations ($\mu$g/mL) of compounds 34 (634A) and 40 (248X) following administration of 1 and 10 mg/kg oral (solution) doses of compound 34 to male beagle dog.

The present invention relates to compounds of formula I, or pharmaceutically acceptable salts thereof, in the inhibition of HIV reverse transcriptase and its resistant varieties, the prevention or treatment of infection by HIV and in the treatment of the resulting acquired immune deficiency syndrome (AIDS).

The present invention features compounds of formula (IA)

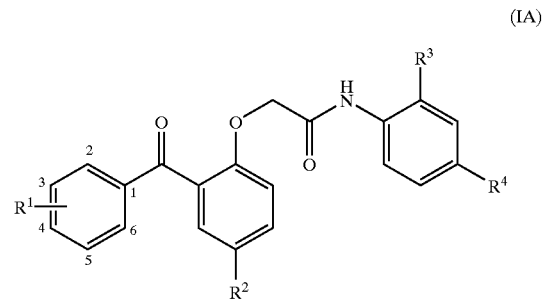

(IA)

wherein:
$R^1$ is one or more substituents independently selected from the group consisting of halogen, —$CF_3$, $C_{1-8}$alkyl, amino$C_{1-8}$alkyl, alkoxy, —CN, —$NO_2$, —$NH_2$, —$SR^8$, —$S(O)R^8$, —$S(O)_2R^8$, —$C(O)R^8$; $C_{2-6}$alkenyl which may be optionally substituted with a substituent selected from the group consisting of hydroxy, halogen, $C_{3-6}$cycloalkyl, $C_{6-14}$aryl and heterocycle; $C_{2-6}$alkynyl which may be optionally substituted with a substituent selected from the group consisting of hydroxy, halogen, $C_{6-14}$aryl, $C_{3-6}$cycloalkyl, and heterocycle; and heterocycle, optionally substituted with one or more substituents selected from the group consisting of halogen, $C_{1-8}$alkyl, —CN, $C_{1-8}$alkyl$C_{6-14}$aryl and heterocycle;

$R^2$ is selected from the group consisting of hydrogen, halogen, $C_{1-8}$alkyl, —$NO_2$, —$NH_2$, $C_{1-8}$alkylamino, —$CF_3$ and alkoxy;

$R^3$ is selected from the group consisting of hydroxy, halogen, —$CF_3$, —$NO_2$ and $C_{1-8}$alkyl;

$R^4$ is selected from the group consisting of —$S(O)_2NR^5R^6$, —$S(O)_2N=C(OR^7)_2$ and —$S(O)_2N=CR^7(OR^7)$;

$R^5$ is selected from the group consisting of hydrogen, $C_{6-14}$aryl, $C_{1-8}$alkyl, $C_{3-6}$cycloalkyl$C_{1-8}$alkyl and $C_{3-6}$cycloalkyl;

$R^6$ is selected from the group consisting of —C(O)$R^7$, —C(O)O$R^7$, —C(O)C(O)O$R^7$, —C(O)CH(N$R^{12}R^{13}$)$R^{11}$, alkoxy$C_{1-8}$alkyl and —$CH_2$O—($CH_2CH_2$O)$_n$—$CH_2CH_2OCH_3$, wherein n is 0–4;

$R^7$ is selected from the group consisting of $C_{3-6}$cycloalkyl$C_{1-8}$alkyl, hydroxy$C_{1-8}$alkyl, $C_{6-14}$aryl, heterocycle optionally subsituted with $C_{1-8}$alkyl, $C_{6-14}$aryl$C_{1-8}$alkyl, —($CH_2CH_2$—O)$_n$—$CH_3$, where n=1–4, alkoxy$C_{1-8}$alkyl and $C_{1-8}$alkyl optionally substituted with —O—C(O)$R^{12}$;

$R^8$ is selected from the group consisting of $C_{1-8}$alkyl, $C_{3-6}$cycloalkyl$C_{1-8}$alkyl, $C_{3-6}$cycloalkyl, $C_{6-14}$aryl and heterocycle;

$R^{11}$ is selected from the group consisting of hydrogen,

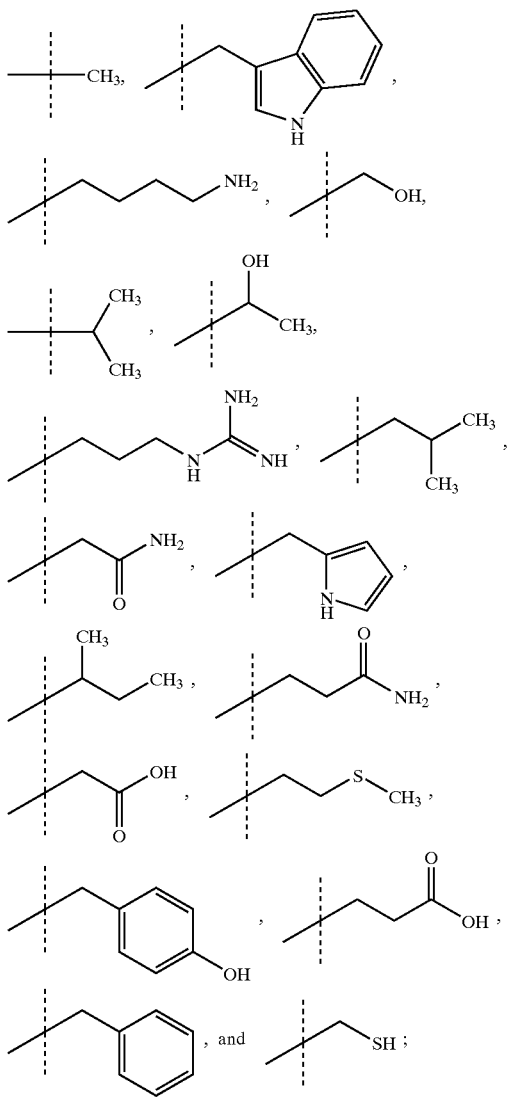

$R^{12}$ and $R^{13}$ are independently selected from the group consisting of hydrogen, $C_{1-8}$alkyl, $C_{3-6}$cycloalkyl and $C_{6-14}$aryl;

or a pharmaceutically acceptable derivative thereof.

The present invention features compounds of formula (IA), wherein $R^1$ is a substituent in either the 3 or 5 position, or both the 3 and 5 positions, independently selected from the group consisting of halogen, —$CF_3$, $C_{1-8}$alkyl, amino$C_{1-8}$alkyl, alkoxy, —CN, —$NO_2$, —$NH_2$, —S$R^8$, —S(O)$R^8$, —S(O)$_2$ $R^8$, —C(O)$R^8$; $C_{2-6}$alkenyl which may be optionally substituted with a substituent selected from the group consisting of hydroxy, halogen, $C_{3-6}$cycloalkyl, $C_{6-14}$aryl and heterocycle; $C_{2-6}$alkynyl which may be optionally substituted with a substituent selected from the group consisting of hydroxy, halogen, $C_{6-14}$aryl, $C_{3-6}$cycloalkyl, and heterocycle; and heterocycle, optionally substituted with one or more substituents selected from the group consisting of halogen, $C_{1-8}$alkyl, —CN, $C_{6-14}$aryl$C_{1-8}$alkyl and heterocycle;

$R^2$ is selected from the group consisting of hydrogen, halogen, $C_{1-8}$alkyl, —$NO_2$, —$NH_2$, $C_{1-8}$alkylamino, —$CF_3$ and alkoxy;

$R^3$ is selected from the group consisting of hydroxy, halogen, —$CF_3$, —$NO_2$ and $C_{1-8}$alkyl;

$R^4$ is selected from the group consisting of —S(O)$_2$N$R^5R^6$, —S(O)$_2$N=C(O$R^7$)$_2$ and —S(O)$_2$N=C$R^7$(O$R^7$);

$R^5$ is selected from the group consisting of hydrogen, $C_{6-14}$aryl, $C_{1-8}$alkyl, $C_{3-6}$cycloalkyl$C_{1-8}$alkyl and $C_{3-6}$cycloalkyl;

$R^6$ is selected from the group consisting of —C(O)$R^7$, —C(O)O$R^7$, —C(O)C(O)O$R^7$, —C(O)CH(N$R^{12}R^{13}$)$R^{11}$, alkoxy$C_{1-8}$alkyl and —$CH_2$O—($CH_2CH_2$O)$_n$—$CH_2CH_2OCH_3$, wherein n is 0–4;

$R^7$ is selected from the group consisting of $C_{3-6}$cycloalkyl$C_{1-8}$alkyl, hydroxy$C_{1-8}$alkyl, $C_{6-14}$aryl, heterocycle optionally subsituted with $C_{1-8}$alkyl, $C_{6-14}$aryl$C_{1-8}$alkyl, —($CH_2CH_2$—O)$_n$—$CH_3$, where n=1–4, alkoxy$C_{1-8}$alkyl and $C_{1-8}$alkyl optionally substituted with —O—C(O)$R^{12}$;

$R^8$ is selected from the group consisting of $C_{1-8}$alkyl, $C_{3-6}$cycloalkyl$C_{1-8}$alkyl, $C_{3-6}$cycloalkyl, $C_{6-14}$aryl and heterocycle;

$R^{11}$ is selected from the group consisting of hydrogen,

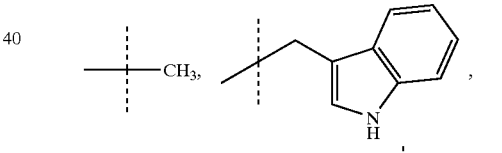

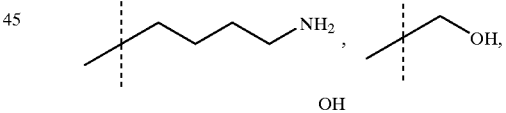

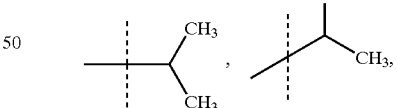

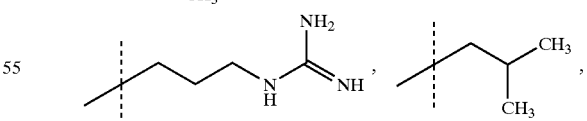

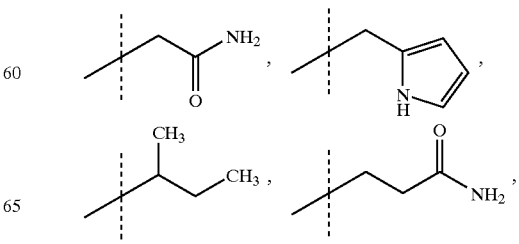

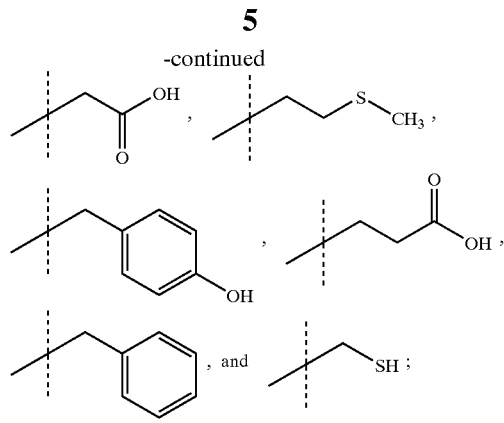

R[12] and R[13] are independently selected from the group consisting of hydrogen, C[1-8]alkyl, C[3-6]cycloalkyl and C[6-14]aryl;

or a pharmaceutically acceptable derivative thereof.

The present invention features compounds of formula (IA), wherein

R[1] is a substituent in the 3 or 5 position, or in both the 3 and 5 positions, independently selected from the group consisting of halogen, C[1-8]alkyl, —CF[3] and —CN;

R[2] is selected from the group consisting of halogen, C[1-8]alkyl, —NO[2], —CF[3] and alkoxy;

R[3] is C[1-8]alkyl;

R[4] is selected from the group consisting of —S(O)[2]NR[5]R[6], —S(O)[2]N=C(OR[7])[2] and —S(O)[2]N=CR[7](OR[7]);

R[5] is selected from the group consisting of hydrogen, C[6-14]aryl, C[1-8]alkyl, C[3-6]cycloalkylC[1-8]cycloalkyl and C[3-6]cycloalkyl;

R[6] is selected from the group consisting of —C(O)R[7], —C(O)OR[7], —C(O)CH(NR[12]R[13])R[11], —C(O)OC(O)OR[7]alkoxyC[1-8]alkyl and —CH[2]O—(CH[2]CH[2]O)[n]—CH[2]CH[2]OCH[3], wherein n is 0–4;

R[7] is selected from the group consisting of C[3-6]cycloalkylC[1-8]alkyl, hydroxyC[1-8]alkyl, C[6-14]aryl, heterocycle optionally subsituted with C[1-8]alkyl, C[6-14]arylC[1-8]alkyl, —(CH[2]CH[2]—O)[n]—CH[3], where n=1–4, alkoxyC[1-8]alkyl and C[1-8]alkyl optionally substituted with —O—C(O)R[12];

R[11] is selected from the group consisting of hydrogen,

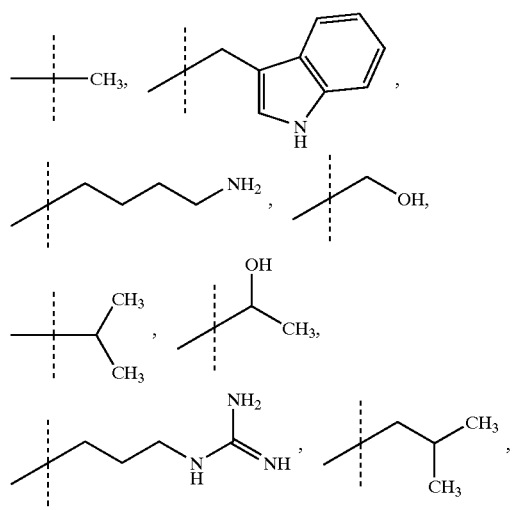

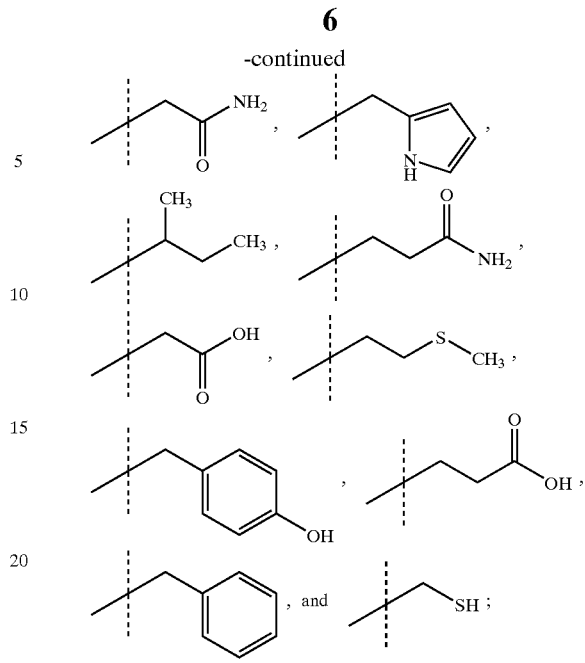

R[12] and R[13] are independently selected from the group consisting of hydrogen, C[1-8]alkyl, C[3-6]cycloalkyl and C[6-14]aryl;

or a pharmaceutically acceptable derivative thereof.

The present invention features compounds of formula (IA), wherein

R[1] is a substituent in the 3 or 5 position, or in both the 3 and 5 positions, independently selected from the group consisting of halogen, C[1-8]alkyl, —CF[3] and —CN;

R[2] is halogen;

R[3] is C[1-8]alkyl;

R[4] is selected from the group consisting of —S(O)[2]NR[5]R[6], —S(O)[2]N=C(OR[7])[2] and —S(O)[2]N=CR[7](OR[7]);

R[5] is selected from the group consisting of hydrogen, C[6-14]aryl, C[1-8]alkyl, C[3-6]cycloalkylC[1-8]alkyl and C[3-6]cycloalkyl;

R[6] is selected from the group consisting of —C(O)R[7], —C(O)OR[7], —C(O)CH(NR[12]R[13])R[11], alkoxyC[1-8]alkyl and —CH[2]O—(CH[2]CH[2]O)[n]—CH[2]CH[2]OCH[3], wherein n is 0–4;

R[7] is selected from the group consisting of C[3-6]cycloalkylC[1-8]alkyl, hydroxyC[1-8]alkyl, C[6-14]aryl, heterocycle optionally subsituted with C[1-8]alkyl, C[6-14]arylC[1-8]alkyl, —(CH[2]CH[2]—O)[n]—CH[3], where n=1–4, alkoxyC[1-8]alkyl and C[1-8] alkyl optionally substituted with —O—C(O)R[12];

R[11] is selected from the group consisting of hydrogen,

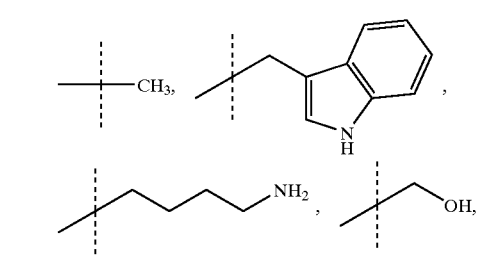

-continued

[chemical structures shown: isobutyl with OH/CH3, guanidinyl propyl, isobutyl-CH3, acetamide, pyrrolylmethyl, isobutyl-CH3, butanamide, carboxymethyl, methylthioethyl, 4-hydroxybenzyl, carboxypropyl, benzyl, and thiol]

, and $R^{12}$ and $R^{13}$ are independently selected from the group consisting of hydrogen, $C_{1-8}$alkyl, $C_{3-6}$cycloalkyl and $C_{6-14}$aryl;

or a pharmaceutically acceptable derivative thereof.

The present invention features compounds of formula (IA), wherein $R^1$ is a substituent in the 3 or 5 position, or in both the 3 and 5 positions, independently selected from the group consisting of halogen, $C_{1-8}$alkyl, —$CF_3$ and —CN;

$R^2$ is halogen;

$R^3$ is $C_{1-8}$alkyl;

$R^4$ is —$S(O)_2NR^5R^6$;

$R^5$ is selected from the group consisting of hydrogen, $C_{1-8}$alkyl, $C_{3-6}$cycloalkylC$_{1-8}$alkyl and $C_{3-6}$cycloalkyl;

$R^6$ is selected from the group consisting of —$C(O)R^7$ and —$C(O)OR^7$;

$R^7$ is selected from the group consisting of $C_{3-6}$cycloalkylC$_{1-8}$alkyl, hydroxyC$_{1-8}$alkyl, —(CH$_2$CH$_2$—O)$_n$—CH$_3$, where n=1–4, alkoxyC$_{1-8}$alkyl and $C_{1-8}$alkyl optionally substituted with —O—$C(O)R^{12}$;

$R^{12}$ is $C_{1-8}$alkyl, $C_{3-6}$cycloalkyl and $C_{6-14}$aryl;

or a pharmaceutically acceptable derivative thereof.

The present invention features compounds of formula (IA), wherein $R^1$ is a substituent in the 3 or 5 position, or in both the 3 and 5 positions, independently selected from the group consisting of halogen, $C_{1-8}$alkyl, —$CF_3$ and —CN;

$R^2$ is halogen;

$R^3$ is $C_{1-8}$alkyl;

$R^4$ is —$S(O)_2NR^5R^6$;

$R^5$ is hydrogen;

$R^6$ is selected from the group consisting of —$C(O)R^7$ and —$C(O)OR^7$;

$R^7$ is $C_{1-8}$alkyl;

or a pharmaceutically acceptable derivative thereof.

The present invention features compounds of formula (IA), wherein $R^1$ is a substituent in both the 3 and 5 positions, independently selected from the group consisting of halogen, $C_{1-8}$alkyl, —$CF_3$ and —CN;

$R^2$ is halogen;

$R^3$ is $C_{1-8}$alkyl;

$R^4$ is —$S(O)_2NR^5R^6$;

$R^5$ is hydrogen;

$R^6$ is selected from the group consisting of —$C(O)R^7$ and —$C(O)OR^7$;

$R^7$ is $C_{1-8}$alkyl;

or a pharmaceutically acceptable derivative thereof.

The present invention features compounds of formula (IA')

(IA')

[chemical structure of formula IA' showing a benzophenone with R$^{1a}$, R$^{1b}$, R$^2$ substituents linked via OCH$_2$C(O)NH to an aniline bearing R$^3$ and SO$_2$NHR$^{14}$]

wherein, $R^{1a}$ and $R^{1b}$ are independently selected from the group consisting of hydrogen, halogen, $C_{1-8}$alkyl, —$CF_3$ and —CN;

$R^2$ is halogen;

$R^3$ is $C_{1-8}$alkyl;

$R^{14}$ is selected from the group consisting of

[chemical structures: methoxymethyl, methoxyethoxyethoxy, acetyl, propanoyl methyl variant, acetyl methyl, isopropyl ester, isobutyryl (methyl branched), 2-methoxyethyl ester, isopentanoyl, methoxyacetyl, and]

-continued

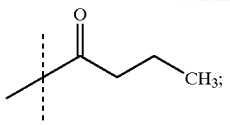

or a pharmaceutically acceptable derivative thereof;
provided that both $R^{1a}$ and $R^{1b}$ are not hydrogen.

The present invention also features compounds of formula IA' wherein
$R^{1a}$ and $R^{1b}$ are independently selected from the group consisting of halogen, —CF$_3$ and —CN;
$R^2$ is halogen;
$R^3$ is C$_{1-8}$alkyl;
$R^{14}$ is selected from the group consisting of

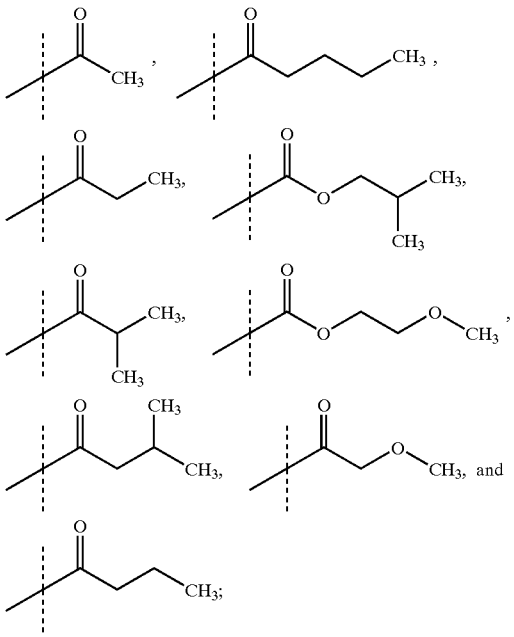

or a pharmaceutically acceptable derivative thereof.

The present invention features compounds of formula (IB), wherein (IB)

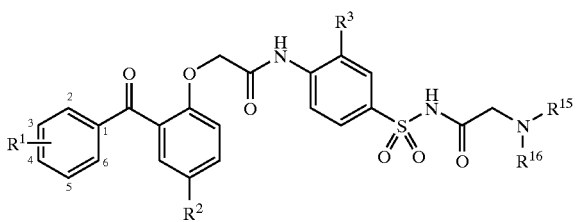

$R^1$ is one or more substituents independently selected from the group consisting of halogen, —CF$_3$, C$_{1-8}$alkyl, aminoC$_{1-8}$alkyl, alkoxy, —CN, —NO$_2$, —NH$_2$, —SR$^8$, —S(O)R$^8$, —S(O)$_2$R$^8$, —C(O)R$^8$; C$_{2-6}$alkenyl which may be optionally substituted with a substituent selected from the group consisting of hydroxy, halogen, C$_{6-14}$aryl, C$_{3-6}$cycloalkyl, C$_{6-14}$aryl and heterocycle; C$_{2-6}$alkynyl which may be optionally substituted with a substituent selected from the group consisting of hydroxy, halogen, C$_{3-6}$cycloakyl, C$_{6-14}$aryl and heterocycle; and heterocycle, optionally substituted with one or more substituents selected from the group consisting of halogen, C$_{1-8}$alkyl, —CN, C$_{1-8}$alkylC$_{6-14}$aryl and heterocycle;
$R^2$ is selected from the group consisting of hydrogen, halogen, C$_{1-8}$alkyl, —NO$_2$, —NH$_2$, C$_{1-8}$alkylamino, —CF$_3$ and alkoxy;
$R^3$ is selected from the group consisting of hydroxy, halogen, —CF$_3$, —NO$_2$ and C$_{1-8}$alkyl;
$R^8$ is selected from the group consisting of C$_{1-8}$alkyl, C$_{3-6}$cycloalkylC$_{1-8}$alkyl, C$_{3-6}$cycloalkyl, C$_{6-14}$aryl and heterocycle;
$R^{15}$ and $R^{16}$ are independently selected from the group consisting of hydrogen, C$_{1-8}$alkyl, C$_{3-6}$cycloalkyl and C$_{6-14}$aryl, or $R^{15}$ and $R^{16}$ together with the atom to which they are attached form a ring, which optionally includes one or more heteroatoms selected from the group consisting of N, O and S, wherein N may be optionally substituted with a substituent selected from the group consisting of hydrogen, C$_{1-8}$alkyl and C$_{6-14}$arylC$_{1-8}$alkyl;
or a pharmaceutically acceptable derivative thereof.

The present invention features compounds of formula (IB), wherein
$R^1$ is a substituent in either the 3 or 5 position, or in both the 3 and 5 positions, independently selected from the group consisting of halogen, —CF$_3$, C$_{1-8}$alkyl, aminoC$_{1-8}$alkyl, alkoxy, —CN, —NO$_2$, —NH$_2$, —SR$^8$, —S(O)R$^8$, —S(O)$_2$ R$^8$, —C(O)R$^8$; C$_{2-6}$alkenyl which may be optionally substituted with a substituent selected from the group consisting of hydroxy, halogen, C$_{3-6}$cycloalkyl, C$_{6-14}$aryl and heterocycle; C$_{2-6}$alkynyl which may be optionally substituted with a substituent selected from the group consisting of hydroxy, halogen, C$_{6-14}$aryl, C$_{3-6}$cycloalkyl, and heterocycle; and heterocycle, optionally substituted with one or more substituents selected from the group consisting of halogen, C$_{1-8}$alkyl, —CN, C$_{1-8}$alkylC$_{6-14}$aryl and heterocycle;
$R^2$ is selected from the group consisting of hydrogen, halogen, C$_{1-8}$alkyl, —NO$_2$, —NH$_2$, C$_{1-8}$alkylamino, —CF$_3$ and alkoxy;
$R^3$ is selected from the group consisting of hydroxy, halogen, —CF$_3$, —NO$_2$ and C$_{1-8}$alkyl;
$R^8$ is selected from the group consisting of C$_{1-8}$alkyl, C$_{3-6}$cycloalkylC$_{1-8}$alkyl, C$_{3-6}$cycloalkyl, C$_{6-14}$aryl and heterocycle;
$R^{15}$ and $R^{16}$ are independently selected from the group consisting of hydrogen, C$_{1-8}$alkyl, C$_{3-6}$cycloalkyl and C$_{6-14}$aryl, or $R^{15}$ and $R^{16}$ together with the atom to which they are attached form a ring, which optionally includes one or more heteroatoms selected from the group consisting of N, O and S, wherein N may be optionally substituted with a substituent selected from the group consisting of hydrogen, C$_{1-8}$alkyl and C$_{6-14}$arylC$_{1-8}$alkyl;
or a pharmaceutically acceptable derivative thereof.

The present invention features compounds of formula (IB), wherein
$R^1$ is a substituent in either the 3 or 5 position, or in both the 3 and 5 positions, independently selected from the group consisting of halogen, C$_{1-8}$alkyl, —CF$_3$ and —CN;
$R^2$ is selected from the group consisting of halogen, C$_{1-8}$alkyl, —NO$_2$, —CF$_3$ and alkoxy;
$R^3$ is C$_{1-8}$alkyl;
$R^{15}$ and $R^{16}$ are independently selected from the group consisting of hydrogen, C$_{1-8}$alkyl, C$_{3-6}$cycloalkyl and C$_{6-14}$aryl, or $R^{15}$ and $R^{16}$ together with the atom to which they are attached form a ring, which optionally includes one or more heteroatoms selected from the group consisting of N, O and S, wherein N may be optionally substituted with a substituent selected from the group consisting of hydrogen, $C_{1-8}$alkyl and $C_{6-14}$aryl$C_{1-8}$alkyl;

or a pharmaceutically acceptable derivative thereof.

The present invention features compounds of formula (IB), wherein $R^1$ is a substituent in either the 3 or 5 position, or both the 3 and 5 positions, independently selected from the group consisting of halogen, $C_{1-8}$alkyl, —$CF_3$ and —CN;

$R^2$ is halogen;

$R^3$ is $C_{1-8}$alkyl;

$R^{15}$ and $R^{16}$ are independently selected from the group consisting of $C_{1-8}$alkyl, $C_{3-6}$cycloalkyl and $C_{6-14}$aryl, or $R^{15}$ and $R^{16}$ together with the atom to which they are attached form a ring, which optionally includes one or more heteroatoms selected from the group consisting of N, O and S, wherein N may be optionally substituted with a substituent selected from the group consisting of hydrogen, $C_{1-8}$alkyl and $C_{6-14}$aryl$C_{1-8}$alkyl;

or a pharmaceutically acceptable derivative thereof.

The present invention features compounds of formula (IB), wherein $R^1$ is a substituent in either the 3 or 5 position, or in both the 3 and 5 positions, independently selected from the group consisting of halogen, $C_{1-8}$alkyl, —$CF_3$ and —CN;

$R^2$ is halogen;

$R^3$ is $C_{1-8}$alkyl;

$R^{15}$ and $R^{16}$ together with the atom to which they are attached form a ring, which optionally includes one or more heteroatoms selected from the group consisting of N, O and S, wherein N may be optionally substituted with a substituent selected from the group consisting of hydrogen, $C_{1-8}$alkyl and $C_{6-14}$aryl$C_{1-8}$alkyl;

or a pharmaceutically acceptable derivative thereof.

The present invention features compounds selected from the group consisting of:

N-{4-[(acetylamino)sulfonyl]-2-methylphenyl}-2-[4-chloro-2-(3-cyano-5-methylbenzoyl)phenoxy]acetamide;

2-[4-chloro-2-(3-cyano-5-methylbenzoyl)phenoxy]-N-{4-[(isobutyrylamino)sulfonyl]-2-methylphenyl}acetamide;

2-[4-chloro-2-(3-cyano-5-methylbenzoyl)phenoxy]-N-{2-methyl-4-[(propionylamino)sulfonyl]phenyl}acetamide;

2-[4-chloro-2-(3-cyano-5-methylbenzoyl)phenoxy]-N-(2-methyl-4-{[(1-pyrrolidinylacetyl)amino]sulfonyl}phenyl)acetamide;

2-[4-chloro-2-(3-cyano-5-methylbenzoyl)phenoxy]-N-(2-methyl-4-{[(1-piperidinylacetyl)amino]sulfonyl}phenyl)acetamide;

2-[4-chloro-2-(3-cyano-5-methylbenzoyl)phenoxy]-N-(2-methyl-4-{[(4-morpholinylacetyl)amino]sulfonyl}phenyl)acetamide;

2-{4-chloro-2-[3-cyano-5-(trifluoromethyl)benzoyl]phenoxy}-N-{2-methyl-4-[(propionylamino)sulfonyl]phenyl}acetamide;

2-{4-chloro-2-[3-cyano-5-(trifluoromethyl)benzoyl]phenoxy}-N-{4-[(isobutyrylamino)sulfonyl]-2-methylphenyl}acetamide;

2-{4-chloro-2-[3-cyano-5-(trifluoromethyl)benzoyl]phenoxy}-N-(2-methyl-4-{[(3-methylbutanoyl)amino]sulfonyl}phenyl)acetamide;

2-[4-chloro-2-(3-chloro-5-cyanobenzoyl)phenoxy]-N-{2-methyl-4-[(propionylamino)sulfonyl]phenyl}acetamide;

2-[4-chloro-2-(3-chloro-5-cyanobenzoyl)phenoxy]-N-{4-[(isobutyrylamino)sulfonyl]-2-methylphenyl}acetamide;

2-[4-chloro-2-(3-chloro-5-cyanobenzoyl)phenoxy]-N-(2-methyl-4-{[(3-methylbutanoyl)amino]sulfonyl}phenyl)acetamide;

2-[4-chloro-2-(3-chloro-5-cyanobenzoyl)phenoxy]-N-(2-methyl-4-{[(1-pyrrolidinylacetyl)amino]sulfonyl}phenyl)acetamide;

N-{4-[(butyrylamino)sulfonyl]-2-methylphenyl}-2-[4-chloro-2-(3-chloro-5-cyanobenzoyl)phenoxy]acetamide;

2-[4-chloro-2-(3-chloro-5-cyanobenzoyl)phenoxy]-N-{2-methyl-4-[(pentanoylamino)sulfonyl]phenyl}acetamide;

isobutyl {4-[({4-chloro-2-[3-cyano-5-(trifluoromethyl)benzoyl]phenoxy}acetyl)amino]-3-methylphenyl}sulfonylcarbamate;

isobutyl [4-({[4-chloro-2-(3-chloro-5-cyanobenzoyl)phenoxy]acetyl}amino)-3-methylphenyl]sulfonylcarbamate;

2-methoxyethyl [4-({[4-chloro-2-(3-chloro-5-cyanobenzoyl)phenoxy]acetyl}amino)-3-methylphenyl]sulfonylcarbamate;

2-[4-chloro-2-(3-chloro-5-cyanobenzoyl)phenoxy]-N-(4-{[(methoxyacetyl)amino]sulfonyl}-2-methylphenyl)acetamide;

2-{4-chloro-2-[3-fluoro-5-(trifluoromethyl)benzoyl]phenoxy}-N-(4-{[(ethoxymethyl)amino]sulfonyl}-2-methylphenyl)acetamide;

2-{4-chloro-2-[3-fluoro-5-(trifluoromethyl)benzoyl]phenoxy}-N-{4-[({[2-(2-methoxyethoxy)ethoxy]methyl}amino)sulfonyl]-2-methylphenyl}acetamide;

2-{4-chloro-2-[3-fluoro-5-(trifluoromethyl)benzoyl]phenoxy}-N-(2-methyl-4-{[methyl(4-morpholinylacetyl)amino]sulfonyl}phenyl)acetamide;

$N^1$-{[4-({[4-chloro-2-(3-chloro-5-cyanobenzoyl)phenoxy]acetyl}amino)-3-methylphenyl]sulfonyl}-L-isoleucinamide;

$N^1$-{[4-({[4-chloro-2-(3-chloro-5-cyanobenzoyl)phenoxy]acetyl)}amino)-3-methylphenyl]sulfonyl}valinamide;

$N^1$-{[4-({[4-chloro-2-(3-chloro-5-cyanobenzoyl)phenoxy]acetyl}amino)-3-methylphenyl]sulfonyl}-L-leucinamide;

$N^1$-{[4-({[4-chloro-2-(3-chloro-5-cyanobenzoyl)phenoxy]acetyl}amino)-3-methylphenyl]sulfonyl}-D-alaninamide;

$N^1$-{[4-({[4-chloro-2-(3-chloro-5-cyanobenzoyl)phenoxy]acetyl}amino)-3-methylphenyl]sulfonyl}glycinamide;

N-{4-[(acetylamino)sulfonyl]-2-methylphenyl}-2-[4-chloro-2-(3-chloro-5-cyanobenzoyl)phenoxy]acetamide;

N-{[4-({[4-chloro-2-(3-chloro-5-cyanobenzoyl)phenoxy]acetyl}amino)-3-methylphenyl]sulfonyl}-1-methylprolinamide;

2-[4-chloro-2-(3-chloro-5-cyanobenzoyl)phenoxy]-N-(4-{[isobutyryl(methyl)amino]sulfonyl}-2-methylphenyl)acetamide;

2-[4-chloro-2-(3-chloro-5-cyanobenzoyl)phenoxy]-N-(2-methyl-4-{[methyl(propionyl)amino]sulfonyl}phenyl)acetamide;

N-(4-{[acetyl(methyl)amino]sulfonyl}-2-methylphenyl)-2-[4-chloro-2-(3-chloro-5-cyanobenzoyl)phenoxy]acetamide;

2-[4-chloro-2-(3-chloro-5-cyanobenzoyl)phenoxy]-N-{4-[(hexanoylamino)sulfonyl]-2-methylphenyl}acetamide;

2-[4-chloro-2-(3-chloro-5-cyanobenzoyl)phenoxy]-N-{4-[(heptanoylamino)sulfonyl]-2-methylphenyl}acetamide;

2-[4-chloro-2-(3-chloro-5-cyanobenzoyl)phenoxy]-N-{2-methyl-4-[(octanoylamino)sulfonyl]phenyl}acetamide;

2-[4-chloro-2-(3-chloro-5-cyanobenzoyl)phenoxy]-N-{2-methyl-4-[(nonanoylamino)sulfonyl]phenyl}acetamide;

isopropyl [4-({[4-chloro-2-(3-chloro-5-cyanobenzoyl)phenoxy]acetyl}amino)-3-methylphenyl]sulfonylcarbamate;

ethyl [4-({[4-chloro-2-(3-chloro-5-cyanobenzoyl)phenoxy]acetyl}amino)-3-methylphenyl]sulfonylcarbamate;

methyl [4-({[4-chloro-2-(3-chloro-5-cyanobenzoyl)phenoxy]acetyl}amino)-3-methylphenyl]sulfonylcarbamate;

and pharmaceutically acceptable derivatives thereof.

The present invention features compounds selected from the group consisting of:

N-{4-[(acetylamino)sulfonyl]-2-methylphenyl}-2-[4-chloro-2-(3-cyano-5-methylbenzoyl)phenoxy]acetamide, sodium salt;

2-[4-chloro-2-(3-cyano-5-methylbenzoyl)phenoxy]-N-{4-[(isobutyrylamino)sulfonyl]-2-methylphenyl}acetamide, sodium salt;

2-[4-chloro-2-(3-cyano-5-methylbenzoyl)phenoxy]-N-{2-methyl-4-[(propionylamino)sulfonyl]phenyl}acetamide, sodium salt;

2-{4-chloro-2-[3-cyano-5-(trifluoromethyl)benzoyl]phenoxy}-N-{2-methyl-4-[(propionylamino)sulfonyl]phenyl}acetamide, sodium salt;

2-{4-chloro-2-[3-cyano-5-(trifluoromethyl)benzoyl]phenoxy}-N-{4-[(isobutyrylamino)sulfonyl]-2-methylphenyl}acetamide, sodium salt;

2-{4-chloro-2-[3-cyano-5-(trifluoromethyl)benzoyl]phenoxy}-N-(2-methyl-4-{[(3-methylbutanoyl)amino]sulfonyl}phenyl)acetamide, sodium salt;

2-[4-chloro-2-(3-chloro-5-cyanobenzoyl)phenoxy]-N-{2-methyl-4-[(propionylamino)sulfonyl]phenyl}acetamide, sodium salt;

2-[4-chloro-2-(3-chloro-5-cyanobenzoyl)phenoxy]-N-{2-methyl-4-[(propionylamino)sulfonyl]phenyl}acetamide, choline salt;

2-[4-chloro-2-(3-chloro-5-cyanobenzoyl)phenoxy]-N-{2-methyl-4-[(propionylamino)sulfonyl]phenyl}acetamide, ethanolamine salt;

2-[4-chloro-2-(3-chloro-5-cyanobenzoyl)phenoxy]-N-{4-[(isobutyrylamino)sulfonyl]-2-methylphenyl}acetamide, sodium salt;

2-[4-chloro-2-(3-chloro-5-cyanobenzoyl)phenoxy]-N-(2-methyl-4-{[(3-methylbutanoyl)amino]sulfonyl}phenyl)acetamide, sodium salt;

N-{4-[(butyrylamino)sulfonyl]-2-methylphenyl}-2-[4-chloro-2-(3-chloro-5-cyanobenzoyl)phenoxy]acetamide, sodium salt;

2-[4-chloro-2-(3-chloro-5-cyanobenzoyl)phenoxy]-N-{2-methyl-4-[(pentanoylamino)sulfonyl]phenyl}acetamide, sodium salt;

isobutyl {4-[({4-chloro-2-[3-cyano-5-(trifluoromethyl)benzoyl]phenoxy}acetyl)amino]-3-methylphenyl}sulfonylcarbamate, sodium salt;

isobutyl [4-({[4-chloro-2-(3-chloro-5-cyanobenzoyl)phenoxy]acetyl}amino)-3-methylphenyl]sulfonylcarbamate, sodium salt;

2-methoxyethyl [4-({[4-chloro-2-(3-chloro-5-cyanobenzoyl)phenoxy]acetyl}amino)-3-methylphenyl]sulfonylcarbamate, sodium salt;

2-[4-chloro-2-(3-chloro-5-cyanobenzoyl)phenoxy]-N-(4-{[(methoxyacetyl)amino]sulfonyl}-2-methylphenyl)acetamide, sodium salt;

$N^1$-{[4-({[4-chloro-2-(3-chloro-5-cyanobenzoyl)phenoxy]acetyl}amino)-3-methylphenyl]sulfonyl}glycinamide, sodium salt;

2-[4-chloro-2-(3-chloro-5-cyanobenzoyl)phenoxy]-N-(4-{[isobutyryl(methyl)amino]sulfonyl}-2-methylphenyl)acetamide;

2-[4-chloro-2-(3-chloro-5-cyanobenzoyl)phenoxy]-N-(2-methyl-4-{[methyl(propionyl)amino]sulfonyl}phenyl)acetamide;

N-(4-{[acetyl(methyl)amino]sulfonyl}-2-methylphenyl)-2-[4-chloro-2-(3-chloro-5-cyanobenzoyl)phenoxy]acetamide;

2-[4-chloro-2-(3-chloro-5-cyanobenzoyl)phenoxy]-N-{4-[(hexanoylamino)sulfonyl]-2-methylphenyl}acetamide, sodium salt;

2-[4-chloro-2-(3-chloro-5-cyanobenzoyl)phenoxy]-N-{4-[(heptanoylamino)sulfonyl]-2-methylphenyl}acetamide, sodium salt;

2-[4-chloro-2-(3-chloro-5-cyanobenzoyl)phenoxy]-N-{2-methyl-4-[(octanoylamino)sulfonyl]phenyl}acetamide, sodium salt;

2-[4-chloro-2-(3-chloro-5-cyanobenzoyl)phenoxy]-N-{2-methyl-4-[(nonanoylamino)sulfonyl]phenyl}acetamide, sodium salt;

isopropyl [4-({[4-chloro-2-(3-chloro-5-cyanobenzoyl)phenoxy]acetyl}amino)-3-methylphenyl]sulfonylcarbamate, sodium salt;

ethyl [4-({[4-chloro-2-(3-chloro-5-cyanobenzoyl)phenoxy]acetyl) amino)-3-methylphenyl]sulfonylcarbamate, sodium salt;

methyl [4-({[4-chloro-2-(3-chloro-5-cyanobenzoyl)phenoxy]acetyl}amino)-3-methylphenyl]sulfonylcarbamate, sodium salt;

and pharamceutically acceptable derivatives thereof.

The present invention features sodium, calcium, potassium, magnesium, choline, ethanolamine, and triethylamine salts of compounds selected from the group consisting of:

N-{4-[(acetylamino)sulfonyl]-2-methylphenyl}-2-[4-chloro-2-(3-cyano-5-methylbenzoyl)phenoxy]acetamide;

2-[4-chloro-2-(3-cyano-5-methylbenzoyl)phenoxy]-N-{4-[(isobutyrylamino)sulfonyl]-2-methylphenyl}acetamide;

2-[4-chloro-2-(3-cyano-5-methylbenzoyl)phenoxy]-N-{2-methyl-4-[(propionylamino)sulfonyl]phenyl}acetamide;

2-[4-chloro-2-(3-cyano-5-methylbenzoyl)phenoxy]-N-(2-methyl-4-{[(1-pyrrolidinylacetyl)amino]sulfonyl}phenyl)acetamide;

2-[4-chloro-2-(3-cyano-5-methylbenzoyl)phenoxy]-N-(2-methyl-4-{[(1-piperidinylacetyl)amino]sulfonyl}phenyl)acetamide;

2-[4-chloro-2-(3-cyano-5-methylbenzoyl)phenoxy]-N-(2-methyl-4-{[(4-morpholinylacetyl)amino]sulfonyl}phenyl)acetamide;

2-{4-chloro-2-[3-cyano-5-(trifluoromethyl)benzoyl]phenoxy}-N-{2-methyl-4-[(propionylamino)sulfonyl]phenyl}acetamide;

2-{4-chloro-2-[3-cyano-5-(trifluoromethyl)benzoyl]phenoxy}-N-{4-[(isobutyrylamino)sulfonyl]-2-methylphenyl}acetamide;

2-{4-chloro-2-[3-cyano-5-(trifluoromethyl)benzoyl]phenoxy}-N-(2-methyl-4-{[(3-methylbutanoyl)amino]sulfonyl}phenyl)acetamide;

2-[4-chloro-2-(3-chloro-5-cyanobenzoyl)phenoxy]-N-{2-methyl-4-[(propionylamino)sulfonyl]phenyl}acetamide;

2-[4-chloro-2-(3-chloro-5-cyanobenzoyl)phenoxy]-N-{4-[(isobutyrylamino)sulfonyl]-2-methylphenyl) acetamide;

2-[4-chloro-2-(3-chloro-5-cyanobenzoyl)phenoxy]-N-(2-methyl-4-{[(3-methylbutanoyl)amino]sulfonyl}phenyl)acetamide;

2-[4-chloro-2-(3-chloro-5-cyanobenzoyl)phenoxy]-N-(2-methyl-4-{[(1-pyrrolidinylacetyl)amino]sulfonyl}phenyl)acetamide;

N-{4-[(butyrylamino)sulfonyl]-2-methylphenyl}-2-[4-chloro-2-(3-chloro-5-cyanobenzoyl)phenoxy]acetamide;

2-[4-chloro-2-(3-chloro-5-cyanobenzoyl)phenoxy]-N-{2-methyl-4-[(pentanoylamino)sulfonyl]phenyl}acetamide;

isobutyl {4-[({4-chloro-2-[3-cyano-5-(trifluoromethyl)benzoyl]phenoxy}acetyl)amino]-3-methylphenyl}sulfonylcarbamate;

isobutyl [4-({[4-chloro-2-(3-chloro-5-cyanobenzoyl)phenoxy]acetyl}amino)-3-methylphenyl]sulfonylcarbamate;

2-methoxyethyl [4-({[4-chloro-2-(3-chloro-5-cyanobenzoyl)phenoxy]acetyl}amino)-3-methylphenyl]sulfonylcarbamate;

2-[4-chloro-2-(3-chloro-5-cyanobenzoyl)phenoxy]-N-(4-{[(methoxyacetyl)amino]sulfonyl}-2-methylphenyl)acetamide;

2-{4-chloro-2-[3-fluoro-5-(trifluoromethyl)benzoyl]phenoxy}-N-(4-{[(ethoxymethyl)amino]sulfonyl}-2-methylphenyl)acetamide;

2-{4-chloro-2-[3-fluoro-5-(trifluoromethyl)benzoyl]phenoxy}-N-{4-[({[2-(2-methoxyethoxy)ethoxy]methyl}amino)sulfonyl]-2-methylphenyl}acetamide;

2-{4-chloro-2-[3-fluoro-5-(trifluoromethyl)benzoyl]phenoxy}-N-(2-methyl-4-{[methyl(4-morpholinylacetyl)amino]sulfonyl}phenyl)acetamide;

and pharmaceutically acceptable derivatives thereof.

The compounds according to the invention contain one or more asymmetric carbon atoms and thus occur as racemates and racemic mixtures, single enantiomers, diastereomeric mixtures and individual diastereoisomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in a mixture of forms and/or solvates or as a mixture of amorphous material and one or more forms and/or solvates. In general, all physical forms are equivalent for the uses contemplated by the present invention and are intended to be within the scope of the present invention.

Preferred compounds of the present invention include 2-[4-chloro-2-(3-chloro-5-cyanobenzoyl)phenoxy]-N-{2-methyl-4-[(propionylamino)sulfonyl]phenyl}acetamide sodium salt forms 1, 9, 10, and 12; 2-[4-chloro-2-(3-chloro-5-cyanobenzoyl)phenoxy]-N-{2-methyl-4-[(propionylamino)sulfonyl]phenyl}acetamide choline salt forms 1, 2, 3, and 4; and 2-[4-chloro-2-(3-chloro-5-cyanobenzoyl)phenoxy]-N-{2-methyl-4-[(propionylamino)sulfonyl]phenyl}acetamide calcium salt forms 2 and 3.

The term "alkyl", alone or in combination with any other term, refers to a straight-chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl," alone or in combination with any other term, refers to a straight-chain or branched-chain alkyl group with at least one carbon-carbon double bond. Examples of alkenyl radicals include, but are not limited to, ethenyl, propenyl, isopropenyl, butenyl, isobutenyl, pentenyl, hexenyl, hexadienyl and the like.

The term "alkynyl" refers to hydrocarbon groups of either a straight or branched configuration with one or more carbon-carbon triple bonds which may occur in any stable point along the chain, such as ethynyl, propynyl, butynyl, pentynyl, and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "cycloalkyl" refers to a saturated or partially saturated carbocyclic ring composed of 3–6 carbons in any chemically stable configuration. Examples of suitable carbocyclic groups include cyclopropyl, cyclobutyl, cyclopentyl, cyclohexyl, and cyclohexenyl.

The terms "aryl" alone or in combination with any other term, refers to a carbocyclic aromatic moiety (such as phenyl or naphthyl) containing the specified number of carbon atoms, preferably from 6–14 carbon atoms, and more preferably from 6–10 carbon atoms. Examples of aryl radicals include, but are not limited to phenyl, naphthyl, indenyl, indanyl, azulenyl, fluorenyl, anthracenyl and the like.

The term "heterocycle," "heterocyclic," and "heterocyclyl" as used herein, refer to a 3- to 7-membered monocyclic heterocyclic ring or 8-to 11-membered bicyclic heterocyclic ring which is either saturated, partially saturated or unsaturated, and which may be optionally benzofused if monocyclic. Each heterocycle consists of one or more carbon atoms and from one to four heteroatoms selected from the group consisting of N, O and S, and wherein the nitrogen and sulfur heteroatoms may optionally be oxidized, and including any bicyclic group in which any of the above-defined heterocyclic rings is fused to a benzene ring. The heterocyclic ring may be attached at any carbon or heteroatom, which results in the creation of a stable structure. Preferred heterocycles include 5–7 membered monocyclic heterocycles and 8–10 membered bicyclic heterocycles. Examples of such groups include imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetahydrofurodihydrofuranyl, tetrahydropyranodihydrofuranyl, dihydropyranyl, tetradyrofurofuranyl and tetrahydropyranofuiranyl.

Preferred heterocycles include imidazolidinyl, indazolyl, pyrrolidinyl, thiamorpholinyl, thiophenyl, furyl, benzofuranyl, thiazolyl, oxazolyl, pyrrolyl, indolinolyl, benzthiazolyl, pyridinolyl, quinolinoyl, and benzothiophenyl.

The term "halogen" refers to fluorine, chlorine, bromine or iodine.

The term "pharmaceutically effective amount" refers to an amount effective in treating a virus infection, for example an HIV infection, in a patient either as monotherapy or in combination with other agents. The term "treating" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylactically effective amount" refers to an amount effective in preventing a virus infection, for example an HIV infection, or preventing the occurrence of symptoms of such an infection, in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the antiviral agent.

As used herein, the compounds according to the invention are defined to include pharmaceutically acceptable derivatives thereof. A "pharmaceutically acceptable derivative" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium, $NW_4^+$ (wherein W is $C_{1-4}$ alkyl) and other amine salts. Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_{1-4}^+$, and $NW_4^+$ (wherein W is a $C_4$ alkyl group).

Preferred salts of the compounds of the invention are sodium, potassium, calcium, magnesium, choline, ethanolamine, and triethylamine.

Any reference to any of the above compounds also includes a reference to a pharmaceutically acceptable salt thereof.

Salts of the compounds of the present invention may be made by methods known to a person skilled in the art. For example, treatment of a compound of the present invention with an appropriate base or acid in an appropriate solvent will yield the corresponding salt. For example, treatment of 2-[4-chloro-2-(3-chloro-5-cyanobenzoyl)phenoxy]-N-{2-methyl-4-[(propionylamino)sulfonyl]phenyl}acetamide with an appropriate base, for example choline hydroxide or choline bicarbonate in various solvents, for example THF or isopropanol, will yield 2-[4-chloro-2-(3-chloro-5-cyanobenzoyl)phenoxy]-N-{2-methyl-4-[(propionylamino)sulfonyl]phenyl}acetamide choline salt.

The compounds of the present invention have certain pharmaceutic and pharmacokinetic properties that render them advantageous as therapeutic agents. For example, the compounds of the present invention can be made into salts which have improved solubility and increased bioavailability. The compounds of the present invention are prodrugs which are readily metabolized into the active inhibitors of HIV reverse transcriptase in vivo.

In a further aspect of the invention there are provided the compounds according to the invention for use in medical therapy particularly for the treatment or prophylaxis of viral infections such as an HIV infection. Compounds according to the invention have been shown to be active against HIV infections, although these compounds may be active against HBV infections as well.

The compounds according to the invention are particularly suited to the treatment or prophylaxis of HIV infections and associated conditions. Reference herein to treatment extends to prophylaxis as well as the treatment of established infections, symptoms, and associated clinical conditions such as AIDS related complex (ARC), Kaposi's sarcoma, and AIDS dementia.

According to a particular embodiment of the present invention, there is provided a method of treatment of HIV mutant viruses that exhibit NNRTI drug resistance by administering a pharmaceutically effective amount of a compound of the present invention or a pharmaceutically acceptable derivative thereof to a mammal, in particular a human. In particular, the compounds of the present invention may be used to treat wild-type HIV-1 as well as several mutants, for example, K103N, L1001, or Y181C.

According to another aspect, the present invention provides a method for the treatment or prevention of the symptoms or effects of a viral infection in an infected animal, for example, a mammal including a human, which comprises treating said animal with a pharmaceutically effective amount of a compound according to the invention. According to a particular embodiment of this aspect of the invention, the viral infection is a retroviral infection, in particular an HIV infection. A further aspect of the invention includes a method for the treatment or prevention of the symptoms or effects of an HBV infection.

The compounds according to the invention may also be used in adjuvant therapy in the treatment of HIV infections or HIV-associated symptoms or effects, for example Kaposi's sarcoma.

The present invention further provides a method for the treatment of a clinical condition in an animal, for example, a mammal including a human which clinical condition includes those which have been discussed in the introduction hereinbefore, which comprises treating said animal with a pharmaceutically effective amount of a compound according to the invention. The present invention also includes a method for the treatment or prophylaxis of any of the aforementioned infections or conditions.

In yet a further aspect, the present invention provides the use of a compound according to the invention in the manufacture of a medicament for the treatment or prophylaxis of any of the above mentioned viral infections or conditions.

The above compounds according to the invention and their pharmaceutically acceptable derivatives may be employed in combination with other therapeutic agents for the treatment of the above infections or conditions. Combination therapies according to the present invention comprise the administration of at least one compound of the present invention or a pharmaceutically acceptable derivative thereof and at least one other pharmaceutically active ingredient. The active ingredient(s) and pharmaceutically active agents may be administered simultaneously in either the same or different pharmaceutical compositions or sequentially in any order. The amounts of the active ingredient(s) and pharmaceutically active agent(s) and the relative timings of administration will be selected in order to achieve the desired combined therapeutic effect. Preferably the combination therapy involves the administration of one compound according to the invention and one of the agents mentioned herein below.

Examples of such further therapeutic agents include agents that are effective for the treatment of viral infections or associated conditions. Among these agents are (1-alpha, 2-beta, 3-alpha)-9-[2,3-bis(hydroxymethyl)cyclobutyl] guanine [(−)BHCG, SQ-34514, lobucavir], 9-[(2R,3R,4S)-3,4-bis(hydroxymethyl)-2-oxetanosyl]adenine (oxetanocin-G), TMC-114, BMS-232632, acyclic nucleosides, for example acyclovir, valaciclovir, famciclovir, ganciclovir, and penciclovir, acyclic nucleoside phosphonates, for example (S)-1-(3-hydroxy-2-phosphonyl-methoxypropyl) cytosine (HPMPC), [[[2-(6-amino-9H-purin-9-yl)ethoxy] methyl]phosphinylidene]bis(oxymethylene)-2,2-dimethylpropanoic acid (bis-POM PMEA, adefovir dipivoxil), [[(1R)-2-(6-amino-9H-purin-9-yl)-1-methylethoxy]methyl]phosphonic acid (tenofovir), and (R)-[[2-(6-Amino-9H-purin-9-yl)-1-methylethoxy]methyl] phosphonic acid bis-(isopropoxycarbonyloxymethyl)ester (bis-POC-PMPA), ribonucleotide reductase inhibitors, for example 2-acetylpyridine 5-[(2-chloroanilino)thiocarbonyl) thiocarbonohydrazone and hydroxyurea, nucleoside reverse transcriptase inhibitors, for example 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-beta-D-2,6-diaminopurine dioxolane (DAPD), 3'-azido-2',3'-dideoxythymidine-5'-H-phosphophonate (phosphonovir), 2'-deoxy-5-iodo-uridine (idoxuridine), (−)-cis-1-(2-hydroxymethyl)-1,3-oxathiolane 5-yl)-cytosine (lamivudine), cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclopropylamino)-9H-purin-9-yl]-2-cyclopentene-1-methanol (abacavir), 9-[4-hydroxy-2-(hydroxymethyl)but-1-yl]-guanine (H2G), ABT-606 (2HM-H2G) and ribavirin, protease inhibitors, for example indinavir, ritonavir, nelfinavir, amprenavir, saquinavir, (R)-N-tert-butyl-3-[(2S,3S)-2-hydroxy-3-N-[(R)-2-N-(isoquinolin-5-yloxyacetyl)amino-3-methylthiopropanoyl]amino-4-phenylbutanoyl]-5,5-dimethyl-1,3-thiazolidine-4-carboxamide (KNI-272), 4R-(4alpha,5alpha,6beta)]-1,3-bis[(3-aminophenyl)methyl] hexahydro-5,6-dihydroxy-4,7-bis(phenylmethyl)-2H-1,3-diazepin-2-one dimethanesulfonate (mozenavir), 3-[1-[3-[2-(5-trifluoromethylpyridinyl)-sulfonylamino]phenyl] propyl]-4-hydroxy-6alpha-phenethyl-6beta-propyl-5,6-dihydro-2-pyranone (tipranavir), N'-[2(S)-Hydroxy-3(S)-[N-(methoxycarbonyl)-1-tert-leucylamino]-4-phenylbutyl-$N^{alpha}$-(methoxycarbonyl)-N'-[4-(2-pyridyl)benzyl]-L-tert-leucylhydrazide (BMS-232632), 3-(2(S)-Hydroxy-3(S)-(3-hydroxy-2-methylbenzamido)-4-phenylbutanoyl)-5,5-dimethyl-N-(2-methylbenzyl)thiazolidine-4(R)-carboxamide (AG-1776), N-(2(R)-hydroxy-1(S)-indanyl)-2 (R)-phenyl-methyl-4(S)-hydroxy-5-(1-(1-(4-benzo[b] furanylmethyl)-2(S)-N'-(tert-butylcarboxamido) piperazinyl)pentanamide (MK-944A), and GW 433908, interferons such as α-interferon, renal excretion inhibitors such as probenecid, nucleoside transport inhibitors such as dipyridamole; pentoxifylline, N-acetylcysteine (NAC), Procysteine, α-trichosanthin, phosphonoformic acid, as well as immunomodulators such as interleukin II or thymosin, granulocyte macrophage colony stimulating factors, erythropoetin, soluble $CD_4$ and genetically engineered derivatives thereof, non-nucleoside reverse transcriptase inhibitors (NNRTIs), for example TMC-120, TMC-125, nevirapine (BI-RG-587), alpha-((2-acetyl-5-methylphenyl) amino)-2,6-dichloro-benzeneacetamide (loviride), 1-[3-(isopropylamino)-2-pyridyl]-4-[5-(methanesulfonamido)-1H-indol-2-ylcarbonyl]piperazine monomethanesulfonate (delavirdine), (10R,11S,12S)-12-Hydroxy-6,6,10,11-tetramethyl-4-propyl-11,12-dihydro-2H,6H,10H-benzo(1,2-b:3,4-b':5,6-b")tripyran-2-one((+) calanolide A), (4S)-6-Chloro-4-[1E)-cyclopropylethenyl)-3,4-dihydro-4-(trifluoromethyl)-2(1H)-quinazolinone (DPC-083), 1-(ethoxymethyl)-5-(1-methylethyl)-6-(phenylmethyl)-2,4 (1H,3H)-pyrimidinedione (MKC-442), and 5-(3,5-dichlorophenyl)thio-4-isopropyl-1-(4-pyridyl)methyl-1H-imidazol-2-ylmethyl carbamate (capravirine), glycoprotein 120 antagonists, for example PRO-2000, PRO-542 and 1,4-bis[3-[(2,4-dichlorophenyl)carbonylamino]-2-oxo-5,8-disodiumsulfanyl]naphthalyl-2,5-dimethoxyphenyl-1,4-dihydrazone (FP-21399), cytokine antagonists, for example reticulose (Product-R), 1,1'-azobis-formamide (ADA), S-1360 and 1,11-(1,4-phenylenebis(methylene))bis-1,4,8, 11-tetraazacyclotetradecane octahydrochloride (AMD-3100), or fusion inhibitors, for example T-20 and T-1249.

The carrier(s) must be pharmaceutically acceptable in the sense of being compatible with the other ingredients of the pharmaceutical composition and not deleterious to the recipient thereof.

More preferably the combination therapy involves the administration of one of the above mentioned agents and a compound within one of the preferred or particularly preferred sub-groups within formula (IA) or (IB) as described above. Most preferably the combination therapy involves the joint use of one of the above named agents together with one of the compounds of the present invention specifically named herein. The compounds of the combination may be administered simultaneously or sequentially.

The present invention further includes the use of a compound according to the invention in the manufacture of a medicament for simultaneous or sequential administration with at least one other therapeutic agent, such as those defined hereinbefore.

The compounds of formulas (IA), (IA'), and (IB), hereinafter known as the compounds of formula (I), may be synthesized by the following methods or by any method known in the art.

The compounds of the present invention may be prepared according to representative Schemes I–X, which are presented below. The compounds, which may be prepared according to these schemes, are not limited by the compounds contained in the schemes or by any particular substituents used in the schemes for illustrative purposes.

Compounds of formula (I) can be prepared from compounds of formula (II) and (III), wherein $R^1$, $R^2$, $R^3$ and $R^4$ are as hereinbefore defined, using suitable coupling conditions known in the art.

21

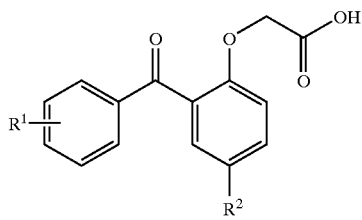

(II)

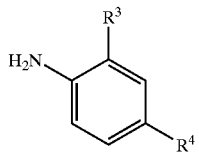

(III)

For example, compounds of formula (11) can be allowed to react with compounds of formula (III) in the presence of a suitable dehydrating agent, such as a carbodiimide, dicyclohexylcarbodiimide (DCC) for example, or more preferably 1-(3-dimethylaminopropyl)-3-ethylcarbodiimide hydrochloride (EDAC). In addition, the presence of a suitable activating agent, such as 1-hydroxybenztriazole (HOBt), is usually required to promote efficient coupling of the carboxylic acid to the appropriate amine. These reactions are typically carried out in an aprotic solvent such as acetonitrile, tetrahydrofuran or more preferably N,N-dimethylformamide (DMF), at temperatures from 0° C. to 150° C., most preferably at ambient temperatures.

Alternatively, compounds of formula (II), wherein $R^1$ and $R^2$ are as hereinbefore defined, can first be converted to the corresponding acid chloride which is then allowed to react with compounds of formula (III), wherein $R^3$ and $R^4$ are as hereinbefore defined, to afford compounds of formula (I). The preparation of the desired acid chloride can be accomplished by methods known in the art. The carboxylic acids can be allowed to react with a suitable dehydrating agent such as thionyl chloride or more preferably oxalyl chloride. These reactions are typically performed in an aprotic solvent such as acetonitrile or a chlorinated solvent such as chloroform or more preferably dichloromethane. The corresponding acid chlorides are not typically isolated in pure form, but instead are allowed to react directly with compounds of formula (III). Most often, reactions of the acid chlorides are performed in an aprotic solvent such as, acetone, acetonitrile or chloroform, or more preferably in N,N-dimethylformamide. In addition, the presence of a compound capable of acting as a base such as triethylamine or pyridine, or more preferably potassium bicarbonate, is required in order to obtain sufficient yields of the coupling products. When inorganic bases such as sodium bicarbonate are used, the addition of a small amount of water to the reaction mixture promotes an efficient coupling reaction. For example, carboxylic acid 70 (Scheme I) was allowed to react with oxalyl chloride in dichloromethane and in the presence of a catalytic amount of DMF to afford the corresponding acid chloride. The acid chloride was then allowed to react with amine 5 in a mixture of acetone and water and in the presence of an excess of sodium bicarbonate to provide compound 71.

22

Scheme I

Compounds of formula (I), in which $R^1$, $R^2$, $R^3$ are as hereinbefore defined, and $R^4$ is —$SO_2NR^5R^6$, wherein $R^5$ is hydrogen and $R^6$ is —$C(O)R^7$, wherein $R^7$ is as hereinbefore defined, can be prepared from compounds of formula (I), in which $R^1$, $R^2$, $R^3$ are as hereinbefore defined and $R^4$ is —$SO_2NR^5R^6$, in which both $R^5$ and $R^6$ are hydrogen, by reaction with compounds of formula (IV), in which $R^7$ is as hereinbefore defined.

(IV)

These reactions are typically conducted in an aprotic solvent, such as tetrahydrofuran, chloroform, or preferably dichloromethane. In addition, the reactions are performed in the presence of a compound capable of acting as a base, such as sodium bicarbonate, a trialkylamine, pyridine in combination with 4-N,N-dimethylaminopyridine (DMAP), or preferably with DMAP. Lastly, the reactions are conducted at temperatures in the range of −25 to 25° C., preferably 25° C.

Compounds of formula (IV), in which $R^7$ is as hereinbefore defined are either commercially available or can be prepared by methods known in the art.

Alternatively, compounds of formula (IA), in which $R^1$, $R^2$, $R^3$ are as hereinbefore defined, and $R^4$ is —$SO_2NR^5R^6$, wherein $R^5$ is hydrogen and $R^6$ is —$C(O)R^7$, wherein $R^7$ is as hereinbefore defined, can be prepared from compounds of formula (I), in which $R^1$, $R^2$, $R^3$ are as hereinbefore defined and $R^4$ is —$SO_2NR^5R^6$, in which both $R^5$ and $R^6$ are hydrogen, by reaction with compounds of formula (V), in which $R^7$ is as hereinbefore defined and $R^{16}$ is hydroxy or chlorine.

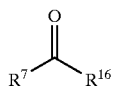

(V)

These reactions typically require the use of an agent capable of acting as a coupling or dehydrating agent, such as fuming sulfuric acid, more preferably N-(3-dimethylaminopropyl)-N'-ethylcarbodiimide hydrochloride in dichloromethane and in the presence of DMAP at ambient temperature. Compounds of formula (V), in which $R^7$ is as hereinbefore defined and $R^{16}$ is either hydroxy or chlorine are either commercially available or can be prepared by methods known in the art.

Compounds of formula (I), in which $R^1$, $R^2$, $R^3$ and $R^4$ are as hereinbefore defined, can be prepared from compounds of formula (VI), in which $R^1$ and $R^2$ are as hereinbefore defined and $R^{17}$ is hydrogen, by reaction with a compound of formula (VII), in which $R^3$ and $R^4$ are as hereinbefore defined and X is a suitable leaving group, such as bromine or tosylate, preferably iodine.

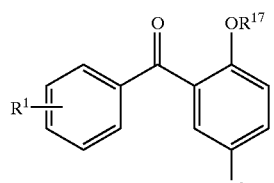

(VI)

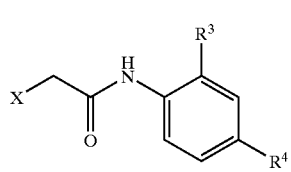

(VII)

For example, phenol 57 was allowed to react with amine 39 in the presence of potassium carbonate to provide compound 58.

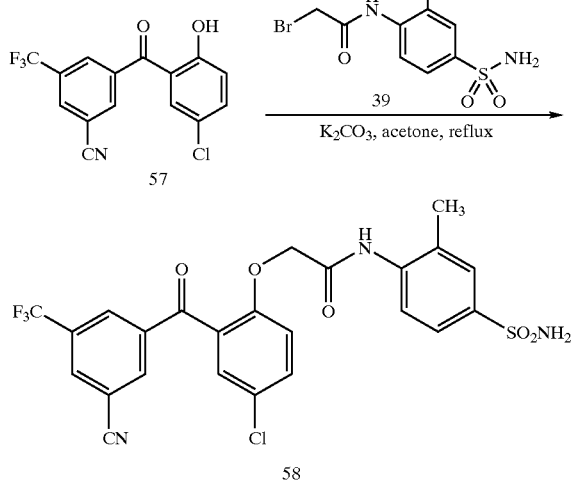

Scheme II

Compounds of formula (VI) in which $R^1$ and $R^2$ are as hereinbefore defined and $R^{17}$ is hydrogen can be prepared from compounds of formula (VI), wherein $R^1$ and $R^2$ are as hereinbefore defined and $R^{17}$ is methyl, by reaction with an agent capable of cleaving a methyl aryl ether such as trimethylsilyl iodide, or preferably boron tribromide. These reactions are typically performed in a chlorinated solvent such as dichloromethane and at temperatures from -100° C. to 25° C.

Compounds of formula (VI), wherein $R^1$ is —CN, $R^2$ is as hereinbefore defined and $R^{17}$ is methyl, can be prepared from compounds of formula (VI), wherein $R^1$ is bromine, $R^2$ is as hereinbefore defined and $R^{17}$ is methyl according to the procedure found in P. E. Maligres, *Tetrahedron Letters* 1999, 40, 8193–8195.

Compounds of formula (VII), in which $R^3$ and $R^4$ are as hereinbefore defined, can be prepared from compounds of formula (III), in which $R^3$ and $R^4$ are as hereinbefore defined, by reaction with compounds that are capable of acting as acylating agents, such as bromoacetyl bromide. These reactions are typically performed in aprotic solvents such as tetrahydrofuran, or chloroform, preferably dichloromethane. In addition, the reactions are conducted in the presence of a compound capable of acting as a base, such as sodium bicarbonate or triethylamine, preferably pyridine. Lastly, the reactions are conducted in a temperature range from -25 to 25° C., preferably 0° C.

Compounds of formula (III), in which $R^3$ and $R^4$ are as hereinbefore defined are either commercially available or can be prepared using methods known in the art.

Alternatively, compounds of formula (III), in which $R^4$ is —SO$_2$NR$^5$R$^6$, wherein R$^5$ is hydrogen and R$^6$ is —C(O)R$^7$, wherein R$^7$ is as hereinbefore defined, may be prepared from compounds of formula (III) in which $R^4$ is —SO$_2$NH$_2$ by reaction with a compound or a mixture of compounds capable of acting as an acylating agent, such as a mixture of a carboxylic acid and fuming sulfuric acid.

For example, 4-amino-3-methylbenzenesulfonamide 5 was allowed to react with acetic acid in fuming sulfuric acid at 0° C., to provide amine 6 (Scheme III).

Scheme III

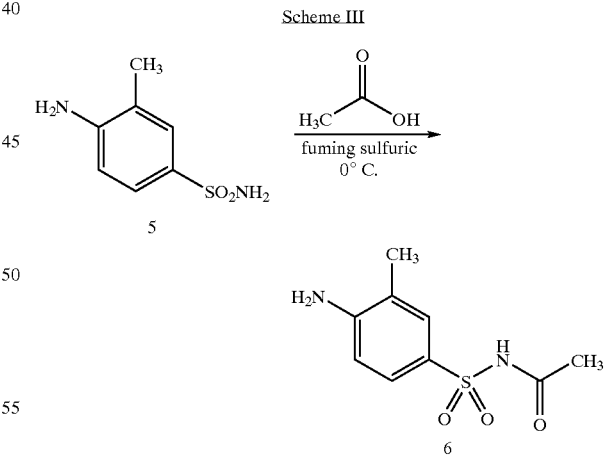

Compounds of formula (III), wherein $R^3$ is as hereinbefore defined and $R^4$ is —SO$_2$NR$^5$R$^6$, wherein both R$^5$ and R$^6$ are hydrogen are either commercially available or can be prepared from compounds of formula (III) wherein $R^3$ is as hereinbefore defined and $R^4$ is —SO$_3$H by reaction with a compound or mixture of compounds capable of simultaneously protecting the amino group and activating the sulfonic acid group, followed by reaction of the resulting sulfonyl chloride with a compound capable of converting it into a sulfonamide. These reactions can be performed with a variety of agents capable of simultaneously protecting the amino group as well as activating the sulfonic acid, such as a mixture of oxalyl chloride and N,N-dimethylformamide, or N-(chloromethylene)-N-methyhmethanaminium chloride. These reactions are typically performed in an aprotic solvent such as tetrahydrofuran or chloroform, preferably dichloromethane. The intermediate compound can then be allowed to react with an agent capable of converting the resulting sulfonyl chloride into a sulfonamide such as a mixture of ammonia in tetrahydrofuran, or preferably ammonium hydroxide in tetrahydrofuran.

For example, commercially available 2-aminotoluene-5-sulfonic acid was allowed to react with Villsmeyer reagent (N-(chloromethylene)-N-methylmethanaminium chloride), that is either commercially prepared or is generated in situ from a mixture of N,N-dimethylformamide and oxalyl chloride. The intermediate compound was then allowed to react with ammonium hydroxide in tetrahydrofuran to afford 4-amino-3-methylbenzenesulfonamide (Scheme IV).

Scheme IV

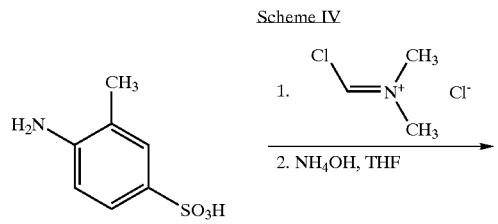

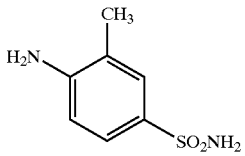

Alternatively, compounds of formula (III), wherein $R^3$ is as hereinbefore defined and $R^4$ is $—SO_2NR^5R^6$, wherein both $R^5$ and $R^6$ are hydrogen can be prepared from compounds of formula (III) wherein $R^3$ is as hereinbefore defined and $R^4$ is $—SO_3H$ in step-wise fashion through a series of reactions in which the amino group is first protected, the sulfonic acid moiety is activated and then converted into a sulfonamide group, followed by deprotection of the amino group.

For example, commercially available 2-aminotoluene-5-sulfonic acid was allowed to react with acetic anhydride in pyridine to afford pyridinium 4-(acetylamino)-3-methylbenzenesulfonate (Scheme V). The resulting salt was then allowed to react with sodium hydroxide to afford the corresponding sodium salt, sodium 4-(acetylamino)-3-methylbenzenesulfonate. The salt was then allowed to react with thionyl chloride to afford the intermediate sulfonyl chloride, followed by reaction with ammonia and subsequent deprotection by reaction with aqueous hydrochloric acid in ethanol to afford the desired sulfonamide.

Scheme V

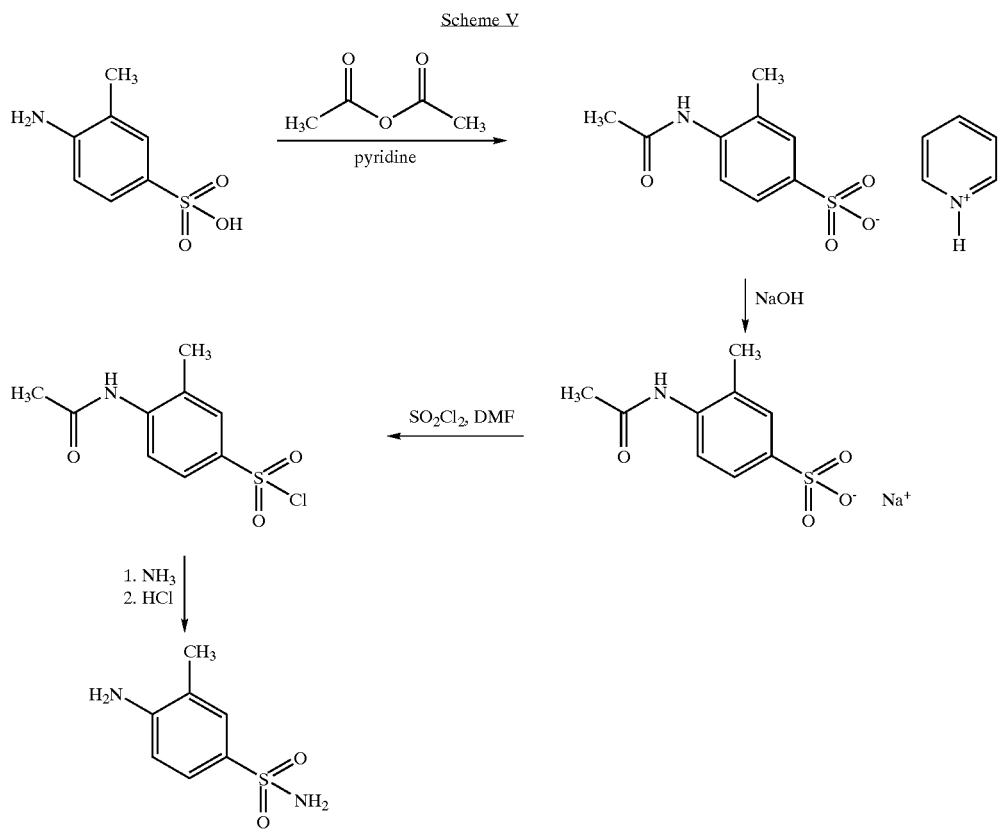

Compounds of formula (IB), wherein $R^1$, $R^2$ and $R^3$ are as hereinbefore defined and $R^{15}$ and $R^{16}$ are as hereinbefore defined, can be prepared from compounds of formula (IA) in which $R^1$, $R^2$ and $R^3$ are as hereinbefore defined, $R^4$ is —SO$_2$NR$^5$R$^6$, $R^5$ is hydrogen, $R^6$ is —C(O)R$^7$ and $R^7$ is haloC$_{1-8}$alkyl, by reaction with ammonia, or a primary, secondary or heterocyclic amine. For example, N-(4-{[(bromoacetyl)amino]sulfonyl}-2-methylphenyl)-2-[4-chloro-2-(3-chloro-5-cyanobenzoyl)phenoxy]acetamide (47) was allowed to react with pyrrolidine in the presence of sodium iodide in dichloromethane to afford 2-[4-chloro-2-(3-chloro-5-cyanobenzoyl)phenoxy]-N-(2-methyl-4-{[(1-pyrrolidinylacetyl)amino]sulfonyl}phenyl)acetamide (48) (Scheme VI).

Compounds of formula (IA), wherein $R^1$, $R^2$ and $R^3$ are as hereinbefore defined, $R^4$ is —SO$_2$NR$^5$R$^6$, $R^5$ is hydrogen, $R^6$ is —C(O)R$^7$ and $R^7$ is haloC$_{1-8}$alkyl, can be prepared from compounds of formula (IA) in which $R^1$, $R^2$ and $R^3$ are as hereinbefore defined, $R^4$ is —SO$_2$NR$^5$R$^6$, and both $R^5$ and $R^6$ are hydrogen, by reaction with a compound capable of acting as an acylating agent, such as bromoacetyl chloride, or bromoacetic anhydride.

For example, N-[4-(aminosulfonyl)-2-methylphenyl]-2-[4-chloro-2-(3-chloro-5-cyanobenzoyl)phenoxy]acetamide was allowed to react with bromoacetic anhydride in the presence of 4-N,N-dimethylaminopyridine (DMAP) in dichloromethane to afford, N-(4-{[(bromoacetyl)amino]sulfonyl}-2-methylphenyl)-2-[4-chloro-2-(3-chloro-5-cyanobenzoyl)phenoxy]acetamide (Scheme VII).

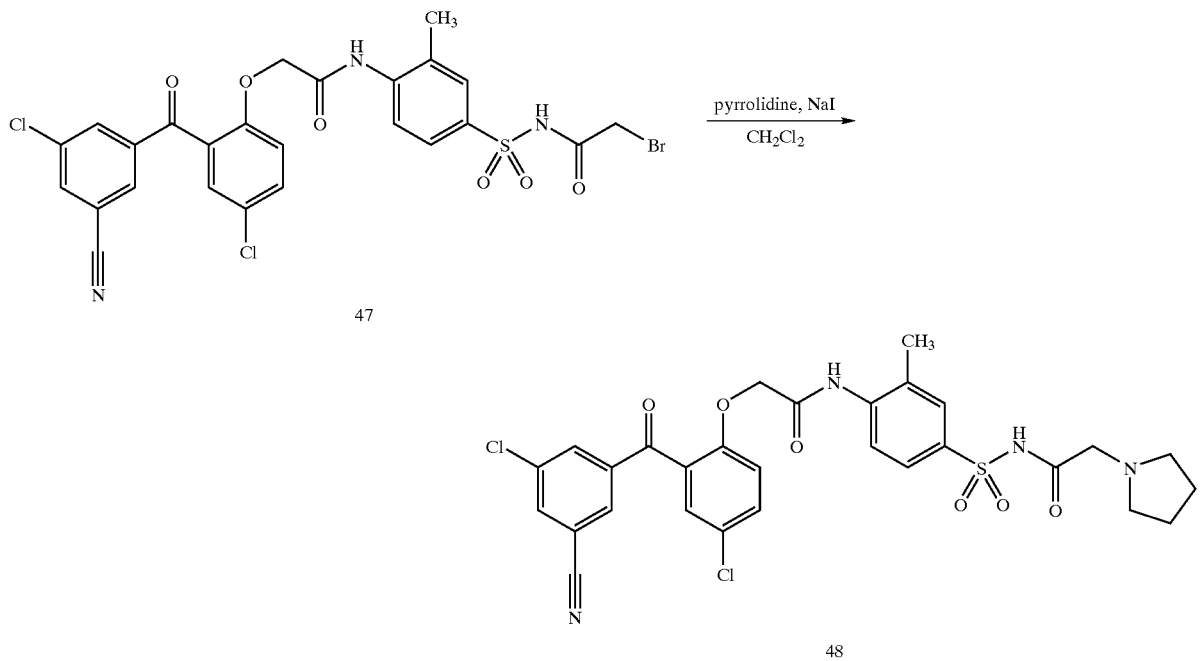

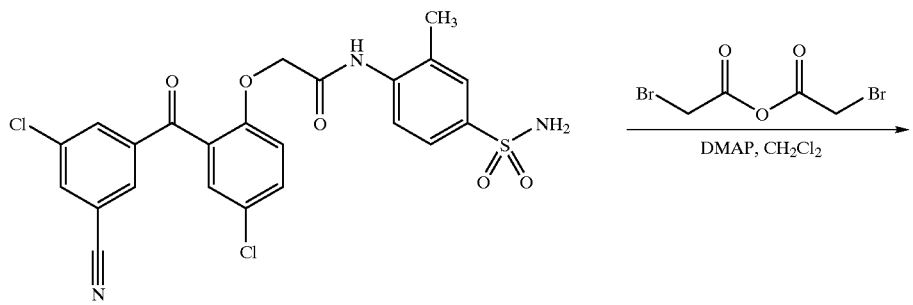

-continued

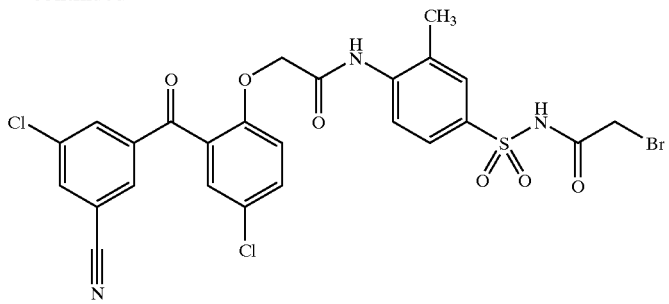

Compounds of formula (II), wherein $R^1$ and $R^2$ are as hereinbefore defined, can be prepared from compounds of formula (VI) by reaction with a suitable alkylating agent using methods known in the art.

Typically, the reactions are performed in an aprotic solvent such as acetonitrile, DMF, or more preferably acetone, and temperatures ranging from 40° C. to 100° C. In addition, the presence of an excess of a base such as triethylamine, pyridine, or more preferably potassium carbonate, is usually required for efficient reaction. For example, phenol 10 (Scheme VIII) was allowed to react with ethyl bromoacetate in refluxing acetone and in the presence of potassium carbonate to afford ester 11.

Scheme VIII

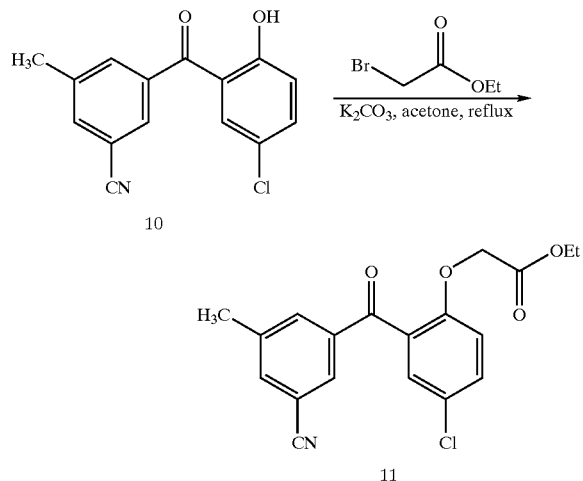

The intermediate esters, as in Scheme VIII, can then be converted to compounds of formula (II) by reaction with an agent capable of effecting saponification of the corresponding ester. A variety of inorganic bases can be used to affect the saponification of the esters, such as compound 11, including sodium carbonate, sodium hydroxide or more preferably lithium hydroxide. Typically, these reactions are performed in water in addition to a solvent that is miscible with water and is capable of dissolving the ester such as tetrahydrofuran, methyl alcohol or ethyl alcohol. For example, ester 11 (Scheme IX) was allowed to react with lithium hydroxide in a mixture of THF, water, and ethanol to afford carboxylic acid 12.

Scheme IX

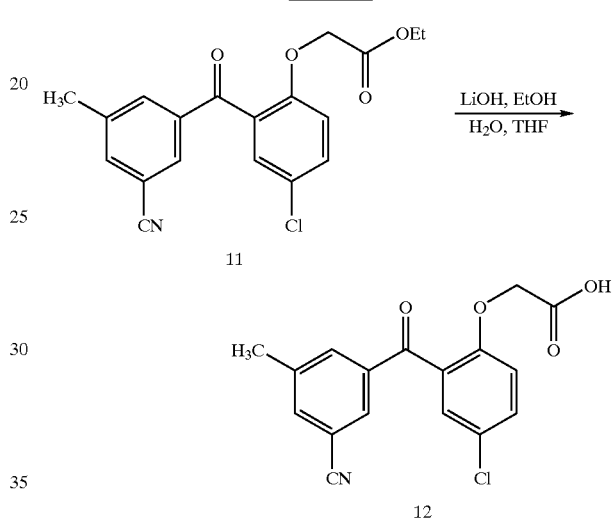

Below are schemes showing the preparation of compounds of formula (II), in which $R^1$ and $R^2$ are as hereinbefore defined. Compounds of formula (II) can be prepared by reaction of compounds of formula (VIII), wherein $R^{18}$ is halogen, preferably bromine or iodine, with compounds of formula (IX), wherein $R^1$ is hereinbefore defined.

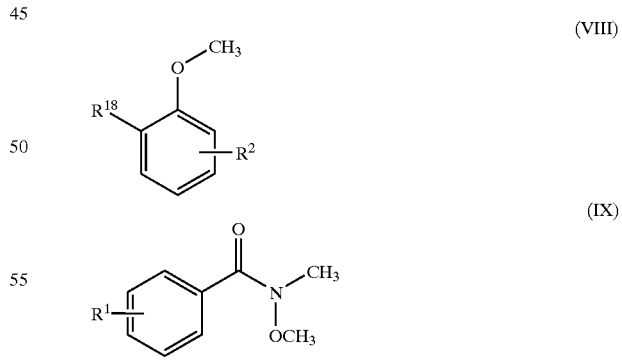

Typically, compounds of formula (VIII) are treated with an agent capable of effecting a halogen-metal exchange reaction, such as sec-butyl lithium, methyl lithium, tert-butyl lithium, or more preferably n-butyl lithium. The halogen-metal exchange can be performed in an ethereal solvent such as THF, dioxane or more preferably diethyl ether, and at low temperatures ranging from −100° C. to 0° C., most preferably −78° C. When the halogen-metal exchange reaction is complete, the resulting compounds of formula (VIII), in which $R^{18}$ is lithium, are allowed to react with compounds of formula (IX), again in an ethereal solvent and at low temperatures. For example, 2-bromo-4-chloroanisole (Scheme X) in diethyl ether was treated with n-butyl lithium at −78° C. After 15 minutes at −78° C., the resulting lithium species was allowed to react with amide 68 to afford the desired ketone 69.

Scheme X

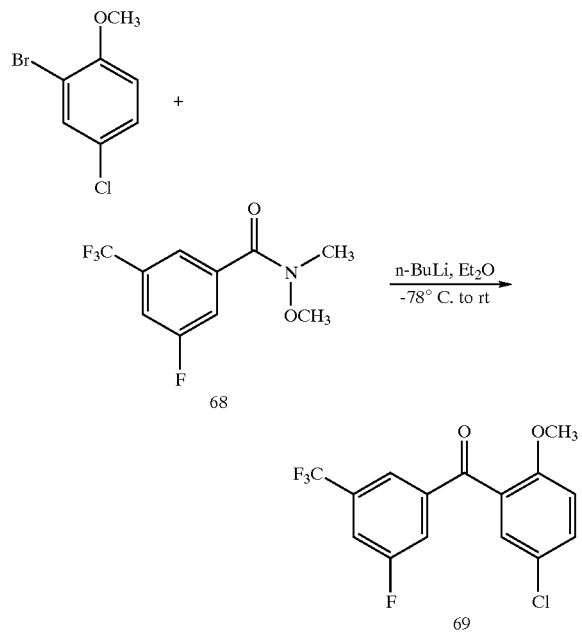

Compounds of formula (VIII), in which $R^2$ is as hereinbefore defined and $R^9$ is either bromine or iodine, are either commercially available or can be prepared using literature methods known in the art.

Compounds of formula (IX), in which $R^1$ is as hereinbefore defined, can be prepared from commercially available compounds or using methods known in the art.

Alternatively, compounds of formula (II) can be prepared by reaction of compounds of formula (X), wherein $R^1$ is as hereinbefore defined and $R^{19}$ is halogen, preferably bromine or iodine, with a compound of compound of formula (XI), wherein $R^2$ is as hereinbefore defined. These reactions are typically performed by reacting a compound capable of converting $R^{19}$ from halogen to lithium, such as n-butyl lithium or tert-butyl lithium. Further, these reactions are performed in an etherial solvent such as tetrahydrofuran or diethyl ether and at temperatures from −100° C. to 25° C.

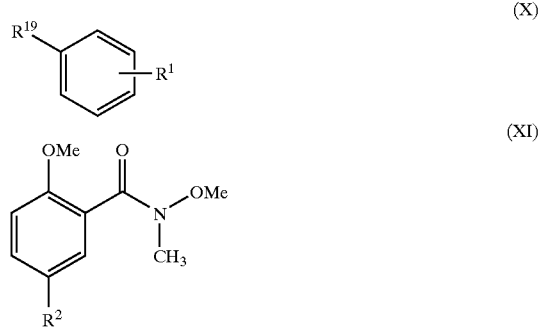

Compounds of formula (X), in which $R^1$ is as hereinbefore defined and $R^{19}$ is halogen, are commercially available or can be prepared using methods known in the art.

Compounds of formula (XI), in which $R^2$ is as hereinbefore defined, are commercially available or can be prepared using methods known in the art.

The compounds according to the invention, also referred to herein as the active ingredient, may be administered for therapy by any suitable route including oral, rectal, nasal, topical (including transdermal, buccal and sublingual), vaginal and parenteral (including subcutaneous, intramuscular, intravenous, intradermal, and intravitreal). It will be appreciated that the preferred route will vary with the condition and age of the recipient, the nature of the infection and the chosen active ingredient.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 0.5 to 30 mg per kilogram body weight per day and particularly in the range 1.0 to 20 mg per kilogram body weight per day. Unless otherwise indicated, all weights of active ingredient are calculated as the parent compound of formula (I); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 10 to 1000 mg or 50 to 500 mg, preferably 20 to 500 mg, and most preferably 50 to 400 mg of active ingredient per unit dosage form.

While it is possible for the active ingredient to be administered alone it is preferable to present it as a pharmaceutical composition. The compositions of the present invention comprise at least one active ingredient, as defined above, together with one or more acceptable carriers thereof and optionally other therapeutic agents. Each carrier must be "acceptable" in the sense of being compatible with the other ingredients of the composition and not injurious to the patient.

Pharmaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of formula (I) or a pharmaceutically acceptable derivative thereof and at least one further therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research* 3 (6), 318 (1986).

Pharmaceutical compositions of the present invention suitable for oral administration may be presented as discrete units such-as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for rectal administration may be presented as a suppository with a suitable base comprising, for example, cocoa butter or a salicylate.

Pharmaceutical compositions suitable for vaginal administration may be presented as pessaries, tampons, creams, gels, pastes, foams or spray Pharmaceutical compositions containing in addition to the active ingredient such carriers as are known in the art to be appropriate.

Pharmaceutical compositions suitable for rectal administration wherein the carrier is a solid are most preferably presented as unit dose suppositories. Suitable carriers include cocoa butter and other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, bacteriostats and solutes which render the Pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The Pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Preferred unit dosage pharmaceutical compositions are those containing a daily dose or daily subdose of the active ingredients, as hereinbefore recited, or an appropriate fraction thereof.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

The following examples are intended for illustration only and are not intended to limit the scope of the invention in any way. "Active ingredient" denotes a compound according to the invention or multiples thereof or a physiologically functional derivative of any of the aforementioned compounds.

General Procedures:

General procedure I: Friedel-Crafts Reaction of Acid Chlorides with 4-chloroanisole Into a round-bottom flask equipped with a stir bar, a reflux condenser, and nitrogen on demand, were placed 4-chloroanisole (1–1.25 mmol/mmol of acid chloride), aluminum chloride ($AlCl_3$, 1–1.75 mmol/mmol of acid chloride) and $CH_2Cl_2$. To the resulting mixture as added the appropriate acid chloride at rt. When the addition was complete, the orange mixture was heated to reflux and was allowed to stir for 2–24 h. The mixture was allowed to cool to rt and was carefully poured onto ice water, giving a two-phase mixture which was stirred at rt for 30 min to 2 h. It was then poured into a separatory funnel containing water. The organic layer was collected, washed with water, brine, dried over $MgSO_4$, filtered and the solvents were removed under reduced pressure. See specific examples for details regarding additional purification.

General procedure II: Alkylation of Phenols with Ethyl Bromoacetate

Into a round-bottom flask equipped with a stir bar, reflux condenser, and nitrogen on demand were placed the appropriate phenol, potassium carbonate (2–10 mmol/mmol of phenol), ethyl bromoacetate (1–1.5 mmol/mmol of phenol) and acetone (1–10 mL/mmol of phenol). The resulting mixture was heated to reflux for 1–20 h, after which time it was allowed to cool to rt and was poured into a separatory funnel containing ethyl acetate and water. The organic layer was collected and was washed with water, brine, dried over $MgSO_4$, filtered and the solvents were removed under reduced pressure to leave an oil. See specific examples for details regarding additional purification.

General Procedure III: Saponification of Ethyl Esters to the Carboxylic Acids

A round-bottom flask was equipped with a stir bar, nitrogen on demand and was flushed with nitrogen. To the flask were added tetrahydrofuran (THF, 1–5 mL/mmol of ester), ethyl alcohol (EtOH, 1–5 mL/mmol of ester), water (1–5 mL/mmol of ester) and lithium hydroxide monohydrate (1–5 mmol/mmol of ester). The resulting suspension was stirred vigorously and the ester was added in one portion. The mixture was allowed to stir at rt for 1–20 h, after which time the pH was adjusted to approximately pH 5 by the slow addition of 1 N aqueous hydrochloric acid. The mixture was then poured into a separatory funnel containing ethyl acetate and water. The organic layer was collected and was washed with water, brine, dried over MgSO$_4$, filtered and the solvents were removed under reduced pressure to leave a white solid. See specific examples to determine if further purification of the product was required, General Procedure IV: Coupling of the Acid to Aromatic Amines Using 1-(3-dimethylaminopropyl)-3-ethylcarbodiimide Hydrochloride (EDAC)

A round-bottom flask was equipped with a stir bar, nitrogen on demand and was flushed with nitrogen. To the flask were added the appropriate carboxylic acid, N,N-dimethylformamide (DMF, 5–20 mL/mmol acid), 1-hydroxybenztriazole (HOBt, 1–2 mmol/mmol acid), 1-(3-dimethylaminopropyl)-3-ethylcarbodiimide hydrochloride (EDAC, 1–5 mmol/mmol acid), and the appropriate aromatic amine (1–2 mmol/mmol acid). In some cases, triethylamine (Et$_3$N, 2–5 mmol/mmol of acid) was used. The resulting mixture was allowed to stir at rt for 2–24 h, after which time it was poured into a separatory funnel containing ethyl acetate and water. The organic layer was collected and was washed with water, brine, dried over MgSO$_4$, filtered and the solvents were removed under reduced pressure. See specific examples for details regarding further purification of the products.

General Procedure V: Synthesis of Acid Chlorides from Carboxylic Acids Using Oxalyl Chloride Into a round-bottom flask were placed the appropriate carboxylic acid, methylene chloride (CH$_2$Cl$_2$, 1–10 mL/mmol acid), and N,N-dimethylformamide (1–10 drops). The mixture was cooled to 0° C. and oxalyl chloride (1–2 mmol/mmol acid) was added dropwise, after which time the mixture was allowed to warm to rt and stir for 1–24 h. The solvents were then removed under reduced pressure and the remaining residue was dried in vacuo. In most cases, the acid chlorides were used immediately used in subsequent reactions with no further purification.

General Procedure VI: Coupling of Acid Chlorides to Aromatic Amines Using Sodium Bicarbonate Into a round-bottom flask were placed the appropriate aromatic amine, acetone (1–10 mL/mmol amine), sodium bicarbonate (2–10 mmol/mmol amine), and water (0.25–10 mL). The acid chloride was added as a solution in acetone (1–10 mL/mmol of acid chloride) in a dropwise manner and the reaction mixture was allowed to stir at rt for 1–24 h. When judged to be complete, the mixture was poured into a separatory funnel containing ethyl acetate and water. The organic layer was collected and was washed with water, brine, dried over MgSO$_4$, filtered and the solvents were removed under reduced pressure. See specific examples for details regarding further purification of the products.

Alternatively, the coupling procedure can be performed as described above except that DMF is used in place of acetone and potassium carbonate is used in place of sodium bicarbonate.

General Procedure VII: Synthesis of Weinreb Amides from Acid Chlorides Using N,O-dimethylhydroxylamine Hydrochloride Into a round bottom flask equipped with a stir bar and nitrogen on demand were placed the N,O-dimethylhydroxylamine (1–2 mmol/mmol acid chloride) and chloroform (CHCl$_3$, 1–10 mL/mmol acid chloride). The mixture was cooled to 0° C. and triethylamine (Et$_3$N, 1–5 mmol/mmol acid chloride) was added in one portion. The acid chloride was added and the reaction mixture was allowed to stir at 0° C. for 0.5–5 h, after which time was poured into a separatory funnel containing chloroform and water. The organics were collected, washed with water and brine, dried over MgSO$_4$, filtered and the solvents were removed under reduced pressure. See specific examples to determine if further purification of the product was required.

General Procedure VIII: Halogen-Metal Exchange of 2-bromo-4-chloroanisole, Followed by Addition of Weinreb Amides Into a round-bottom flask equipped with a stir bar, nitrogen on demand, and an addition funnel, were added 2-bromo-4-chloroanisole (1 mmol/mmol of amide) and diethyl ether (1–10 mL/mmol of anisole) and the mixture was cooled to −78° C. by means of a dry ice/acetone bath. n-Butyl lithium (1–2 mmol/mmol of anisole of a 2.5M soln. in hexanes) was added dropwise, followed by addition of the Weinreb amide. The reaction was allowed to stir at −78° C. for 0.5 h–1 h, at which time the reaction was allowed to warm to rt. When judged to be complete, the reaction was poured into a separatory funnel containing ether and water. The organics were collected, washed with water, dried over MgSO$_4$, filtered, and the solvents were removed under reduced pressure. See specific examples to determine if further purification was required.

General Procedure IX: Deprotection of Anisole Derivatives Using Boron Tribromide To a round-bottom flask equipped with a stir bar, nitrogen on demand, and an addition funnel was added the appropriate anisole derivative and methylene chloride (CH$_2$Cl$_2$, 1–15 mL/mmol of anisole). The mixture was cooled to −78° C. and boron tribromide was added dropwise at −78° C. The resulting mixture was allowed to stir at −78° C. for 30–120 minutes, after which time it was allowed to warm to rt and stir for an additional 15–120 minutes. When judged to be complete, the reaction was poured over ice and extracted with CH$_2$Cl$_2$. The organics were collected, washed with water, dried over MgSO$_4$, filtered, and the solvents were removed. See specific examples to determine if further purification was required.

General Procedure X. The appropriate acid chloride in acetonitrile was added dropwise via an addition funnel to a stirred solution of triethylamine (0–2.5 mmol/mmol acid chloride), acetonitrile (1–20 ml/mmol acid chloride), and the appropriate aniline (0.5–2.5 mmol/mmol acid chloride). The reaction was refluxed for 0–12 h. The heat was removed and the reaction mixture was stirred for 12–336 h. The mixture was concentrated, dissolved, and washed with water. The resulting organics were dried over MgSO$_4$ and concentrated in vacuo and purified as descried in the individual cases.

General Procedure XI. An amine (1–2.5 mmol/mmol benzene) was added dropwise via an addition funnel to a stirred suspension of a para-nitro halogenated benzene or toluene in pyridine (20–40 mmol/mmol benzene), sodium bicarbonate (1.5–4 mmol/mmol benzene), and water (0.2–5 mL/mmol benzene). The resulting suspension was refluxed (150° C.) for 1–7 days. The mixture was filtered and acetone (10–200 mL/mmol benzene) was added to the filtrate and brought to reflux. Water was added to the cloud point and the solution was cooled to rt. The precipitate was filtered and the resulting solid was washed with water and ether to afford the substituted product.

General Procedure XII. The appropriate nitro-benzene was added to a suspension of palladium on carbon (0.1–0.8 mmol/mmol benzene, 10% w/w), ethanol, THF, and methanol and the reaction vessel was evacuated and charged with nitrogen several times. After evacuating the reaction vessel under reduced pressure, it was charged with hydrogen (14–100 psi). The resulting suspension was stirred at rt for 0–72 h, filtered through a celite pad, and concentrated in vacuo to afford the appropriate aniline.

Alternatively, the reaction can be performed as described above, except that the solvent is ethanol, methanol, a mixture of ethanol and tetrahydrofuran, or a mixture of methanol and tetrahydrofuran.

General procedure XIII. Into a round-bottom flask equipped with a stir bar, cooling bath, and nitrogen on demand were placed the appropriate carboxylic acid, hexachloroacetone (HCA, 0.5 mmol/mmol acid), and THF (1–10 mL/mmol acid) and the mixture was cooled –78° C. Triphenylphosphine ($PPh_3$, 1 mmol/mmol acid) in THF (1–10 mL/mmol acid) was added to the mixture and stirred for 5–120 min. The appropriate aniline (1 mmol/mmol acid) in THF (1–10 mL/mmol acid) and pyridine (5–20 mmol/mmol acid) were added dropwise and the mixture was stirred –78° C. for 5–60 min. The cooling bath was removed and the mixture was stirred at rt for 1 h to 14 d. The reaction mixture was concentrated in vacuo and purified as described in the individual cases.

General procedure XIV. Thionyl chloride (1–100 mmol/mmol acid) was added to a solution of the appropriate carboxylic acid in methylene chloride (1–100 m/mmol acid) and the resulting solution was refluxed for 1–12 h under nitrogen. The mixture was concentrated in vacuo and placed under nitrogen to afford the appropriate acid chloride.

General Procedure XV: Palladium-Mediated Cyanation of Benzophenone Derivatives

The appropriate bromobenzophenone was treated according to the procedures outlined by Anderson et al. in *J. Org. Chem.* 1998, 63, 8224–8228. Into a heat-dried flask, fitted with a reflux condenser, was placed the bromo- or trifluoromethylsulfonyl-benzophenone (1 eq), tetrakis(triphenylphosphine) palladium (10–20%), copper iodide (2 eq relative to palladium), sodium cyanide (2 eq), and propionitrile (0.5–1.0 M in bromobenzophenone). The mixture was purged with $N_2$ for 30 min prior to use. The mixture was heated to 120° C. and stirred until TLC analysis showed complete disappearance of the starting material (1–16 h). The mixture was then cooled to rt, diluted with ethyl acetate, and filtered through silica gel, and the filtrate was concentrated in vacuo. The corresponding products were purified as described in each example.

Alternatively, the cyanation reaction can be performed as described in P. E. Maligres, *Tetrahedron Letters* 1999, 40, 8193–8195.

General Procedure XVI: Synthesis of N-[4(aminosulfonyl)-2-methylphenyl]acetamide and N-[4-(alkyl and Dialkyaminosulfonyl)-2-methylphenyl]acetamides Sulfonyl chloride 464 (1–100 mmol) was added to a solution of the appropriate amine in pyridine (1–10 mL/mmol amine) and the resulting solution was stirred for 1–48 h under nitrogen. Water was added and the resulting mixture was extracted with methylene chloride and the organics were concentrated in vacuo. The resulting products were then purified by flash chromatography to afford the appropriate acetyl protected sulfonamide.

General Procedure XVII: De-acetylation of N-[4-(aminosulfonyl)-2-methylphenyl]acetamide and N-[4-(Alkyl and Dialkyaminosulfonyl)-2-methylphenyl]acetamides The appropriate sulfonamide (1–100 mmol) was added to a solution of ethanol (1–50 mL), water (0–5 mL), and hydrochloric acid (1–28.9 M, 1–50 mL) in a large test tube. The mixture was then heated, with stirring, to 60° C. for 1–36 h. The mixture was allowed to cool to rt and concentrated in vacuo. The resulting products were dissolved in ethyl acetate and washed with saturated $NaHCO_3$, then purified by flash chromatography using 95:5 $CH_2Cl_2:CH_3OH$ as eluant to afford the desired aniline.

EXAMPLE 1

N-{4-[(acetylamino)sulfonyl]-2-methylphenyl}-2-[4-chloro-2-(3-cyano-5-methylbenzoyl)phenoxy]acetamide, Sodium Salt

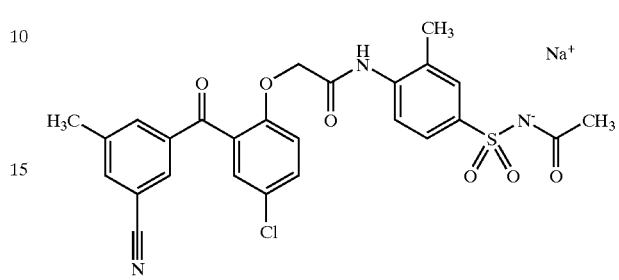

Step A:

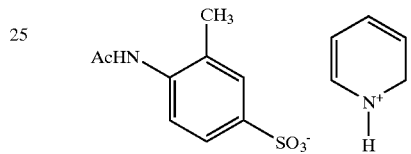

Into a round-bottom flask were placed 2-aminotoluene-5-sulfonic acid (50.0 g, 267 mmol), and pyridine (300 mL). Acetic anhydride (38 mL, 403 mmol) was added dropwise from an addition funnel and the resulting mixture was allowed to stir for 2 h at rt. The solvents were removed under reduced pressure, leaving a brown solid. Several portions of ethyl alcohol were added to the solid and subsequently removed under reduced pressure, to afford a brown solid which was filtered and washed with several additional portions of ethyl alcohol and dried under vacuum (67.03 g, 81%). $^1$H NMR (DMSO-$d_6$,) δ 2.08 (s, 3H), 2.22 (s, 3H), 7.39 (s, 2H), 7.45 (s, 1H), 8.02 (t, J=6 Hz, 2H), 8.53 (t, J=6 Hz, 1H), 8.92 (d, J=6 Hz, 2H), 9.31 (s, 1H).

Step B:

The compound from step A (67.03 g, 217 mmol) was added to a round-bottom flask containing 1N NaOH (225 mL) and the resulting mixture was allowed to stir at rt for 3 h. The mixture was concentrated under reduced pressure, to afford a brown solid. Several portions of ethyl alcohol were added and subsequently removed under reduced pressure. The remaining solid was filtered, washed with a final portion of ethyl alcohol and dried under vacuum (42.34 g, 77%). $^1$H NMR (DMSO-$d_6$, 300 MHz) δ 2.08 (s, 3H), 2.22 (s, 3H), 7.39 (s, 2H), 7.45 (s, 1H), 9.31 (s, 1H).

Step C:

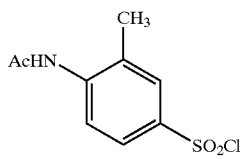
3

Sulfonic acid salt 2 (42.34 g, 169 mmol) and DMF (300 mL) were added to a flask that was equipped with a stir bar and nitrogen on demand and was cooled to 0° C. Thionyl chloride (30 mL, 411 mmol) was added dropwise from an addition funnel at a rate such that the temperature of the reaction mixture did not exceed 10° C. When the addition was complete, the mixture was allowed to warm to rt and stir for an additional 2½ h, after which time it was poured into a beaker containing crushed ice. The resulting solid was collected by filtration, washed with several portions of water and dried under vacuum (25.63 g, 61%). $^1$H NMR (DMSO, $d_6$, 400 MHz) δ 2.02 (s, 3H), 2.15 (s, 3H), 7.33 (s, 2H), 7.38 (s, 1H), 9.27 (s, 1H).

Step D:

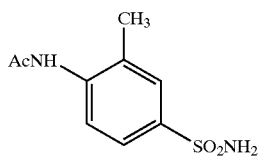
4

Into a round-bottom flask, equipped with a stir bar and nitrogen on demand, were placed sodium acetate (19.82 g, 241.6 mmol) and ethyl alcohol (200 mL) and the mixture was cooled to 0° C. Ammonia gas was bubbled through the sodium acetate solution for 5 min, then sulfonyl chloride 3 (25.63 g, 103 mmol) was added as a solid and in one portion. The resulting mixture was allowed to stir at 0° C. for 30 min, and was then allowed to warm to rt and stir for an additional 18 h. The mixture was then diluted with water and was poured into a separatory funnel containing water and ethyl acetate. The organic layer was collected, washed with water, brine, dried over MgSO$_4$, filtered and the solvents were removed under reduced pressure to provide 4 as a yellow solid (8.4 g, 36%), which was used without further purification.

Step E:

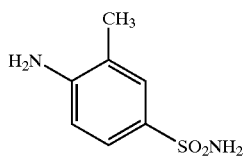
5

A round-bottom flask was equipped with a stir bar, a reflux condenser and nitrogen on demand. Into the flask were placed sulfonamide 4 (8.4 g, 36.80 mmol), ethyl alcohol (200 mL) and 2N hydrochloric acid (128 mL). The resulting mixture was allowed to heat to reflux overnight, after which time it was allowed to cool to RT and was neutralized with saturated, aqueous sodium bicarbonate. It was then poured into a separatory funnel containing water and ethyl acetate, the organic layer was collected, washed with water, brine, dried over MgSO$_4$, filtered and the solvents were removed under reduced pressure to afford a tan solid (6.35 g, 93%), which was used without further purification. $^1$H NMR (DMSO-$d_6$, 400 MHz) δ 2.06 (s, 3H), 5.54 (s, 2H), 6.58 (d, J=12 Hz, 1H), 6.82 (s, 2H), 7.30 (d, J=12 Hz, 1H), 7.33 (s, 1H).

Step F:

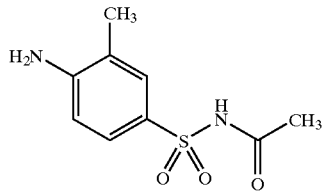
6

A solution of 4-amino-3-methylbenzenesulfonamide (5) (1 g, 5.4 mmol) in fuming sulfuric acid (5 mL) was cooled in ice/H$_2$O bath. Acetic acid (0.3 mL, 5.4 mmol) was added dropwise. The resultant mixture was gradually brought to room temperature and stirred for 3 hours. The mixture was poured into ice/H$_2$O and extracted with ethyl acetate. The ethyl acetate solution was washed with water, dried (MgSO$_4$) and concentrated to give 6 (0.13 g, 10%) as an off-white solid.

Step G:

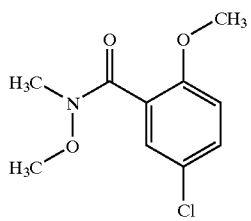
7

5-Chloro-2-methoxybenzoic acid (Aldrich, 17.1 g, 91 mmol), oxalyl chloride (50 mL of 2.0 M solution in dichloromethane, 100 mmol), DMF (1.2 mL), and dichloromethane (100 mL), were used to prepare the acid chloride according to general procedure V. The mixture was concentrated after 2 h, dissolved in chloroform (50 mL), and added dropwise to a solution of N,O-dimethylhydroxylamine (Aldrich, 13.34 g, 140 mmol), chloroform (200 mL), and triethylamine (19.06 mL, 140 mmol) at 0° C. as in general procedure VII. After 1 h, water was added to the reaction mixture and the organic layer was separated. The aqueous was further extracted with ethyl acetate. The organic layers were combined, dried over MgSO$_4$, filtered and the solvents were removed under reduced pressure to afford 3 (18.69 g, 96%). $^1$H NMR (DMSO-$d_6$, 300 MHz) δ 3.2 (bs, 3H), 3.45 (bs, 3H), 3.77 (s, 3H), 7.1 (d, 1H), 7.3 (d, 1H), 7.42 (m, 1H).

Step H:

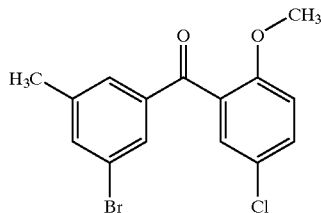
8

Into a oven dried round-bottom flask equipped with a stir bar, nitrogen on demand, and an addition funnel, were added 3,5-dibromotoluene (Avocado, 20.85 g, 83.4 mmol), and methyl t-butyl ether (500 mL) and the mixture was cooled to −50° C. by means of an acetonitrile dry ice bath. n-Butyllithium (57.4 mL of a 1.6 M solution in hexanes, 91.8 mmol) was added dropwise to the reaction and the mixture was allowed to stir for 30 min at −50° C. Weinreb amide 7 (19.16 g, 83.4 mmol) was added portion-wise via a powder addition funnel. The mixture was allowed to stir at −50° C., then warm to rt overnight. When judged to be complete, the reaction was poured into saturated ammonium chloride (500 mL) and stirred vigorously for 30 min. The mixture was then added to a separatory funnel. The organics were collected, washed with water, brine, dried over MgSO$_4$, filtered, and concentrated in vacuo to give a yellow solid (28.64 g) that was pulverized, then triturated with methanol and filtered to give 8 as a pale yellow solid (19.2 g, 68%). $^1$H NMR (DMSO-d$_6$, 400 MHz) δ 2.29 (s, 3H), 3.63 (s, 3H), 7.18 (d, 1H), 7.36 (d, 1H), 7.42 (s, 1H), 7.55 (m, 2H), 7.66 (s, 1H).

Step I:

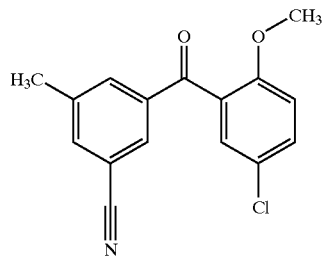

9

Into a oven dried round-bottom flask equipped with a stir bar, nitrogen on demand, and a reflux condenser, were added 8 (4.02 g, 12 mmol), sodium cyanide (1.16 g, 24 mmol), copper iodide (0.26 g, 1.4 mmol), and propionitrile (50 mL degassed with nitrogen for 30 min). To this mixture was added Pd(PPh$_3$)$_4$ (Strem, 1.37 g, 1.2 mmol) that had been triturated with methanol and filtered prior to addition. The mixture was heated to reflux and allowed to stir for 30 min. The mixture was cooled to rt and ethyl acetate (100 mL) was added. The resulting suspension was filtered through celite and the solids washed with ethyl acetate. The filtrate was washed with water, brine, dried over MgSO$_4$, filtered, and concentrated in vacuo. The resulting product was further purified by flash chromatography using 4:1 hexanes:ethyl acetate to afford 9 as an off-white solid (3.33 g, 99%). $^1$H NMR (DMSO-d$_6$, 300 MHz) δ 2.44 (s, 3H), 3.69 (s, 3H), 7.26 (d, 1H), 7.46 (d, 1H), 7.66 (dd, 1H), 7.86 (d, 2H), 7.99 (s, 1H).

Step J:

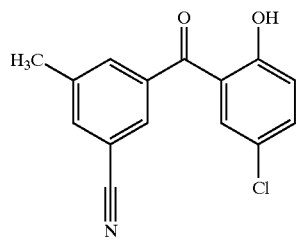

10

Anisole derivative 9 (3.27 g, 14.2 mmol), dichloromethane (45 mL), and boron tribromide (1.41 mL in 15 mL of dichloromethane) were combined as described in general procedure IX. The reaction was stirred at −78° C. for 1 h then allowed to warm to rt and stir for an additional 4 h. The reaction was then poured into ice water (500 mL) and stirred for additional 45 min, and poured into a separatory funnel. The organic layers were collected and washed with water, brine, and dried over MgSO$_4$, filtered, and concentrated in vacuo to give a yellow solid (5.62 g). The resulting solid that was recrystallized from methanol and filtered to give 10 as pale yellow crystals (2.65 g, 85%). $^1$H NMR (DMSO-d$_6$, 400 MHz) δ 2.4 (s, 3H), 6.98 (d, 1H), 7.37 (d, 1H), 7.47 (dd, 1H), 7.82 (d, 1H), 7.87 (s, 1H), 7.93 (d, 1H), 10.43 (s, 1H).

Step K:

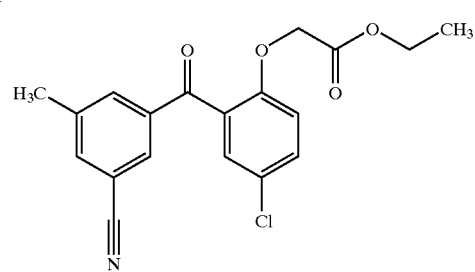

11

Compound 10 (2 g, 7.4 mmol), potassium carbonate (5.11 g, 37 mmol), ethyl bromoacetate (1 mL, 9 mmol), and acetone (40 mL) were used as in general procedure II to afford 11 as a yellow/off-white solid (2.73 g, crude material). $^1$H NMR (DMSO-d$_6$, 400 MHz) δ 1.14 (t, 3H), 2.39 (s, 3H), 4.08 (m, 2H), 4.78 (s, 2H), 7.14 (d, 1H), 7.47 (d, 1H), 7.58 (d, 1H), 7.9 (m, 3H).

Step L:

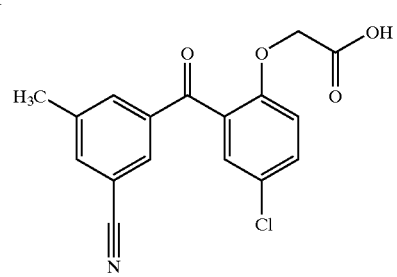

12

Ester 11 (2.73 g, 7.6 mmol), ethanol (EtOH, 20 mL), water (5 mL), and lithium hydroxide monohydrate (0.45 g, 10.7 mmol) were used as in general procedure III to afford 12 as an orange glass (2.45 g, 97%). $^1$H NMR (DMSO-d$_6$, 300 MHz) δ 2.3 (s, 3H), 4.67 (s, 2H), 7.1 (d, 1H), 7.44 (d, 1H), 7.58 (dd, 1H), 7.9 (m, 3H), 13.1 (bs, 1H).

Step M:

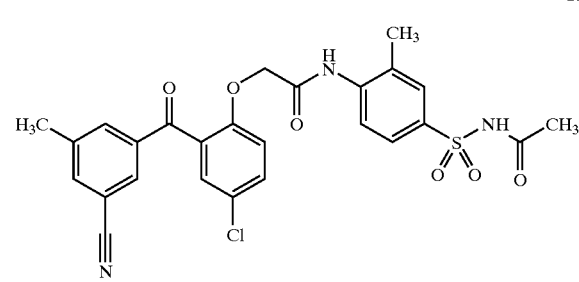

13

A mixture of 12 (0.22 g, 0.7 mmol) and 5 mL of thionyl chloride in methylene chloride was refluxed for 1 hour. The reaction mixture was concentrated and to the concentrate was added sodium bicarbonate, and 6 in acetone and the mixture was stirred overnight. EtOAc was added, which was followed by washings with water and brine. After drying and solvent removal, the crude product was purified by flash column chromatography on silica with 2% MeOH in methylene chloride as the eluant. This gave 13 (0.11 g, 31%) as a white solid. $^1$H NMR (DMSO-d$_6$, 300 MHz) δ 1.9 (s, 3H), 2.2 (s, 3H), 2.4 (s, 3H), 4.8 (s, 2H), 7.2 (d, 1H), 7.5 (s, 1H), 7.6–7.8 (m, 4H), 7.8–8 (m, 3H), 9.4 (s, 1H), 12 (s, 1H).

Step N:

One equivalent of NaOH was added to 13 (0.11 g, 0.2 mmol) in water (5 mL). Following lyophilization, 1 was obtained as a white fluffy solid (0.11 g, 100%). $^1$H NMR (DMSO-d$_6$, 300 MHz) δ 1.9 (s, 3H), 2.2 (s, 3H), 2.4 (s, 3H), 4.8 (s, 2H), 7.2 (d, 1H), 7.5 (s, 1H), 7.6–7.8 (m, 4H), 7.8–8 (m, 3H), 9.4 (s, 1H).

EXAMPLE 2

2-[4-chloro-2-(3-cyano-5-methylbenzoyl)phenoxy]-N-{4-[(isobutyrylamino)sulfonyl]-2-methylphenyl}acetamide, Sodium Salt

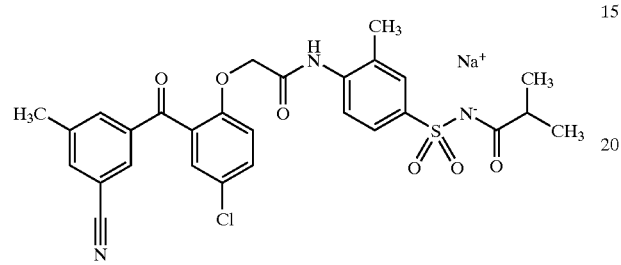

14

Step A:

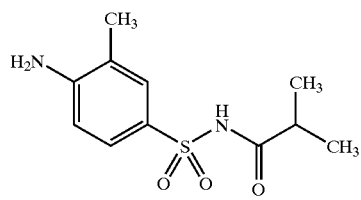

15

Following the procedure for the synthesis of 6 and using 12 (1 g, 5.4 mmol), isobutyric acid (0.6 mL, 5.9 mL) and fuming sulfuric acid (5 mL), 15 (0.67 g, 48%) was obtained as an off-white solid.

Step B:

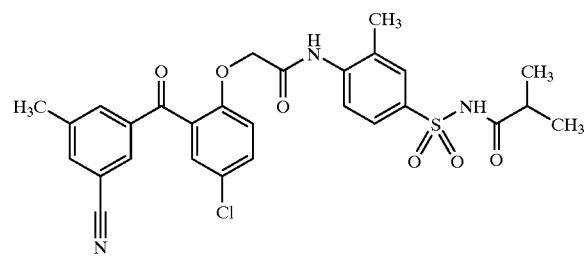

16

Following the procedure for the synthesis of 13 and using 15 (0.2 g, 0.6 mmol), 16 (0.12 g, 33%) was obtained as a white solid. $^1$H NMR (DMSO-d$_6$, 300 MHz) δ 1.9 (d, 6H), 2.2 (s, 3H), 2.4 (s, 3H), 2.3–2.5 (m, 1H), 4.8 (s, 2H), 7.2 (d, 1H), 7.5 (s, 1H), 7.6–7.8 (m, 4H), 7.8–8 (m, 3H), 9.4 (s, 1H), 12 (s, 67 (s, 2H).

Step C:

Following the procedure used for the synthesis of 1 and using 16 (0.12 g, 0.2 mmol) and 1 equivalent of NaOH, 14 (0.13 g, 100%) was obtained as a white fluffy solid. $^1$H NMR (DMSO-d$_6$, 300 MHz) δ 1.9 (d, 6H), 2.2 (s, 3H), 2.4 (s, 3H), 2.3–2.5 (m, 1H), 4.8 (s, 2H), 7.2 (d, 1H), 7.5 (s, 1H), 7.6–7.8 (m, 4H), 7.8–8 (m, 3H), 9.4 (s, 1H).

EXAMPLE 3

2-[4-chloro-2-(3-cyano-5-methylbenzoyl)phenoxy]-N-{2-methyl-4-[(propionylamino)sulfonyl]phenyl}acetamide, Sodium Salt

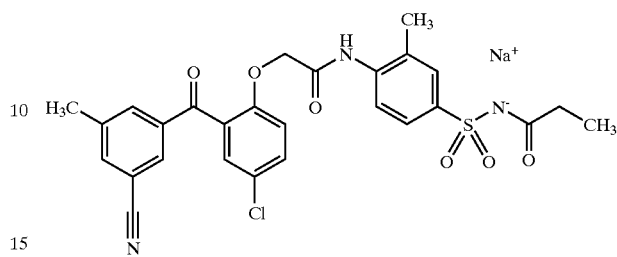

17

Step A:

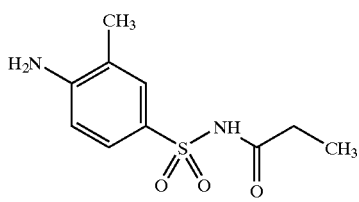

18

Propionic acid (Aldrich, 1.87 mL, 25 mmol) was added dropwise to fuming sulfuric acid (5 mL) in a round bottomed flask cooled in a water bath. The solution was stirred for 1 h at rt then 4-amino-3-methylbenzenesulfonamide (5) (3.26 g, 17.4 mmol) was added in one portion. The reaction was heated to 40° C. and stirred for an additional 4 h. The syrup was poured into ice water and the pH was adjusted to 4–5 with concentrated ammonium hydroxide. The resulting suspension was stirred vigorously for 2 h. The suspension was filtered and the solid was farther purified on silica gel by flash chromatography using 95:5 methylene chloride (CH$_2$Cl$_2$): methanol (CH$_3$OH) as eluant to afford an orange oil (1.86 g, crude). The crude oil was triturated with diethyl ether and the resulting solid was filtered and air-dried to afford 18 as a pale yellow solid (1.46 g, 34%). $^1$H NMR (DMSO-d$_6$, 300 MHz) δ 11.53 (s, 1H), 7.41 (m, 2H), 6.63 (m, 1H), 5.87 (s, 2H), 2.14 (q, 2H), 2.06 (s, 3H), 0.86 (t, 3H). LC-MS (ES$^+$) m/z 243 (M+H)$^+$, LC-MS (ES$^-$) m/z 241 (M−H)$^-$.

Step B:

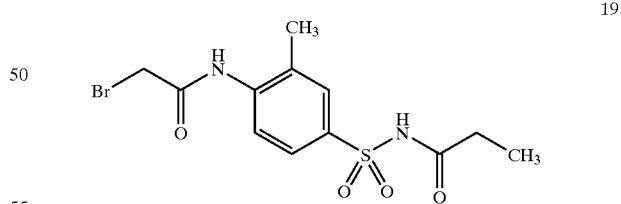

19

Sulfonamide 18 (1.46 g, 6 mmol), THF (100 mL), and triethylamine (0.92 mL, 6.6 mmol) were combined and cooled to 0° C. Bromoacetyl bromide (1.15 mL, 13.2 mmol) was added dropwise and the solution was stirred and slowly warmed to rt over 12 h. An additional amount of bromoacetyl bromide (2.09 mL, 24 mmol) was added dropwise to the solution at 0° C. The reaction was stirred for 2 h at 0° C., then the reaction was diluted with water (150 mL) and extracted with ethyl acetate (ethyl acetate). The organic layers were washed with a 1:1:1 water: saturated sodium bicarbonate: brine solution, then dried over MgSO$_4$, filtered and concentrated in vacuo to afford an orange oil. The oil was triturated with diethyl ether and the resulting solid was filtered and washed with diethyl ether. The solid was dried under a stream of nitrogen to afford 19 as a tan solid (1.96 g, 90%). $^1$H NMR (DMSO-d$_6$, 300 MHz) δ 11.97 (bs, 1H), 9.90 (s, 1H), 7.69–7.81 (m, 3H), 4.15 (s, 2H), 2.31 (s, 3H), 2.21 (q, 2H), 0.88 (t, 3H). LC-MS (AP$^+$) m/z 363 (M+)$^+$, m/z 365 (M+)$^+$, LC-MS (AP$^-$) m/z 362 (M–)$^-$, m/z 364 (M–)$^-$.

Step C:

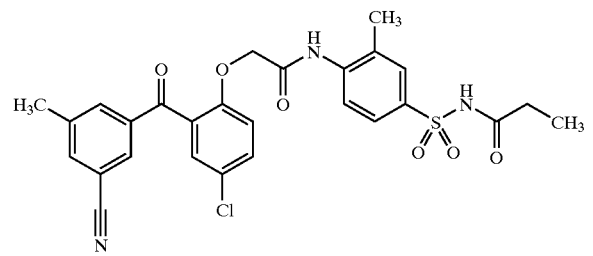

20

Phenol 10 (0.78 g, 2.9 mmol) and DMF (11 mL) were combined with sodium hydride (Aldrich, 0.17 g as a 60% dispersion in mineral oil, 4.3 mmol) slowly at rt. The reaction was stirred for 10 min. then sulfonamide 19 (1 g, 2.8 mmol) was added portion-wise. After 12 h, the reaction was heated to 45° C. and stirred under nitrogen. After 2 h, the reaction was cooled to rt, poured into ice water, and the pH was adjusted to 4 with 1N HCl. The solution was extracted with ethyl acetate (3×), the aqueous was filtered, and the resulting solid was washed with water and diethyl ether The product was then purified on silica gel by flash chromatography using 95:5 CH$_2$Cl$_2$:CH$_3$OH as eluant to afford 20 as a tan solid (0.097 g, 6%). $^1$H NMR (DMSO-d$_6$, 300 MHz) δ 11.94 (s, 1H), 9.39 (s, 1H), 7.97 (s, 1H), 7.93 (s, 1H), 7.89 (s, 1H), 7.49–7.78 (m, 6H), 7.22 (d, 1H), 4.82 (s, 2H), 2.36 (s, 3H), 2.16–2.24 (m, 4H), 0.87 (t, 3H). LC-MS (AP$^+$) m/z 554 (M+H)$^+$, m/z 576 (M+Na)$^+$, LC-MS (AP$^-$) m/z 552 (M–H)$^-$.

Step D:

Compound 20 (0.077 g, 0.139 mmol) was combined with 1 N NaOH (0.154 mL, 0.154 mmol) then water was added until the solid dissolved. The resulting solution was lyophilized to afford 17 as an off-white solid (0.075 g, 94%). $^1$H NMR (DMSO-d$_6$, 300 MHz) δ 9.20 (s, 1H), 7.97 (s, 1H), 7.93 (s, 1H), 7.91 (s, 1H), 7.45–7.67 (m, 5H), 7.35 (d, 1H), 7.22 (d, 1H), 4.77 (s, 2H), 2.36 (s, 2H), 2.08 (s, 3H), 1.87 (q, 2H), 0.82 (t, 3H).

EXAMPLE 4

2-[4-chloro-2-(3-cyano-5-methylbenzoyl)phenoxy]-N-(2-methyl-4-{(1-pyrrolidinylacetyl)amino]sulfonyl}phenyl)acetamide, Sodium Salt

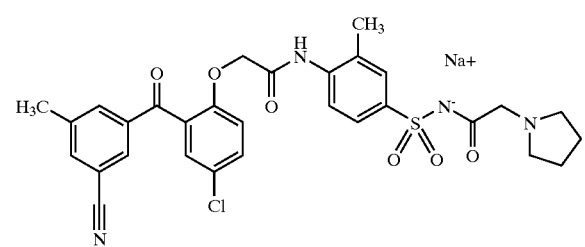

21

Step A:

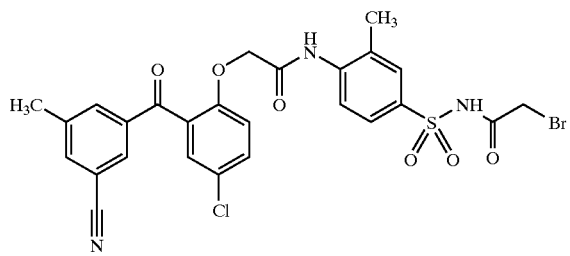

22

A mixture of N-[4-(aminosulfonyl)-2-methylphenyl]-2-[4-chloro-2-(3-cyano-5-methylbenzoyl)phenoxy]acetamide (0.5 g, 1 mmol) and DMAP (0.125 g, 1 mmol) in 10 mL of CH$_2$Cl$_2$ was cooled to 0° C. Bromoacetic acid anhydride (Lancaster, 0.56 mL of 65% w/v solution in acetonitrile, 1.4 mmol) was added dropwise. The reaction was then brought to reflux under nitrogen. After 4 h, the reaction was cooled to rt, washed with 1 N HCl, water, and brine, then dried over MgSO$_4$, filtered, and concentrated in vacuo. The product was then purified on silica gel by chromatography using 9:1 CH$_2$Cl$_2$:CH$_3$OH as eluant to afford 22 as a yellow glass (0.48 g, 77%). $^1$H NMR (DMSO-d$_6$, 300 MHz) δ 9.36 (s, 1H), 7.97 (s, 1H), 7.93 (s, 1H), 7.89 (s, 1H), 7.62–7.71 (m, 4H), 7.49 (d, 1H), 7.22 (d, 1H), 4.81 (s, 2H), 3.86 (s, 2H), 2.37 (s, 3H) 2.18 (s, 3H); LC-MS (AP$^+$) m/z 618 (M+)$^+$.

Step B:

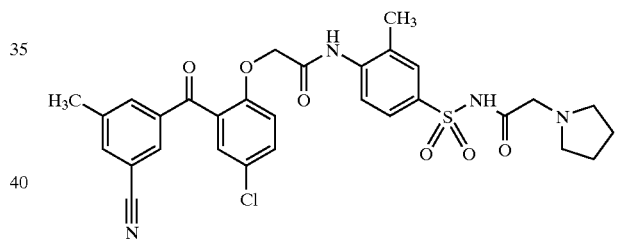

23

A mixture of 22 (0.075 g, 0.12 mmol), sodium iodide (0.005 g, 0.03 mmol), and pyrrolidine (Aldrich, 0.011 mL, 0.13 mmol) in 2 mL of THF was stirred at room temperature for 15 h. The suspension was dissolved in CH$_2$Cl$_2$ and chromatographed by TLC prep plate eluted with 9:1 CH$_2$Cl$_2$:MeOH to afford 23 as a white solid (0.028 g, 37%). $^1$H NMR (CDCl$_3$, 400 MHz) δ 8.55 (s, 1H), 7.96 (d, 1H), 7.81–7.87 (m, 3H), 7.66 (s, 1H), 7.55 (dd, 1H), 7.32 (d, 1H), 7.04 (d, 1H), 4.68 (s, 2H), 3.74 (s, 2H), 3.25 (bs, 4H), 2.44 (s, 3H), 2.25 (s, 3H), 2.02 (m, 4H); LC-MS (ES$^+$) m/z 609 (M+H)$^+$, LC-MS (ES$^-$) m/z 608 (M–H)$^-$.

Step C:

Benzophenone 23 (0.028 g, 0.046 mmol) was combined with 1 N NaOH (0.098 mL, 0.098 mmol) then water was added until the solid dissolved. The resulting solution was lyophilized to afford 21 as an off-white solid (0.028 g, 93%). $^1$H NMR (DMSO-d$_6$, 300 MHz) δ 9.21 (s, 1H), 7.97 (s, 1H), 7.93 (s, 1H), 7.90 (s, 1H), 7.64 (dd, 1H), 7.35–7.52 (m, 4H), 7.22 (d, 1H), 4.76 (s, 2H), 3.21 (s, 4H), 2.81 (s, 2H), 2.36 (s, 3H), 2.09 (s, 3H), 1.58 (m, 4H); LC-MS (ES$^+$) m/z 609 (M+H)$^+$, m/z 631 (M+Na)$^+$, LC-MS (ES$^-$) m/z 607 (M–H)$^-$

EXAMPLE 5

2-[4-chloro-2-(3-cyano-5-methylbenzoyl)phenoxy]-
N-(2-methyl-4-{[(1-piperidinylacetyl)amino]
sulfonyl}phenyl)acetamide, Sodium Salt

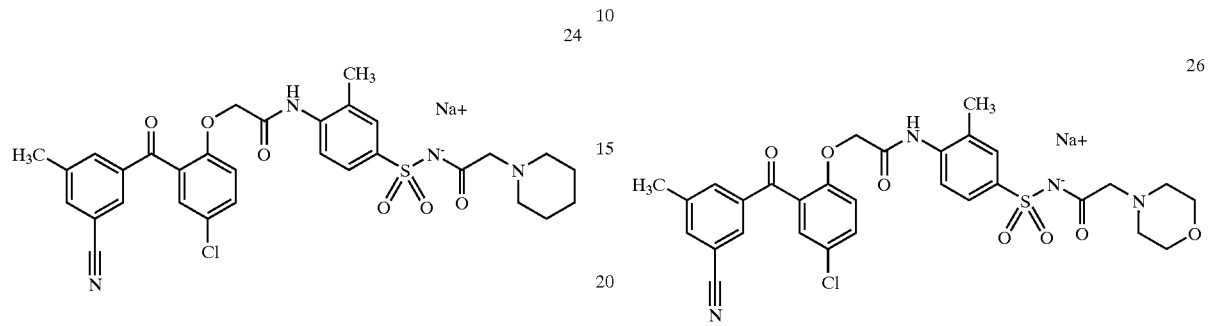

Step A:

A mixture of 22 (0.1 g, 0.16 mmol), sodium iodide (0.005 g, 0.03 mmol), and piperidine (Applied Biosystems, 0.018 mL, 0.18 mmol) in 2 mL of $CH_2Cl_2$ was stirred at room temperature for 6 d. The reaction was then loaded onto a TLC prep plate eluted with 9:2 $CH_2Cl_2$:MeOH to afford a white solid. The solid was dissolved again in $CH_2Cl_2$ and further purified by TLC prep plate eluted with 9:1 $CH_2Cl_2$:MeOH to afford 25 as a white solid (0.028 g, 28%). $^1$H NMR (CDCl$_3$, 300 MHz) δ 8.57 (s, 1H), 8.01 (d, 1H), 7.88 (s, 1H), 7.86 (s, 1H), 7.82 (s, 1H), 7.67 (s, 1H), 7.55 (dd, 1H), 7.32 (d, 1H), 7.04 (d, 1H), 4.69 (s, 2H), 3.32 (s, 2H), 2.83 (m, 4H), 2.45 (s, 3H), 2.26 (s, 3H), 1.76 (m, 4H), 1.52 (m, 2H); LC-MS (ES$^+$) m/z 623 (M+H)$^+$, m/z 645 (M+Na)$^+$, LC-MS (ES$^-$) m/z 621 (M−H)$^-$.

Step B:

Benzophenone 25 (0.028 g, 0.045 mmol) was combined with 1 N NaOH (0.050 mL, 0.050 mmol) then water was added until the solid dissolved. The resulting solution was lyophilized to afford 24 as an off-white solid (0.029 g, 99%). $^1$H NMR (CDCl$_3$, 300 MHz) δ 8.55 (s, 1H), 7.97 (d, 1H), 7.88 (s, 1H), 7.84 (m, 1H), 7.80 (s, 1H), 7.65 (s, 1H), 7.53 (dd, 1H), 7.31 (d, 1H), 7.02 (d, 1H), 4.67 (s, 2H), 3.12 (s, 2H), 2.66 (m, 2H), 2.43 (s, 3H), 2.24 (s, 3H), 1.66 (m, 4H), 1.47 (m, 2H), 1.21 (s, 2H).

EXAMPLE 6

2-[4-chloro-2-(3-cyano-5-methylbenzoyl)phenoxy]-
N-(2-methyl-4-{[(4-morpholinylacetyl)amino]
sulfonyl}phenyl)acetamide, Sodium Salt

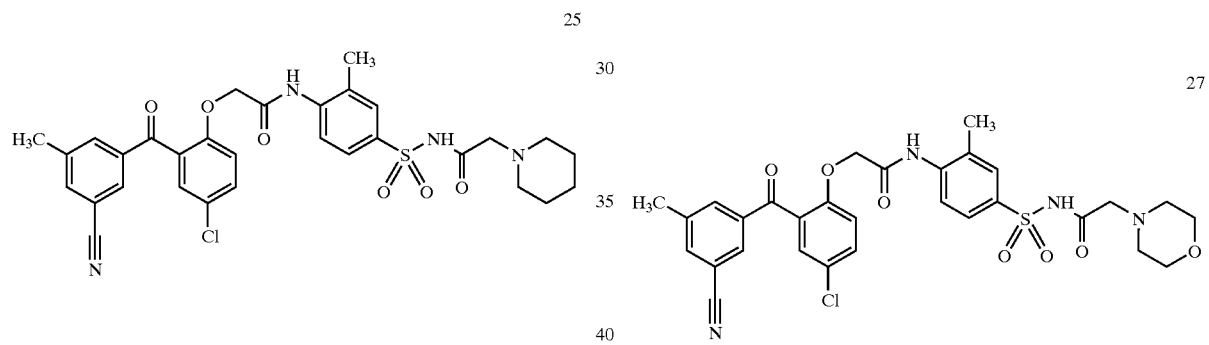

Step A:

A mixture of 22 (0.1 g, 0.16 mmol), sodium iodide (0.005 g, 0.03 mmol), and morpholine (Aldrich, 0.016 mL, 0.18 mmol) in 2 mL of $CH_2Cl_2$ was stirred at room temperature for 15 h. The suspension was dissolved in $CH_2Cl_2$ and chromatographed by on silica gel using 9:2 $CH_2Cl_2$:MeOH to afford 27 as a white solid (0.041 g, 41%). $^1$H NMR (DMSO-d$_6$, 300 MHz) δ 9.31 (s, 1H), 7.97 (s, 1H), 7.92 (m, 2H), 7.55–7.67 (m, 3H), 7.44–7.49 (m, 3H), 7.22 (d, 1H), 4.78 (s, 2H), 3.70 (m, 4H), 3.47 (s, 2H), 2.97 (m, 4H), 2.37 (s, 3H), 2.12 (m, 4H).

Step B:

Benzophenone 27 (0.04 g, 0.064 mmol) was combined with 1 N NaOH (0.072 mL, 0.072 mmol) then water was added until the solid dissolved. The resulting solution was lyophilized to afford 26 as an off-white solid (0.04 g, 98%). $^1$H NMR (CDCl$_3$, 400 MHz) δ 8.61 (s, 1H), 8.04 (d, 1H), 7.86 (s, 1H), 7.83 (s, 1H), 7.68–7.75 (m, 3H), 7.55 (dd, 1H), 7.31 (d, 1H), 7.04 (d, 1H), 4.7 (s, 2H), 3.77 (m, 4H), 2.47 (s, 3H), 2.28 (s, 3H), 1.57 (s, 6H); LC-MS (ES$^+$) m/z 625 (M+H)$^+$, m/z 647 (M+Na)$^+$, LC-MS (ES$^-$) m/z 623 (M−H)$^-$.

EXAMPLE 7

2-{4-chloro-2-[3-cyano-5-(trifluoromethyl)benzoyl]phenoxy}-N-{2-methyl-4-[(propionylamino)sulfonyl]phenyl}acetamide, Sodium Salt

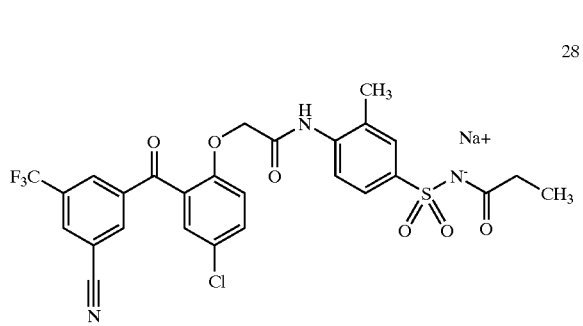

28

Step A:

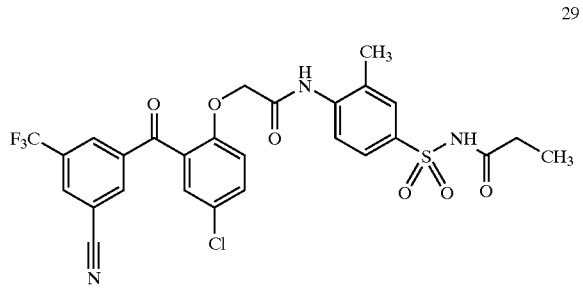

29

Propionic anhydride (Lancaster, 0.021 mL, 0.16 mmol) was added dropwise to a mixture of 58 (0.08 g, 0.15 mmol) and DMAP (0.018 g, 0.15 mmol) in 4 mL of $CH_2Cl_2$ and the resulting solution was brought to reflux. After 2.5 h, the reaction was then cooled to rt, washed with 1 N HCl and the organics were concentrated in vacuo. The product was then purified by TLC prep plate eluted with 1:1 EtOAc: Hexanes to afford 29 as a white solid (0.07 g, 80%). $^1$H NMR (CDCl$_3$, 300 MHz) δ 8.64 (s, 1H), 8.12 (d, 2H), 7.97 (s, 1H), 7.85 (d, 1H), 7.60–7.68 (m, 2H), 7.42 (dd, 1H), 7.22 (d, 1H), 6.93 (d, 1H), 4.56 (s, 2H), 2.13 (s, 3H), 2.06 (q, 2H), 0.83 (t, 3H); LC-MS (ES$^+$) m/z 608 (M+H)$^+$, 630 (M+Na); (ES$^-$) m/z 606 (M–H)$^-$.

Step B:

Benzophenone 29 (0.07 g, 0.115 mmol) was combined with 1 N NaOH (0.127 mL, 0.127 mmol) then water was added until the solid dissolved. The resulting solution was lyophilized to afford 28 as an off-white solid (0.053 g, 73%). $^1$H NMR (DMSO-d$_6$, 300 MHz) δ 9.33 (s, 1H), 8.49 (s, 1H), 8.32 (s, 1H), 7.69 (dd, 1H), 7.44–7.56 (m, 3H), 7.34 (d, 1H), 7.23 (d, 1H), 4.77 (s, 2H), 2.09 (s, 3H), 1.87 (q, 2H), 0.82 (t, 3H); LC-MS (ES$^+$) m/z 629 (M+)$^+$.

EXAMPLE 8

2-{4-chloro-2-[3-cyano-5-(trifluoromethyl)benzoyl]phenoxy}-N-[4-[(isobutyrylamino)sulfonyl]-2-methylphenyl]acetamide, Sodium Salt

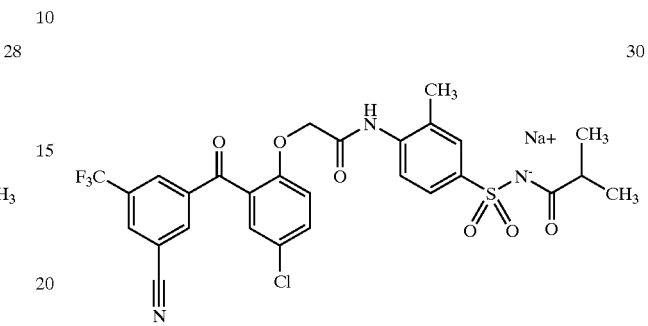

30

Step A:

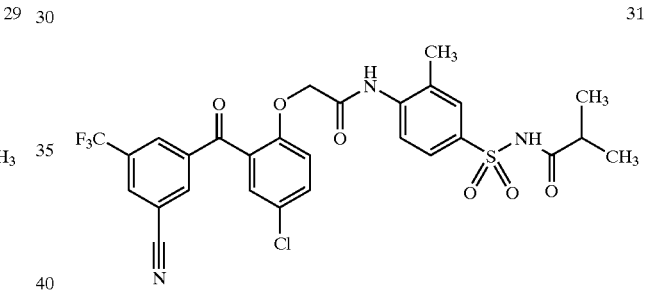

31

Isobutyric anhydride (Aldrich, 0.027 mL, 0.16 mmol) was added dropwise to a mixture of 58 (0.08 g, 0.15 mmol) and DMAP (0.018 g, 0.15 mmol) in 4 mL of $CH_2Cl_2$ and the resulting solution was brought to reflux. After 2.5 h, the reaction was then cooled to rt, washed with 1 N HCl and the organics were concentrated in vacuo. The product was then purified by TLC prep plate eluted with 1:1 ethyl acetate: hexanes to afford 31 as a white solid (0.06 g, 67%). $^1$H NMR (DMSO-d$_6$, 300 MHz) δ 9.45 (s, 1H), 8.60 (s, 1H), 8.49 (s, 1H), 8.31 (s, 1H), 7.56–7.71 (m, 5H), 7.23 (d, 1H), 4.81 (s, 2H), 2.38 (m, 1H), 2.18 (s, 3H), 0.92 (s, 3H), 0.90 (s, 3H); LC-MS (ES$^+$) m/z 622 (M+H)$^+$, 644 (M+Na); (ES$^-$) m/z 620 (M–H)$^-$.

Step B;

Benzophenone 31 (0.06 g, 0.097 mmol) was combined with 1 N NaOH (0.106 mL, 0.106 mmol) then water was added until the solid dissolved. The resulting solution was lyophilized to afford 30 as an off-white solid (0.052 g, 84%). $^1$H NMR (DMSO-d$_6$, 300 MHz) δ 9.34 (s, 1H), 8.63 (s, 1H), 8.49 (s, 1H), 8.32 (s, 1H), 7.69 (dd, 1H), 7.43–7.57 (m, 3H), 7.34 (d, 1H), 7.23 (d, 1H), 4.77 (s, 2H), 2.08 (s, 3H), 0.88 (s, 3H), 0.85 (s, 3H); LC-MS (AP$^+$) m/z 644 (M+Na)$^+$.

EXAMPLE 9

2-{4-chloro-2-[3-cyano-5-(trifluoromethyl)benzoyl]phenoxy}-N-(2-methyl-4-{[(3-methylbutanoyl)amino]sulfonyl}phenyl)acetamide, Sodium Salt

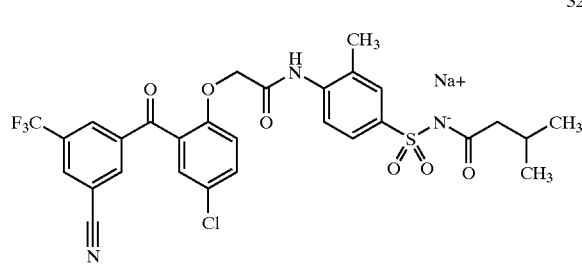
32

Step A:

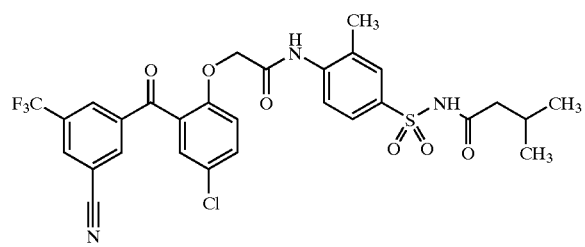
33

Isovaleric anhydride (TCI, 0.031 mL, 0.16 mmol) was added dropwise to a mixture of 58 (0.08 g, 0.15 mmol) and DMAP (0.018 g, 0.15 mmol) in 4 mL of CH$_2$Cl$_2$ and the resulting solution was brought to reflux. After 2.5 h, the reaction was then cooled to rt, washed with 1 N HCl and the organics were concentrated in vacuo. The product was then purified by TLC prep plate eluted with 1:1 ethyl acetate:hexanes to afford 33 as a white solid (0.06 g, 65%). $^1$H NMR (DMSO-d$_6$, 300 MHz) δ 11.95 (bs, 1H), 9.48 (s, 1H), 8.60 (s, 1H), 8.49 (s, 1H), 8.32 (s, 1H), 7.6–7.75 (m, 4H), 7.57 (d, 1H), 7.23 (d, 1H), 4.82 (s, 2H), 2.20 (s, 3H), 2.03 (d, 2H), 1.86 (m, 1H), 0.77 (t, 3H), 0.75 (t, 3H); LC-MS (ES$^+$) m/z 636 (M+H)$^+$, 658 (M+Na); (ES$^-$) m/z 634 (M–H)$^-$.

Step B:

Compound 33 (0.06 g, 0.094 mmol) was combined with 1 N NaOH (0.104 mL, 0.104 mmol) then water was added until the solid dissolved. The resulting solution was lyophilized to afford 32 as an off-white solid (0.047 g, 76%). $^1$H NMR (DMSO-d$_6$, 300 MHz) δ 9.32 (s, 1H), 8.63 (s, 1H), 8.49 (s, 1H), 8.32 (s, 1H), 7.69 (dd, 1H), 7.4–7.6 (m, 3H), 7.34 (d, 1H), 7.23 (d, 1H), 4.77 (s, 2H), 2.08 (s, 3H), 1.84 (m, 1H), 1.74 (d, 2H), 0.77 (t, 3H), 0.75 (t, 3H); LC-MS (AP$^+$) m/z 658 (M+Na)$^+$, (ES$^+$) m/z 658 (M+Na)$^+$.

EXAMPLE 10

2-[4-chloro-2-(3-chloro-5-cyanobenzoyl)phenoxy]-N-(2-methyl-4-[[(propionylamino)sulfonyl]phenyl}acetamide, Sodium Salt

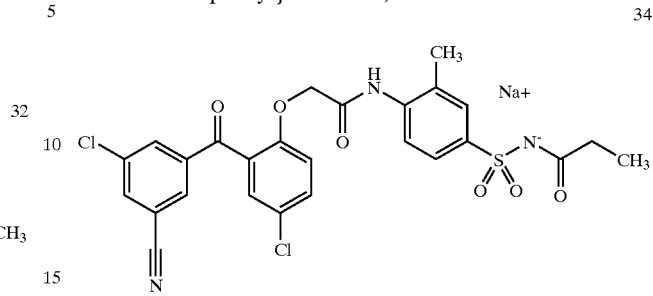
34

Step A:

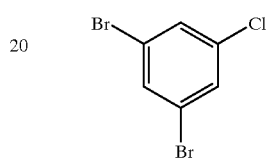
35

A solution of 1,3,5-tribromobenzene (9.44 g, 30 mmol) in 120 mL of ether was cooled to −78° C. in a dry ice/acetone bath. n-Butyllithium (13.2 mL of 2.5 M solution in hexanes, 33 mmol) was added dropwise over 10 min. The resulting mixture was stirred at −78° C. for an additional 10 min, then hexachloroethane (7.15 g, 30.2 mmol) was added in small portions over 3 min. The reaction mixture was then stirred for 15 min at −78° C., followed by 3.2 h at rt. The mixture was partitioned between 100 mL of water and 100 mL of EtOAc. The aqueous layer was separated and extracted with an additional 100 mL of EtOAc. The combined organic layers were then dried over MgSO$_4$, filtered, and concentrated in vacuo to give 35 as a pale brown solid (7.72 g, 95%): $^1$H NMR (CDCl$_3$, 300 MHz) δ 7.57 (t, 1 H), 7.47 (d, 2H).

Step B:

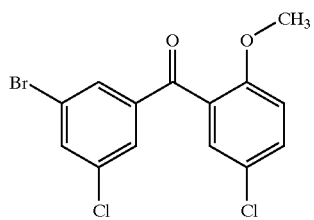
36

A solution of 35 (7.62 g, 28.2 mmol) in 100 mL of ether was cooled to −78° C. in a dry ice/acetone bath. n-Butyllithium (12.6 mL of 2.5 M solution in hexanes, 31.5 mmol) was added dropwise over 30 min. The resulting mixture was stirred at −78° C. for an additional 13 min, then 7 (6.57 g, 28.6 mmol) was added in small portions over 23 min. The reaction mixture was then stirred for 22 h as the bath was allowed to warm to room temperature. The mixture was poured into 100 mL water and extracted with two 100-mL portions of EtOAc. The combined organic layers were then dried over MgSO$_4$, filtered, and concentrated in vacuo to give 9.46 g of a beige solid. Recrystallization from hot MeOH gave 36 (6.45 g, 64%): MS (AP−) m/z 358 (M−H); $^1$H NMR (CDCl$_3$, 300 MHz) δ 7.76 (t, 1 H), 7.70 (t, 1 H), 7.65 (t, 1 H), 7.47 (dd, 1 H), 7.36 (d, 1 H), 6.95 (d, 1 H), 3.72 (s, 3 H).

Step C:

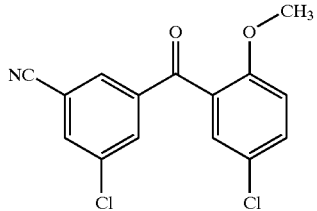

37

A solution of 36 (0.299 g, 0.83 mmol), sodium cyanide (0.086 g, 1.76 mmol), copper (I) iodide (0.028 g, 0.15 mmol), and tetrakis-(triphenylphosphine)-palladium (0.113 g, 0.10 mmol) in 8 mL of acetonitrile was heated to reflux for 40 min. The reaction mixture was then diluted with 50 mL of EtOAc and filtered through Celite. The resulting solution was washed with 25 mL of water, dried over $MgSO_4$, filtered and concentrated in vacuo to give 0.375 g of an orange gum. Purification by flash chromatography using 5% EtOAc/hexane as the eluant gave 37 (0.171 g, 56%): $^1$H NMR ($CDCl_3$, 400 MHz) δ 7.93 (t, 1H), 7.82 (t, 1 H), 7.76 (t, 1 H), 7.47 (dd, 1 H), 7.37 (d, 1 H), 6.93 (d, 1H), 3.67 (s, 3 H).

Step D:

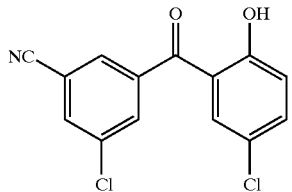

38

38 was prepared according to General Procedure IX from 37 (0.165 g, 0.54 mmol). The reaction gave 38 (0.174 g, 100%): $^1$H NMR ($CDCl_3$, 400 MHz) δ 11.43 (s, 1 H), 7.84–7.82 (m, 2 H), 7.78 (t, 1 H), 7.49 (dd, 1 H), 7.34 (d, 1 H), 7.05 (d, 1 H).

Step E:

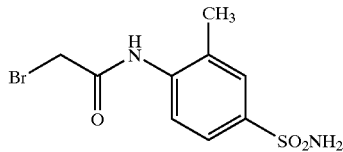

39

A solution of 4-amino-3-methylbenzenesulfonamide (5) (5.0 g, 26.85 mol) and pyridine (2.4 mL, 29.53 mmol) in 150 mL of chloroform was cooled to 0° C. in an ice bath. Bromoacetyl bromide (2.6 mL, 29.53 mmol) was added dropwise over 20 min, and the resulting mixture was allowed to slowly warm to room temperature as it was stirred for 18 h. The reaction mixture was then poured into 150 mL of water and extracted with two 100-mL portions of $CH_2Cl_2$. Both the organic and aqueous layers were filtered to yield a beige solid. This solid was suspended in 40 mL of 1 N HCl and stirred several minutes. The solid was then filtered and rinsed with $CH_2Cl_2$, MeOH, and hexanes to yield 39 (5.705 g, 69%): $^1$H NMR ($CDCl_3$, 400 MHz) δ 9.84 (s, 1H), 7.66–7.56 (m, 3H), 7.23 (br s, 2 H), 4.09 (s, 2 H), 2.24 (s, 3 H).

Step F:

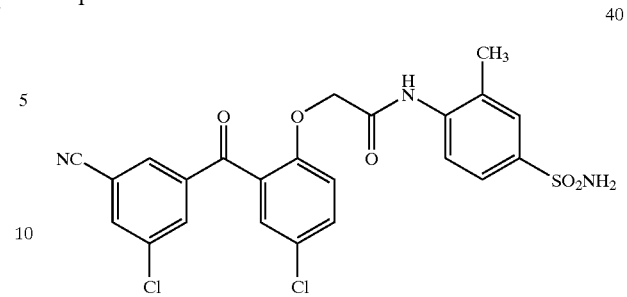

40

A mixture of 38 (0.157 g, 0.54 mmol), 39 (0.165 g, 0.54 mmol), and potassium carbonate (0.373 g, 2.7 mmol) in 10 mL of acetone was warmed to reflux for 17.5 h. The reaction mixture was then poured into 35 mL of water and extracted with two 35-mL portions of EtOAc. The combined organic layers were washed with brine, dried over $MgSO_4$, filtered, and concentrated in vacuo to give 0.276 g of a yellow oil. Purification by flash chromatography using 0.5–1% MeOH/ $CH_2Cl_2$ gave 40 (0.033 g, 12%): MS (AP–) m/z 517 (M–H); $^1$H NMR (DMSO-$d_6$, 400 MHz) δ 9.42 (s, 1 H), 8.26 (s, 1 H), 8.11 (s, 1 H), 8.03 (t, 1 H), 7.63 (dd, 1 H), 7.60–7.53 (m, 3 H), 7.49 (d, 1 H), 7.22 (s, 2 H), 7.19 (d, 1 H), 4.77 (s, 2 H), 2.14 (s, 3 H).

Step G:

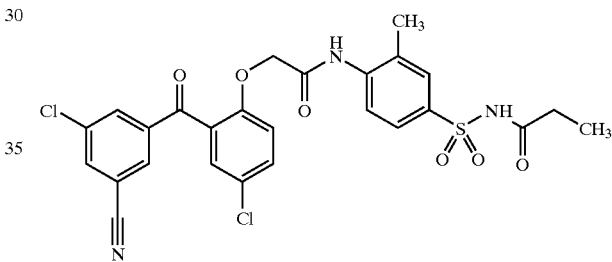

41

Propionic anhydride (Aldrich, 0.077 mL, 0.6 mmol) was added dropwise to a mixture of 40 (0.26 g, 0.5 mmol) and DMAP (0.061 g, 0.5 mmol) in 6 mL of $CH_2Cl_2$ and the resulting solution was brought to reflux. After 2.5 h, the reaction was then cooled to rt, washed with 1 N HCl and the organics were concentrated in vacuo. The product was then washed with diethyl ether to afford 41 as a white solid (0.027 g, 9.4%). The filtrate was concentrated and then purified by chromatography using 1:1 EtOAc: Hexanes as eluant to afford a white solid that was then further purified by TLC prep plate eluted with 1:1 EtOAc: Hexanes to afford 41 as a white solid (0.06 g, 20.8%). $^1$H NMR (DMSO-$d_6$, 300 MHz) δ 11.93 (bs, 1H), 9.44 (s, 1H), 8.28 (s, 1H), 8.15 (m, 1H), 7.62–7.69 (m, 4H), 7.53 (d, 1H), 7.22 (d, 1H), 4.82 (s, 2H), 2.20 (s, 3H), 2.13 (m, 2H), 0.86 (t, 3H); LC-MS ($ES^+$) m/z 574 (M+H)$^+$, ($ES^-$) m/z 572 (M–H)$^-$ Step H:

Benzophenone 41 (0.09 g, 0.157 mmol) was combined with 1 N NaOH (0.174 mL, 0.174 mmol) then water was added until the solid dissolved. The resulting solution was lyophilized to afford 34 as an off-white solid (0.085 g, 90%). $^1$H NMR (DMSO-d6, 300 MHz) δ 9.32 (s, 1H), 8.30 (s, 1H), 8.14 (s, 1H), 8.08 (s, 1H), 7.67 (dd, 1H), 7.46–7.53 (m, 3H), 7.36 (d, 1H), 7.22 (d, 1H), 4.78 (s, 2H), 2.10 (s, 3H), 1.88 (q, 2H), 0.83 (t, 3H); LC-MS ($AP^+$) m/z 596 (M+Na)$^+$, ($ES^+$) m/z 596 (M+Na)$^+$.

EXAMPLE 11

2-(14-chloro-2-(3-chloro-5-cyanobenzoyl)phenoxy]-N-{4-[(isobutyrylamino)sulfonyl]-2-methylphenyl}acetamide, Sodium Salt

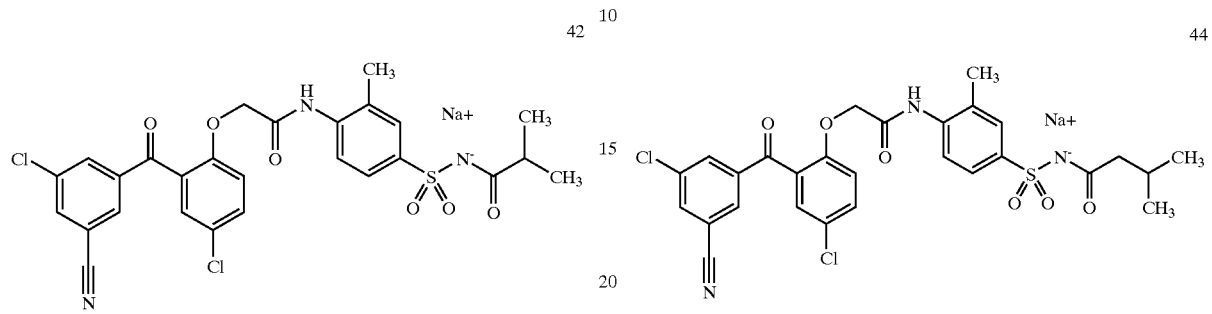

42

Step A:

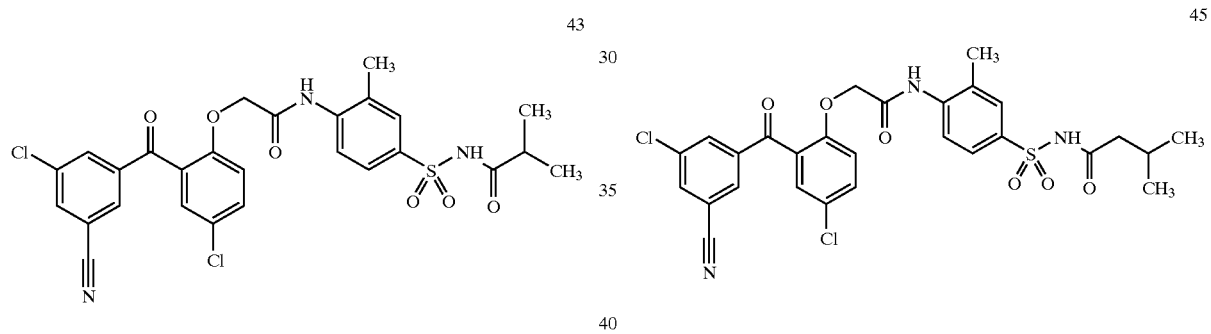

43

Isobutyric anhydride (Aldrich, 0.111 mL, 0.66 mmol) was added dropwise to a mixture of 40 (0.29 g, 0.6 mmol) and DMAP (0.073 g, 0.6 mmol) in 6 mL of $CH_2Cl_2$ and the resulting solution was brought to reflux. After 2 h, the reaction was then cooled to rt, washed with 1 N HCl and the organics were concentrated in vacuo. The solid was then washed with diethyl ether and purified by chromatography using 1:1 EtOAc: Hexanes as eluant to afford 43 as a white solid (0.11 g, 33%). $^1$H NMR (DMSO-$d_6$, 300 MHz) δ 11.94 (bs, 1H), 9.46 (s, 1H), 8.27 (m, 1H), 8.15 (m, 1H), 8.08 (m, 1H), 7.78 (d, 1H), 7.64–7.72 (m, 3H), 7.53 (d, 1H), 7.23 (d, 1H), 4.83 (s, 2H), 2.44 (m, 1H), 2.22 (s, 3H), 0.94 (s, 3H), 0.91 (s, 3H); LC-MS (ES$^+$) m/z 588 (M+H)$^+$, 610 (M+Na); (ES$^-$) m/z 586 (M–H)$^-$.

Step B:

Benzophenone 43 (0.11 g, 0.19 mmol) was combined with 1 N NaOH (0.26 mL, 0.26 mmol) then water was added until the solid dissolved. The resulting solution was lyophilized to afford 42 as an off-white solid (0.093 g, 81%). $^1$H NMR (DMSO-$d_6$, 300 MHz) δ 9.31 (s, 1H), 8.30 (s, 1H), 8.15 (s, 1H), 8.08 (s, 1H), 7.67 (dd, 1H), 7.52 (m, 2H), 7.46 (d, 1H), 7.37 (d, 1H), 7.22 (d, 1H), 4.78 (s, 2H), 2.04–2.13 (m, 4H), 0.88 (s, 3H), 0.86 (s, 3H); LC-MS (ES$^+$) m/z 610 (M+Na)$^+$.

EXAMPLE 12

2-[4-chloro-2-(3-chloro-5-cyanobenzoyl)phenoxy]-N-(2-methyl-4-{[(3-methylbutanoyl)amino]sulfonyl}phenyl)acetamide, Sodium Salt

44

Step A:

45

Isovaleric anhydride (TCI, 0.126 mL, 0.64 mmol) was added dropwise to a mixture of 40 (0.3 g, 0.58 mmol) and DMAP (0.071 g, 0.58 mmol) in 6 mL of $CH_2Cl_2$ and the resulting solution was brought to reflux. After 2.5 h, the reaction was then cooled to rt, washed with 1 N HCl and the organics were concentrated in vacuo. The product was then purified by chromatography using 1:1 EtOAc: Hexanes as eluant to afford 45 as an off-white solid (0.15 g, 43%). $^1$HNMR (DMSO-$d_6$, 300 MHz) δ 11.95 (bs, 1H), 9.45 (s, 1H), 8.28 (m, 1H), 8.15 (m, 1H), 8.08 (m, 1H), 7.63–7.74 (m, 4H), 7.53 (d, 1H), 7.23 (d, 1H), 4.83 (s, 2H), 2.20 (s, 3H), 2.01 (d, 2H), 1.87 (m, 1H), 0.77 (s, 3H), 0.75 (s, 3H); LC-MS (ES$^+$) m/z 602 (M+H)$^+$, 624 (M+Na); (ES$^-$) m/z 600 (M–H)$^-$.

Step B:

Benzophenone 45 (0.15 g, 0.25 mmol) was combined with 1 N NaOH (0.274 mL, 0.274 mmol) then water was added until the solid dissolved. The resulting solution was lyophilized to afford 44 as an off-white solid (0.137 g, 88%). $^1$H NMR (DMSO-$d_6$, 300 MHz) δ 9.32 (s, 1H), 8.30 (s, 1H), 8.15 (s, 1H), 8.08 (s, 1H), 7.67 (dd, 1H), 7.52 (m, 2H), 7.46 (d, 1H), 7.37 (d, 1H), 7.22 (d, 1H), 4.78 (s, 2H), 2.10 (s, 3H), 1.84 (m, 1H), 1.74 (d, 2H), 0.77 (s, 3H), 0.75 (s, 3H); LC-MS (AP$^+$) m/z 624 (M+Na)$^+$, (ES$^+$) m/z 624 (M+Na)$^+$.

EXAMPLE 13

2-[4-chloro-2-(3-chloro-5-cyanobenzoyl)phenoxy]-N-(2-methyl-4-{1(1-pyrrolidinylacetyl)amino]sulfonyl}phenyl)acetamide, Sodium Salt

46

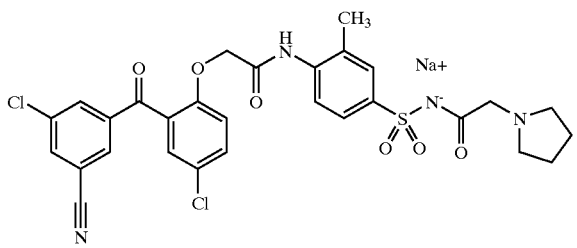

Step A:

47

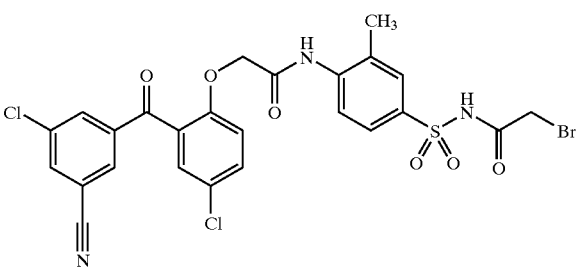

A mixture of 40 (0.32 g, 0.6 mmol) and DMAP (0.075 g, 0.6 mmol) in 6 mL of CH$_2$Cl$_2$ was cooled to 0° C. Bromoacetic acid anhydride (Lancaster, 0.272 mL of 65% w/v solution in acetonitrile, 0.68 mmol) was added dropwise. The reaction was then brought to reflux under nitrogen. After 2 d, the reaction was cooled to rt, and filtered. The filtered solid was washed with CH$_2$Cl$_2$. The filtrate was then washed with 1 N HCl then dried over Na$_2$SO$_4$, filtered, and concentrated in vacuo. The product was triturated with diethyl ether and air-dried to afford 47 as a white solid (0.074 g, 12%, crude). The crude intermediate was used immediately.

Step B:

48

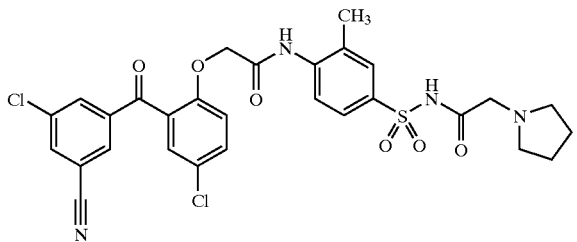

A mixture of 47 (0.074 g, 0.12 mmol), sodium iodide (0.01 g, 0.07 mmol), and pyrrolidine (Aldrich, 0.015 mL, 0.17 mmol) in 2 mL of CH$_2$Cl$_2$ was stirred at room temperature for 15 h. The suspension was then concentrated in vacuo and then purified by TLC prep plate eluted with 9:1 CH$_2$Cl$_2$:MeOH to afford 48 as an off-white solid (0.015 g, 20%). $^1$H NMR (DMSO-d$_6$, 300 MHz) δ 9.33 (s, 1H), 8.29 (m, 1H), 8.15 (m, 1H), 8.07 (m, 1H), 7.66 (dd, 1H), 7.42–7.55 (m, 3H), 7.22 (d, 1H), 4.78 (s, 2H), 4.01 (s, 2H), 3.58 (m, 2H), 2.12 (s, 3H), 1.91 (m, 2H).

Step C:

Benzophenone 48 (0.01 g, 0.016 mmol) was combined with 1 N NaOH (0.018 mL, 0.018 mmol) then water was added until the solid dissolved. The resulting solution was lyophilized to afford 46 as a tan solid (0.011 g, 69%). $^1$H NMR (DMSO-d$_6$, 300 MHz) δ 9.33 (s, 1H), 8.29 (m, 1H), 8.15 (m, 1H), 8.07 (m, 1H), 7.66 (dd, 1H), 7.42–7.55 (m, 3H), 7.22 (d, 1H), 4.78 (s, 2H), 4.01 (s, 2H), 3.55 (m, 2H), 2.12 (s, 3H), 1.91 (m, 2H), 1.22 (s, 2H).

EXAMPLE 14

N-{4-[(butyrylamino)sulfonyl]-2-methylphenyl}-2-[4-chloro-2-(3-chloro-5-cyanobenzoyl)phenoxy]acetamide, Sodium Salt

49

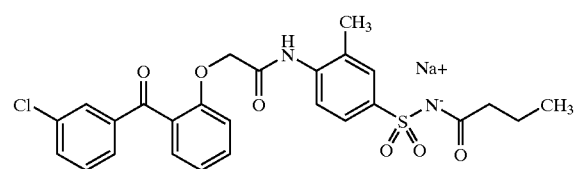

Step A:

50

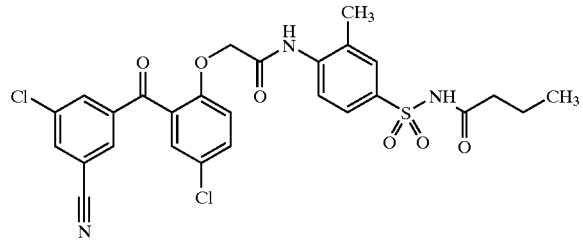

n-Butyric anhydride (Aldrich, 0.038 mL, 0.23 mmol) in 1 mL CH$_2$Cl$_2$ of was added dropwise to a mixture of 40 (0.1 g, 0.19 mmol) and DMAP (0.024 g, 0.19 mmol) in 6 mL of CH$_2$Cl$_2$ and the resulting solution was brought to reflux. After 2.5 h, the reaction was then cooled to rt and stirred for 5 d. The solution was washed twice with 1 N HCl. Hexanes (10 mL) was added to the organics and the resulting suspension was filtered and the solid was washed with diethyl ether, dissolved in acetone and dried in vacuo to afford 50 as a white solid (0.09 g, 80%). $^1$H NMR (DMSO-d$_6$, 300 MHz) δ 11.99 (s, 1H), 9.61 (s, 1H), 8.27 (m, 1H), 8.15 (m, 1H), 8.07 (m, 1H), 7.76 (d, 1H), 7.63–7.72 (m, 3H), 7.52 (d, 1H), 7.23 (d, 1H), 4.85 (s, 2H), 2.22 (s, 3H), 2.15 (t, 2H), 1.40 (q, 2H), 0.74 (t, 3H); LC-MS (ES$^+$) m/z 588 (M+H)$^+$, 610 (M+Na); (ES$^-$) m/z 586 (M−H)$^-$.

Step B:

Compound 50 (0.086 g, 0.15 mmol) was combined with 1 N NaOH (0.161 mL, 0.161 mmol) then water was added until the solid dissolved. The resulting solution was lyophilized to afford 49 as an off-white solid (0.084 g, 94%). $^1$H NMR (DMSO-d$_6$, 400 MHz) δ 9.40 (s, 1H), 8.30 (m, 1H), 8.15 (m, 1H), 8.07 (m, 1H), 7.67 (dd, 1H), 7.59 (s, 1H), 7.53 (m, 2H), 7.22 (d, 1H), 4.80 (s, 2H), 2.15 (t, 3H), 1.96 (t, 3H) 1.38 (q, 2H), 0.75 (t, 3H); LC-MS (AP$^+$) m/z 588 (M+H)$^+$, 610 (M+Na)$^+$, (AP$^-$) m/z 586 (M−H)$^-$

EXAMPLE 15

2-[4-chloro-2-(3-chloro-5-cyanobenzoyl)phenoxy]-N-{2-methyl-4-[(pentanoylamino)sulfonyl]phenyl}acetamide, Sodium Salt

51

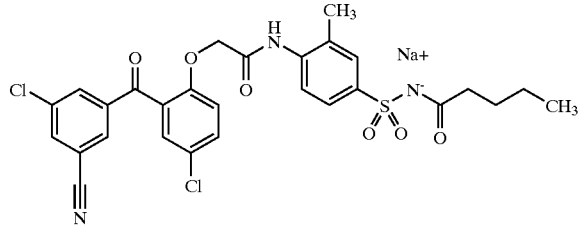

Step A:

52

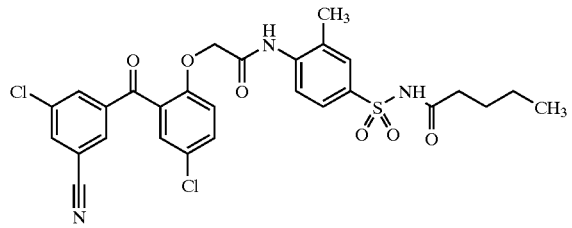

Valeric anhydride (Fluka, 0.045 mL, 0.23 mmol) was added dropwise to a mixture of 40 (0.1 g, 0.19 mmol) and DMAP (0.045 g, 0.19 mmol) in 6 mL of $CH_2Cl_2$ and the resulting solution was brought to reflux. After 2.5 h, the reaction was then cooled to rt and stirred for 5 d. The solution was washed twice with 1 N HCl. Diethyl ether (10 mL) was added to the organics and the resulting suspension was filtered and the solid was washed with diethyl ether and air-dried to afford 52 as a white solid (0.055 g, 47%). $^1$H NMR (DMSO-$d_6$, 300 MHz) δ 11.95 (s, 1H), 9.49 (s, 1H), 8.27 (m, 1H), 8.15 (m, 1H), 8.07 (m, 1H), 7.77 (d, 1H), 7.63–7.71 (m, 3H), 7.53 (d, 1H), 7.22 (d, 1H), 4.83 (s, 2H), 2.22 (s, 3H), 2.17 (t, 2H), 1.36 (q, 2H), 1.07 (t, 2H), 0.77 (t, 3H); LC-MS (ES$^+$) m/z 602 (M+H)$^+$, 624 (M+Na); (ES$^-$) m/z 600 (M−H)$^-$.

Step B:

Benzophenone 52 (0.055 g, 0.1 mmol) was combined with 1 N NaOH (0.106 mL, 0.106 mmol) then water was added until the solid dissolved. The resulting solution was lyophilized to afford 51 as an off-white solid (0.062 g, 99%). $^1$H NMR (DMSO-$d_6$, 400 MHz) δ 9.30 (s, 1H), 8.31 (m, 1H), 8.15 (m, 1H), 8.08 (m, 1H), 7.67 (dd, 1H), 7.52 (d, 1H), 7.51 (s, 1H), 7.45 (m, 1H), 7.36 (d, 1H), 7.22 (d, 1H), 4.78 (s, 2H), 2.10 (s, 3H), 1.85 (t, 2H), 1.33 (m, 2H), 1.16 (m, 2H), 0.80 (t, 3H); LC-MS (AP$^+$) m/z 624 (M+Na)$^+$, 602 (M+H)$^+$; (AP$^-$) m/z 600 (M−H)$^-$.

EXAMPLE 16 isobutyl {4-[({4-chloro-2-[3-cyano-5-(trifluoromethyl)benzoyl]phenoxy}acetyl)amino]-3-methylphenyl}sulfonylcarbamate, Sodium Salt

53

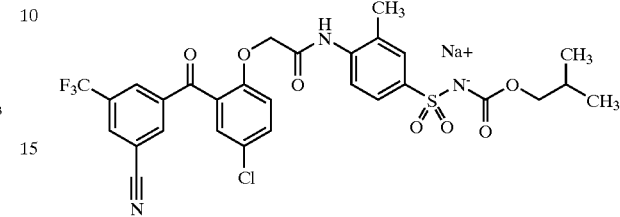

Step A:

54

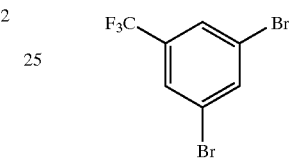

To a solution of copper (II) bromide (5.36 g, 24 mmol) in acetonitrile (100 ml) at 0° C. was added t-butyl nitrite (3.8 ml, 32 mmol) dropwise, and then 3-amino-5-bromobenzotrifluoride (5 g, 21 mmol) dropwise. The mixture was stirred at 0° C. for 1.5 h, then at room temperature for 16 h. The mixture was then concentrated to half of its original volume in vacuo, and then poured into 1N HCl (120 ml). This mixture was extracted with ether (100 mL). The organic layer was washed with 1N HCl, dried ($Na_2SO_4$), filtered, concentrated in vacuo (Note: product is fairly volatile, and should not be exposed to high vacuum for extended periods of time) to give 54 as a brown oil (5.12 g), which was used as is without further purification. $^1$H NMR (CDCl$_3$, 400 MHz) δ 7.82 (s, 1H), 7.67 (s, 2H).

Step B:

55

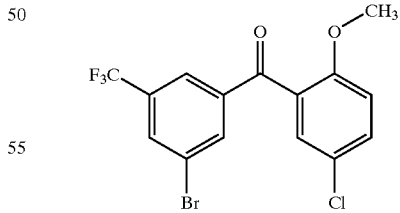

54 (5.12 g), N-methyl-N-methoxy-2-methoxy-5-chlorobenzamide (3.6 g, 16.8 mmol), and n-butyllithium (8.76 ml of 2.7M solution in heptane) were treated according to the procedure outlined in Part A of Example 2 to give 55 (3.36 g), which was used as is without further purification. $^1$H NMR (CDCl$_3$, 400 MHz) δ 8.02 (s, 1H), 7.89 (d, 2H), 7.46 (dd, 1H), 7.38 (d, 1H), 6.92 (d, 1H), 3.66 (s, 3H).

Step C:

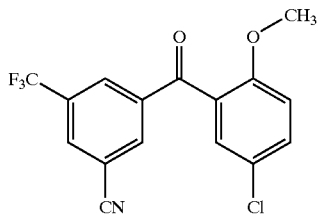
56

55 (3.36 g, 8.55 mmol), sodium cyanide (838 mg, 17 mmol), copper (I) iodide (325 mg, 1.7 mmol), and tetrakis(triphenylphospine)palladium (0) (987 mg, 0.86 mmol) were used according to general procedure XV to give 56 (1.35 g) after silica gel purification (10% ethyl acetate/hexanes). $^1$H NMR (CDCl$_3$, 400 MHz) δ 8.19 (s, 1H), 8.13 (s, 1H), 8.04 (s, 1H), 7.50 (dd, 1H), 7.43 (d, 1H), 6.94 (1H), 3.65 (s, 3H).

Step D:

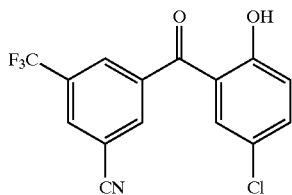
57

56 (1.35 g, 3.98 mmol) was treated according to the procedure for the synthesis of compound 8 to give 57 (1.29 g, >99%) as a yellow oil, which was used without further purification. $^1$H NMR (CDCl$_3$, 300 MHz) δ 11.49 (s, 1H), 8.20–8.16 (m, 3H), 7.59 (dd, 1H), 7.38 (d, 1H), 7.15 (d, 1H).

Step E:

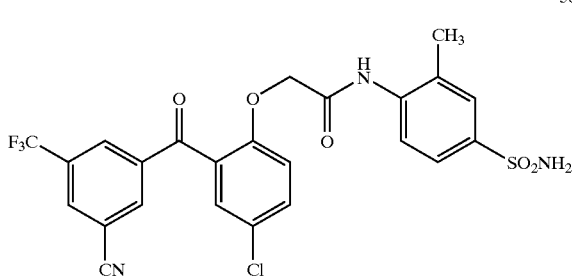
58

57 (487 mg, 1.5 mmol) and 39 were treated according to step E in example 10 to give a crude product which was purified by silica gel chromatography (8:1:1 CH$_2$Cl$_2$/ethyl acetate/methanol) and triturated with ether to give 58 (315 mg) as an off-white solid. $^1$H NMR (DMSO-d$_6$, 400 MHz) δ 9.41 (s, 1H), 8.56 (s, 1H), 8.45 (s, 1H), 8.27 (s, 1H), 7.66–7.52 (m, 5H), 7.19 (m, 3H), 4.76 (s, 2H), 2.12 (s, 3H); MS(ES$^-$): m/z 550 (M–H)$^-$.

Step F:

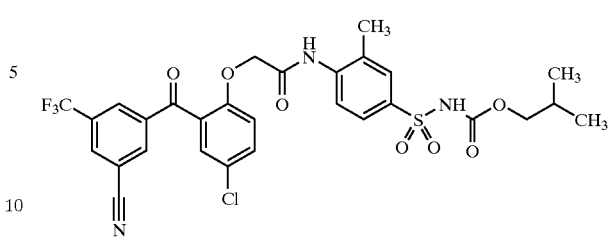
59

Isobutyl chloroformate (Aldrich, 0.014 mL, 0.11 mmol) was added dropwise to a mixture of 58 (0.05 g, 0.09 mmol) and DMAP (0.011 g, 0.09 mmol) in 3.5 mL of CH$_2$Cl$_2$ and the resulting solution was stirred at rt. After ½ h, the reaction was washed twice with 1 N HCl and the organics were concentrated in vacuo to afford 59 as a clear glass (0.06 g, 99%). $^1$H NMR (CDCl$_3$, 400 MHz) δ 8.7 (s, 1H), 8.32 (s, 1H), 8.23 (d, 2H), 8.19 (d, 1H), 7.88–7.91 (m, 2H), 7.64 (dd, 1H), 7.36 (d, 1H), 7.11 (d, 1H), 4.76 (s, 2H), 3.87 (d, 2H), 2.39 (s, 3H), 1.89 (m, 1H), 0.89 (s, 3H), 0.88 (s, 3H); LC-MS (ES$^+$) m/z 652 (M+H)$^+$, 674 (M+Na); (ES$^-$) m/z 650 (M–H)$^-$.

Step G:

Benzophenone 59 (0.04 g, 0.06 mmol) was combined with 1 N NaOH (0.073 mL, 0.073 mmol) then water was added until the solid dissolved. The resulting solution was lyophilized to afford 53 as an off-white solid (0.04 g, 98%). $^1$H NMR (DMSO-d$_6$, 300 MHz) δ 9.33 (s, 1H), 8.63 (s, 1H), 8.50 (s, 1H), 8.32 (s, 1H), 7.69 (dd, 1H), 7.56 (m, 1H), 7.43–7.5 (m, 2H), 7.36 (d, 1H), 7.23 (d, 1H), 4.77 (s, 2H), 3.41 (d, 2H), 2.09 (s, 3H), 1.66 (m, 1H), 0.79 (s, 3H), 0.77 (s, 3H); LC-MS (ES$^+$) m/z 652 (M+H)$^+$, 674 (M+Na); (ES$^-$) m/z 650 (M–H)$^-$.

EXAMPLE 17 isobutyl [4-({[4-chloro-2-(3-chloro-5-cyanobenzoyl)phenoxy]acetyl}amino)-3-methylphenyl]sulfonylcarbamate, Sodium Salt

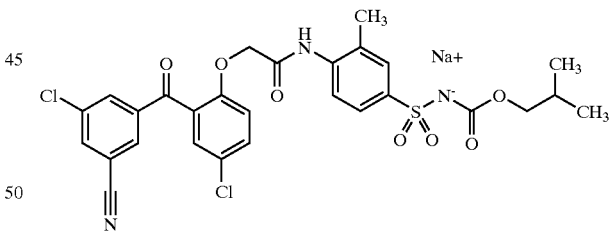
60

Step A:

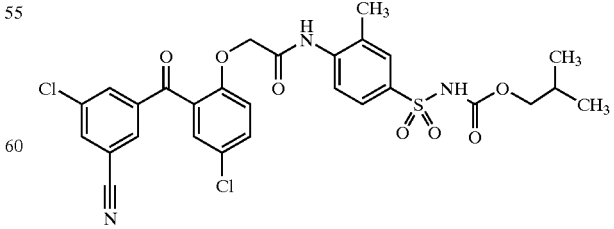
61

Isobutylchloroformate (Aldrich, 0.016 mL, 0.12 mmol) was added dropwise to a mixture of 40 (0.05 g, 0.1 mmol)

and DMAP (0.012 g, 0.1 mmol) in 3.5 mL of CH$_2$Cl$_2$ and the resulting solution was stirred at rt overnight. The reaction was washed twice with 1 N HCl and the organics were dried over MgSO$_4$, filtered, and concentrated in vacuo. The resulting clear glass was re-dissolved in CH$_2$Cl$_2$, washed with a 5% aqueous NaHCO$_3$ solution, and the organics were concentrated in vacuo to afford 61 as a white solid (0.033 g, 52%). $^1$H NMR (DMSO-d$_6$, 300 MHz) δ 11.9 (bs, 1H), 9.48 (s, 1H), 8.29 (t, 1H), 8.15 (t, 1H), 8.07 (t, 1H), 7.78 (d, 1H), 7.65–7.71 (m, 3H), 7.54 (d, 1H), 7.23 (d, 1H), 4.84 (s, 2H), 3.74 (d, 2H), 2.22 (s, 3H), 1.76 (m, 1H), 0.8 (s, 3H), 0.77 (s, 3H); LC-MS (ES$^+$) m/z 617 (M+)$^+$, 640 (M+Na); (ES$^-$) m/z 616 (M–H)$^-$.

Step B:

Benzophenone 61 (0.033 g, 0.05 mmol) was combined with 1 N NaOH (0.059 mL, 0.59 mmol) then water was added until the solid dissolved. The resulting solution was lyophilized to afford 60 as an off-white solid (0.034 g, 99%). $^1$H NMR (DMSO-d$_6$, 300 MHz) δ 9.32 (s, 1H), 8.31 (m, 1H), 8.15 (s, 1H), 8.08 (m, 1H), 7.67 (dd, 1H), 7.37–7.53 (m, 4H), 7.22 (d, 1H), 4.78 (s, 2H), 3.41 (d, 2H), 2.11 (s, 3H), 1.67 (m, 1H), 0.79 (s, 3H), 0.77 (s, 3H); LC-MS (ES$^+$) m/z 618 (M+H)$^+$, 640 (M+Na); (ES$^-$) m/z 616 (M–H)$^-$.

EXAMPLE 18

2-methoxyethyl [4-({[4-chloro-2-(3-chloro-5-cyanobenzoyl)phenoxy]acetyl}amino)-3-methylphenyl]sulfonylcarbamate, Sodium Salt

62

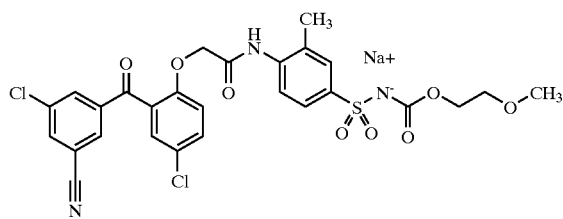

Step A:

63

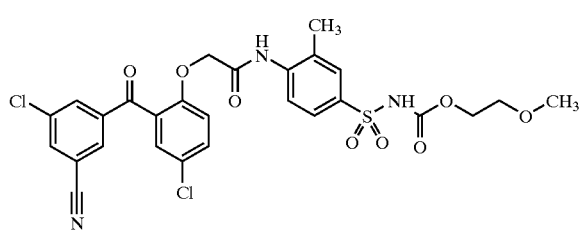

Chloroformic acid 2-methoxyethyl ester (Takeda Chemical Industries, LTD., 0.014 mL, 0.12 mmol) was added dropwise to a mixture of 40 (0.05 g, 0.1 mmol) and DMAP (0.012 g, 0.1 mmol) in 3.5 mL of CH$_2$Cl$_2$ and the resulting solution was stirred at rt. After 2 h, the reaction was washed twice with 1 N HCl and the organics were dried over MgSO$_4$, filtered, and concentrated in vacuo to afford 63 as a white solid (0.043 g, 72%). $^1$H NMR (DMSO-d$_6$, 300 MHz) δ 12.01 (bs, 1H), 9.48 (s, 1H), 8.29 (t, 1H), 8.16 (t, 1H), 8.08 (t, 1H), 7.79 (d, 1H), 7.65–7.71 (m, 3H), 7.54 (d, 1H), 7.22 (d, 1H), 4.84 (s, 2H), 4.07–4.1 (m, 3.41–3.45 (m, 2H), 3.19 (s, 3H), 2.22 (s, 3H); LC-MS (ES$^+$) m/z 620 (M+H)$^+$, 642 (M+Na); (ES$^-$) m/z 619 (M–)$^-$.

Step B:

Benzophenone 63 (0.043 g, 0.069 mmol) was combined with 1 N NaOH (0.076 mL, 0.076 mmol) then water was added until the solid dissolved. The resulting solution was lyophilized to afford 62 as an off-white solid (0.04 g, 91%). $^1$H NMR (DMSO-d$_6$, 300 MHz) δ 9.32 (s, 1H), 8.31 (m, 1H), 8.15 (m, 1H), 8.08 (m, 1H), 7.67 (dd, 1H), 7.37–7.53 (m, 3H), 7.22 (d, 1H), 4.78 (s, 2H), 3.74 (t, 2H), 3.32 (m, 2H), 3.19 (s, 3H), 2.11 (s, 3H); LC-MS (ES$^+$) m/z 620 (M+H)$^+$, 642 (M+Na); (ES$^-$) m/z 619 (M–)$^-$.

EXAMPLE 19

2-[4-chloro-2-(3-chloro-5-cyanobenzoyl)phenoxy]-N-(4-{[(methoxyacetyl)amino]sulfonyl}-2-methylphenyl)acetamide, Sodium Salt

64

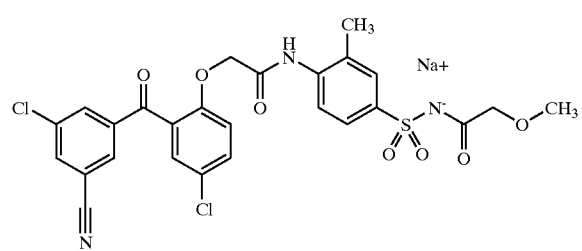

Step A:

65

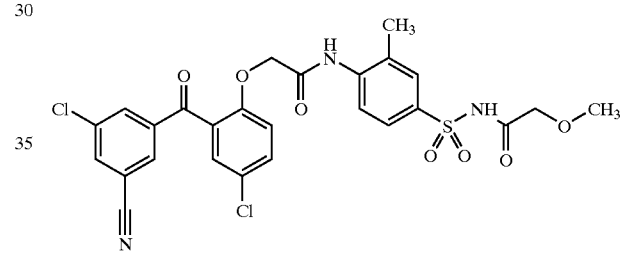

Methoxyacetyl chloride (Aldrich, 0.011 mL, 0.12 mmol) was added dropwise to a mixture of 40 (0.05 g, 0.097 mmol) and DMAP (0.012 g, 0.097 mmol) in 3.5 mL of CH$_2$Cl$_2$ and the resulting solution was stirred at rt. After 20 h, the reaction was then washed twice with 1 N HCl and the organics were dried over MgSO$_4$, filtered, and concentrated in vacuo. The solid was then triturated with diethyl ether, filtered, and air dried to afford 65 as a white solid (0.041 g, 72%). $^1$H NMR (DMSO-d$_6$, 300 MHz) δ 12.04 (bs, 1H), 9.48 (s, 1H), 8.28 (t, 1H), 8.16 (m, 1H), 8.08 (m, 1H), 7.64–7.81 (m, 4H), 7.53 (m, 1H), 7.22 (m, 1H), 4.84 (s, 2H), 3.89 (s, 2H), 3.21 (s, 3H), 2.23 (s, 3H); LC-MS (AP$^+$) m/z 590 (M+H)$^+$, 612 (M+Na); LC-MS (ES$^+$) m/z 590 (M+H)$^+$, 612 (M+Na); (ES)$^-$ m/z 588 (M–H)$^-$.

Step B:

Benzophenone 65 (0.11 g, 0.19 mmol) was combined with 1 N NaOH (0.26 mL, 0.26 mmol) then water was added until the solid dissolved. The resulting solution was lyophilized to afford 64 as an off-white solid (0.093 g, 81%). $^1$H NMR (DMSO-d$_6$, 300 MHz) δ 9.31 (s, 1H), 8.30 (s, 1H), 8.15 (s, 1H), 8.08 (s, 1H), 7.67 (dd, 1H), 7.52 (m, 2H), 7.46 (d, 1H), 7.37 (d, 1H), 7.22 (d, 1H), 4.78 (s, 2H), 2.04–2.13 (m, 4H), 0.88 (s, 3H), 0.86 (s 3H); LC-MS (ES$^+$) m/z 610 (M+Na)$^+$.

EXAMPLE 20

2-{4-chloro-2-[3-fluoro-5-(trifluoromethyl)benzoyl]phenoxy}-N-(4-{[(ethoxymethyl)amino]sulfonyl}-2-methylphenyl)acetamide

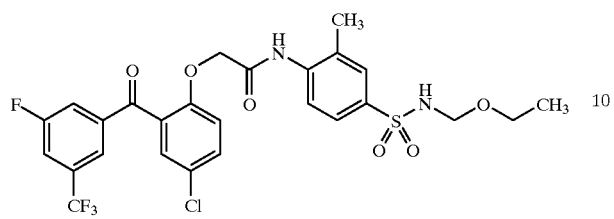

66

Step A:

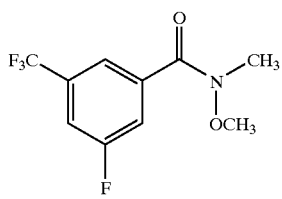

67

Into a round-bottom flask equipped with a stir bar and nitrogen on demand were placed N,O-dimethylhydroxylamine hydrochloride (2.80 g, 28.7 mmol), Et₃N (9.0 mL, 64.57 mmol) and CHCl₃ (50 mL). The solution was cooled to 0° C. and 3-trifluoromethyl-5-fluorobenzoyl chloride (5.0 g, 22.07 mmol) was added dropwise over several minutes. The resulting solution was allowed to stir at 0° C. for 30 min, after which time it was allowed to warm to rt and stir for an additional 30 min. The mixture was then poured into a separatory funnel containing ethyl acetate and water. The organic layer was collected and was washed with water, brine, dried over MgSO₄, filtered and the solvents were removed under reduced pressure to provide 67 as a clear oil which was used without any further purification. ¹H NMR (CDCl₃, 300 MHz) δ 7.83 (s, 1H), 7.65 (d, J=9 Hz, 1H), 7.46 (d, J=9 Hz, 1H), 3.59 (s, 3H), 3.42 (s, 3H).

Step B:

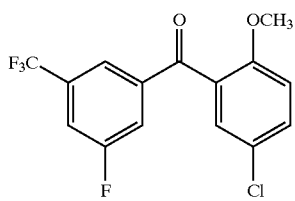

68

Into a round-bottom flask equipped with a stir bar and nitrogen on demand were placed 2-bromo-4-chloroanisole (4.05 g, 18.29 mmol) and Et₂O (75 mL). The solution was cooled to -78° C. and n-butyl lithium (13 mL of a 1.6 M solution in hexane, 20.8 mmol) was added dropwise. The resulting mixture was allowed to stir at -78° C. for 15 min, after which time amide 67 (5.04 g, 20.07 mmol) was added dropwise. The mixture was allowed to stir at -78° C. for 30 min, after which time it was allowed to warm to rt and stir for an additional 2 h. The mixture was then poured into a separatory funnel containing ethyl acetate and water. The organic layer was collected and was washed with water, brine, dried over MgSO₄, filtered and the solvents were removed under reduced pressure afford 69 as a yellow solid (6.14 g, 92%), which was used in subsequent reactions without any further purification. ¹H NMR (CDCl₃, 300 MHz) δ 7.84 (s, 1H), 7.68 (d, J=9 Hz, 1H), 7.58–7.51 (m, 2H), 7.44 (d, J=3 Hz, 1H), 7.00 (d, J=9 Hz, 1H), 3.74 (s, 3H).

Step C:

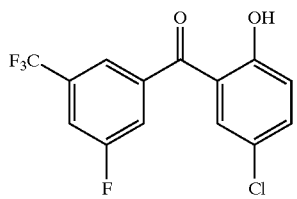

69

Into a round-bottom flask equipped with a stir bar and nitrogen on demand were placed 68 (6.14 g, 18.46 mmol) and CH₂Cl₂ (100 mL). The solution was cooled to -78° C. and boron tribromide (50 mL of a 1.0 M solution in CH₂Cl₂, 50 mmol) was added dropwise over several minutes. The resulting dark mixture was allowed to stir at -78° C. for 30 min, after which time it was allowed to warm to rt and stir for an additional 1 h. The mixture was carefully poured over ice and the two-phase mixture was stirred for 30 min. It was then poured into a separatory funnel containing CH₂Cl₂ and water. The organic layer was collected, washed with water, brine, dried over MgSO₄, filtered and the solvents were removed under reduced pressure to afford 69 as a yellow solid (5.68 g, 96%), which was used without any further purification. ¹H NMR (CDCl₃, 300 MHz) δ 11.61 (s, 1H), 7.77 (s, 1H), 7.65–7.54 (m, 3H), 7.47 (d, J=3 Hz, 1H), 7.12 (d, J=9 Hz, 1H).

Step D:

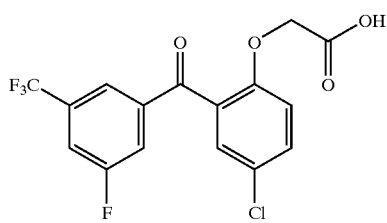

70

Phenol 69 (5.68 g, 17.83 mmol), ethyl bromoacetate (2 mL, 18.03 mmol), K₂CO₃ (9.61 g, 69.53 mmol) and acetone (35 mL) were used according to general procedure II to provide the ester as a yellow, viscous oil which was used without any further purification. The ester (6.83 g, 16.88 mmol), lithium hydroxide (1.42 g, 33.84 mmol), water (20 mL), THF (50 mL) and EtOH (20 mL) were used according to general procedure III. The product was washed with several portions of ether to provide 70 as a white solid that was used without any further purification.

Step E:

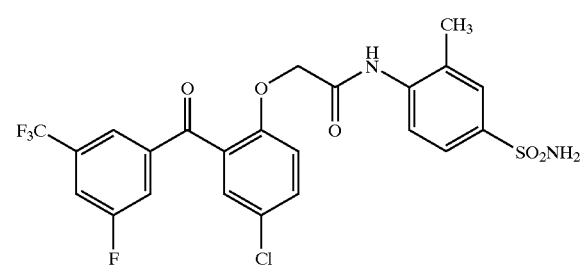

71

Carboxylic acid 70 (11.24 g, 29.84 mmol), oxalyl chloride (3.9 mL, 44.71 mmol), DMF (5 mL) and chloroform (250 mL) were used according to general procedure V to prepare the acid chloride, which was used without further purification. The acid chloride, sulfonamide (5.12 g, 27.49 mmol), NaHCO$_3$ (11.12 g, 132 mmol), acetone (300 mL) and water (10 mL) were used according to general procedure VI. The product was purified by crystallization from a mixture of acetonitrile/water to provide 71 as a white solid (9.01 g, 60%). $^1$H NMR (DMSO-d$_6$, 300 MHz) δ 9.47 (s, 1H), 8.05 (d, J=9 Hz, 1H), 7.93–7.90 (m, 2H), 7.73–7.50 (m, 5H), 7.30–7.26 (m, 3H), 4.84 (s, 2H), 2.19 (s, 3H). Anal Calcd. for C$_{23}$H$_{17}$ClF$_4$N$_2$O$_5$S: C, 50.70; H, 3.14; N, 5.14. Found: C, 50.75; H, 3.10; N, 5.21.

Step F:

Compound 71 (0.1 g, 0.18 mmol), formaldehyde (0.015 mL of a 37% soln. in H$_2$O, 0.20 mmol), and absolute ethanol (8 mL) were added to a round bottom flask and heated to reflux for 16 h. After which time, the reaction was allowed to cool to RT and the solid which precipitated was collected, washed with Et$_2$O and filtered to provide 66 (0.045 g, 41%) as a white solid: MS (ES–) m/z 601 (M–H)$^-$; $^1$H NMR (400 MHz, DMSO-d$_6$) δ 9.38 (s, 1H), 8.65 (t, 1H), 7.96 (d, 1H), 7.83 (m, 2H), 7.55 (m, 5H), 7.19 (d, 1H), 4.78 (s, 2H), 4.38 (d, 2H), 3.14 (m, 2H), 2.12 (s, 3H), 0.77 (t, 3H) ppm.

EXAMPLE 21

2-{4-chloro-2-[3-fluoro-5-(trifluoromethyl)benzoyl]phenoxy}-N-{4-[({[2-(2-methoxyethoxy)ethoxy]methyl}amino)sulfonyl]-2-methylphenyl}acetamide

72

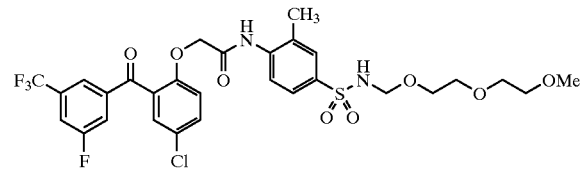

Compound 71 (0.15 g, 0.28 mmol), formaldehyde (0.030 mL of a 37% soln. in H$_2$O, 0.36 mmol), and di(ethyleneglycol)methyl ether (8 mL) were added to a round bottom flask and heated to 80–100° C. for 40 h. When judged to be complete, the reaction was allowed to cool to RT and was poured into EtOAc and H$_2$O. The organics were collected, washed with brine, dried over MgSO$_4$, and filtered. The aqueous layer was collected and allowed to stand at RT for 7 days, after which time a solid precipitated, was collected and recrystallized from absolute ethanol to provide 72 (0.05 g, 26%) as a white solid: MS (ES+) m/z 572 (M$^+$); $^1$H NMR (400 MHz, DMSO-d$_6$) δ 9.37 (s, 1H), 7.96 (d, 1H), 7.83 (m, 2H), 7.73 (d, 1H), 7.62 (dd, 1H), 7.50 (m, 3H), 7.19 (d, 1H), 4.78 (s, 2H), 2.53 (s, 6H), 2.17 (s, 3H) ppm.

EXAMPLE 22

2-{4-chloro-2-[3-fluoro-5-(trifluoromethyl)benzoyl]phenoxy}-N-(2-methyl-4-{[methyl(4-morpholinylacetyl)amino]sulfonyl}phenyl)acetamide

73

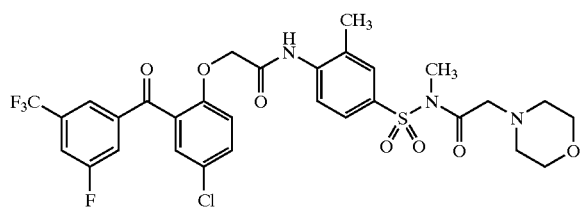

Step A:

74A

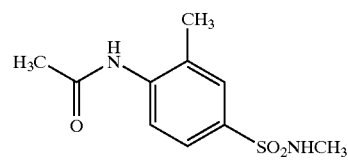

Into a round bottom flask equipped with a stir bar and gas dispersion tube was added the sulfonyl chloride 3 (11.5 g, 0.046 mol) and THF (250 mL) and the mixture was cooled to 0° C. Methylamine gas was bubbled through the reaction mixture for 0.5 h, after which time, the mixture was poured into EtOAc and water. The pH of the aqueous layer was adjusted to 7 using conc. HCl. The organics were collected, dried over MgSO$_4$, filtered and the solvents were removed under reduced pressure. The resulting orange residue was treated with Et$_2$O, filtered and dried to provide 74A (5.32 g, 48%): $^1$H NMR (300 MHz, DMSO-d$_6$) δ 9.46 (s, 1H), 7.80 (d, 1H), 7.58 (m, 2H), 7.34 (m, 1H), 2.41 (d, 3H), 2.32 (s, 3H), 2.13 (s, 3H) ppm.

Step B:

74B

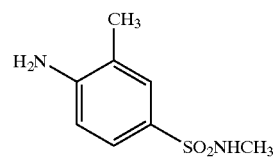

Into a round bottom flask equipped with a stir bar, reflux condensor, and nitrogen on demand was placed 74A (6.2 g, 0.026 mol), absolute EtOH (250 mL), and 1.5 N HCl aqueous soln. (75 mL). The mixture was warmed to reflux and allowed to stir for 6 h. When judged to be complete, the reaction was allowed to cool to RT and was then poured into a cold solution of saturated NaHCO$_3$. The mixture was extracted with several portions of EtOAc and the organics were dried over MgSO$_4$, filtered and concentrated under reduced pressure to provide 74B (3.6 g, 69%) as a yellow solid: $^1$H NMR (400 MHz, DMSO-d$_6$) δ 7.23 (m, 2H), 6.82 (m, 1H), 6.59 (d, 1H), 5.62 (bs, 2H), 2.26 (d, 3H), 2.03 (s, 3H) ppm.

Step C:

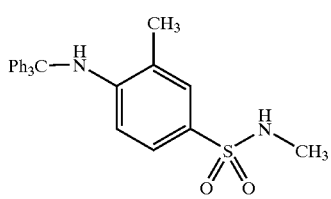

4-amino-N,3-dimethylbenzenesulfonamide (74B) (7.4 g, 0.037 mol), CH$_2$Cl$_2$ (150 mL), Et$_3$N (10.3 mL, 7.5 g, 0.074 mol), and triphenylmethyl chloride (10.9 g, 0.039 mol) were placed in a round bottom flask and were allowed to stir at RT for 30 min. After which time, a white precipitate formed which was collected and washed with CH$_2$Cl$_2$. The solid was dissolved in EtOAc, washed with water, dried over MgSO$_4$, filtered and concentrated to provide 74 (16.7 g, >99%) as a white solid: $^1$H NMR (400 MHz, DMSO-d$_6$) δ 7.27 (m, 15H), 6.90 (m, 2H), 5.96 (d, 1H), 5.77 (s, 1H), 2.44 (s, 3H), 2.22 (d, 3H) ppm.

Step D:

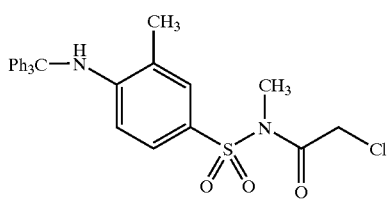

To a round bottom flask equipped with a stir bar, addition funnel and nitrogen on demand was added 74 (8.0 g, 0.018 mol) and anhydrous THF (300 mL). The reaction mixture was cooled to 40° C. by means of a CH$_3$CN/dry ice bath and potassium t-butoxide (27 mL of a 1M soln. in THF, 0.027 mol) was added dropwise via addition funnel over 15 min. The reaction mixture stirred for an additional 30 min. at 40° C. following the addition, after which time chloroacetyl chloride (1.6 mL, 2.3 g, 0.020 mol) was added via syringe and the mixture was allowed to warm to RT. When judged to be complete, the mixture was poured into EtOAc and H$_2$O. The organics were collected, washed with H$_2$O, dried over MgSO$_4$, filtered and concentrated. The residue was purified by flash chromatography using 4:1 hexanes:ethyl acetate as eluant to provide 75 (2.1 g, 23%) as a pale yellow solid: $^1$H NMR (400 MHz, DMSO-d$_6$) δ 7.54 (d, 1H), 7.21 (m, 15H), 6.00 (m, 2H), 4.65 (s, 2H), 3.09 (s, 3H), 2.35 (s, 3H) ppm.

Step E:

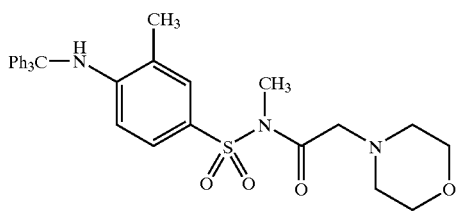

Into a test tube equipped with a stir bar was added 75 (0.5 g, 0.96 mmol), NaI (0.036 g, 0.24 mmol), morpholine (0.084 mL, 0.084 g, 0.96 mmol), and anhydrous THF (8 mL). The reaction was stirred for 16 h at RT, after which time, the mixture was partitioned between EtOAc and H$_2$O. The organics were collected, dried over MgSO$_4$, filtered and the solvents were removed under reduced pressure. The resulting residue was purified by flash chromatography using 7:3 hexanes:ethyl acetate as eluant to provide 76 (0.13 g, 26%). The resulting residue was used in the subsequent step without further characterization.

Step F:

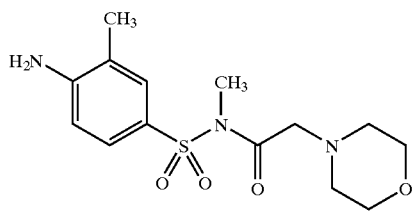

Into a round bottom flask equipped with a stir bar and nitrogen on demand was added 76 (0.14 g, 0.25 mmol) and a solution of CH$_2$Cl$_2$ and trifluoroacetic acid (2 mL of a 1:1 mixture) The reaction was stirred for 2 h at RT, after which time, the mixture was diluted with water and the pH of the aqueous layer was adjusted to 7 using solid NaHCO$_3$. The organics were collected, dried over MgSO$_4$, filtered and the solvents were removed under reduced pressure to provide 77 (0.13 g, >100%). The resulting residue was used in the subsequent step without further purification or characterization.

Step G:

Compound 70 (0.1 g, 0.26 mmol), oxalyl chloride (0.15 mL of a 2M soln. in CH$_2$Cl$_2$, 0.29 mmol), N,N-dimethylformamide (1 drop), and CH$_2$Cl$_2$ (5 mL) were used according to general procedure V to afford the acid chloride. The acid chloride, aniline 77 (0.12 g, 0.39 mmol), NaHCO$_3$ (0.034 g, 0.40 mmol), acetone (5 mL), and water (1 drop) were used according to general procedure VI. The resulting residue was treated with Et$_2$O and filtered to afford 73 (0.053 g, 30%) as a white solid: $^1$H NMR (400 MHz, DMSO-d$_6$) δ 9.42 (s, 1H), 7.96 (d, 1H), 7.83 (m, 2H), 7.71 (m, 3H), 7.60 (dd, 1H), 7.50 (d, 1H), 7.18 (d, 1H), 4.78 (s, 2H), 3.45 (bs, 4H), 3.35 (s, 2H), 2.30 (bs, 4H), 2.16 (s, 3H) ppm.

EXAMPLE 23

N$^1$-{[4-({[4-chloro-2-(3-chloro-5-cyanobenzoyl)phenoxy]acetyl}amino)-3-methylphenyl]sulfonyl}-L-isoleucinamide

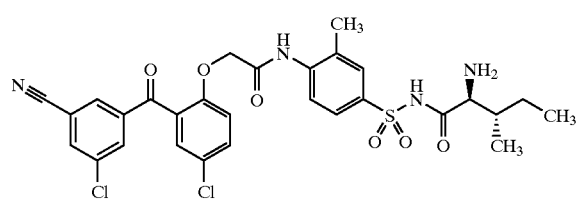

Step A:

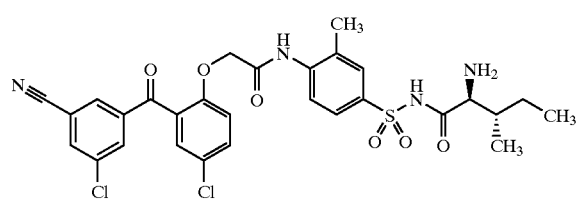

A mixture of 40 (0.2 g, 0.39 mmol), DMAP (Aldrich, 0.1 g, 0.82 mmol), and N-Boc-L-isoleucine (Sigma, 0.088 g, 0.38 mmol) in CH₂Cl₂ (30 mL) was cooled to 0° C. in an ice/water bath. EDAC (Sigma, 0.08 g, 0.38 mmol) was added to the cooled solution and the reaction mixture was allowed to warm to rt over 1 h. After 18 h, the reaction was cooled to 0° C. in an ice/water bath, washed with 1 N HCl, the organic layer was separated and concentrated in vacuo. The concentrate was dissolved in CH₂Cl₂ and purified by flash chromatography using 5% MeOH/CH₂Cl₂ to afford 79. The product was used in subsequent steps with no further purification.

Step B:

A mixture of 79 and TFA (2 mL) in CH₂Cl₂ (5 mL) was stirred at rt for 2 h then concentrated in vacuo. Purification by flash chromatography using 5–10% MeOH/CH₂Cl₂ gave 78 (0.172 g, 72% over 2 steps) as a white solid: ¹H NMR (CDCl₃, 300 MHz) δ 8.71 (s, 1H), 7.76 (d, 2H), 7.49–7.63 (m, 4H), 7.31 (m, 1H), 7.14 (m, 1H), 6.85 (d, 1H), 4.47 (s, 2 H), 2.32 (s, 3H), 1.99 (s, 3H), 1.71 (m, 1H), 1.14 (m, 1H), 0.80–0.93 (m, 1H), 0.57–0.67 (m, 6H); LC-MS (ES⁺) m/z 631 (M+H)⁺, (ES⁻) m/z 629 (M−H)⁻.

EXAMPLE 24

N¹-{[4-({[4-chloro-2-(3-chloro-5-cyanobenzoyl)phenoxy]acetyl}amino)-3-methylphenyl]sulfonyl}valinamide

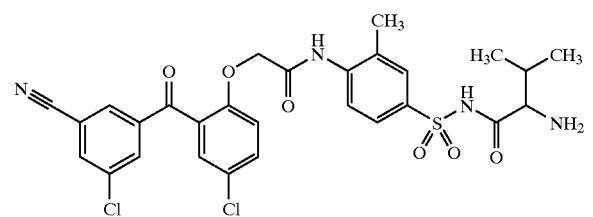

80

Step A:

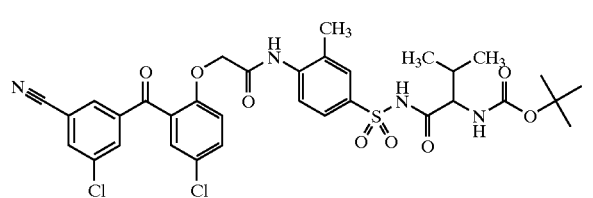

81

A mixture of 40 (0.2 g, 0.39 mmol), DMAP (Aldrich, 0.1 g, 0.82 mmol), and N-Boc-DL-valine (Sigma, 0.083 g, 0.38 mmol) in CH₂Cl₂ (30 mL) was cooled to 0° C. in an ice/water bath. EDAC (Sigma, 0.08 g, 0.38 mmol) was added to the cooled solution and it was allowed to warm rt over 1 h. After 18 h, the reaction was cooled to 0° C. in an ice/water bath, washed with 1 N HCl, the organic layer was separated and was concentrated in vacuo. The concentrate was dissolved in CH₂Cl₂ and purified by flash chromatography using 5% MeOH/CH₂Cl₂ to afford 81. The product was carried used with no further purification.

Step B:

A mixture of 81 and TFA (2 mL) in CH₂Cl₂ (5 mL) was stirred at rt for 2 h then concentrated in vacuo. Purification by flash chromatography using 5–10% MeOH/CH₂Cl₂ gave 80 (0.206 g, 88% over 2 steps) as a white solid: ¹H NMR (CDCl₃, 300 MHz) δ 8.67 (s, 1H), 7.63 (d, 2H), 7.36–7.49 (m, 4H), 7.15 (m, 1H), 7.00 (m, 1H), 6.71 (d, 1H), 4.33 (s, 2 H), 2.99 (m, 1H), 2.92 (m, 1H), 1.84 (s, 3H), 0.50 (m, 6H); LC-MS (ES⁺) m/z 617 (M+H)⁺, (ES⁻) m/z 615 (M−H)⁻.

EXAMPLE 25

N'-{[4-({[4-chloro-2-(3-chloro-5-cyanobenzoyl)phenoxy]acetyl}amino)-3-methylphenyl]sulfonyl}-L-leucinamide

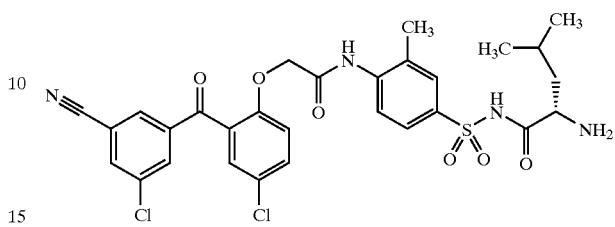

82

Step A:

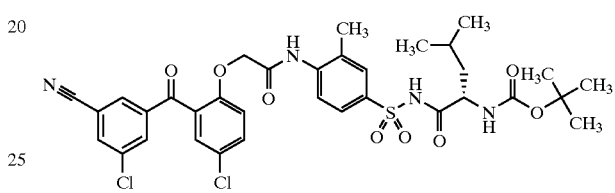

83

A mixture of 40 (0.2 g, 0.39 mmol), DMAP (Aldrich, 0.1 g, 0.82 mmol), and N-Boc-L-leucine (Sigma, 0.088 g, 0.38 mmol) in CH₂Cl₂ (30 mL) was cooled to 0° C. in an ice/water bath. EDAC (Sigma, 0.08 g, 0.38 mmol) was added and the reaction mixture was allowed to warm to rt over 1 h. After 18 h, the reaction was cooled to 0° C. in an ice/water bath, washed with 1 N HCl, the organic layer was separated and was concentrated in vacuo. The concentrate was dissolved in CH₂Cl₂ and purified by flash chromatography using 5% MeOH/CH₂Cl₂ to afford 83. The product was used with no further purification.

Step B:

A mixture of 83 and TFA (2 ml) in CH₂Cl₂ (5 mL) was stirred at rt for 2 h then concentrated in vacuo. Purification by flash chromatography using 5–10% MeOH/CH₂Cl₂ gave 82 (0.47 g, 20% over 2 steps) as a white solid: ¹H NMR (DMSO-d₆, 300 MHz) δ 9.53 (s, 1H), 8.30 (m, 1H), 8.16 (m, 1H), 8.03–8.08 (m, 3H), 7.65–7.7.75 (m, 3H), 7.55 (dd, 1H), 7.20 (d, 1H), 4.82 (s, 2H), 3.65 (m, 1H), 2.20 (s, 3 H), 1.41–1.61 (m, 3H), 0.84 (s, 3H), 0.82 (s, 3H); LC-MS (ES⁺) m/z 631 (M+H)⁺, (ES⁻) m/z 629 (M−H)⁻.

EXAMPLE 26

N¹-{[4-({[4-chloro-2-(3-chloro-5-cyanobenzoyl)phenoxy]acetyl}amino)-3-methylphenyl]sulfonyl}-D-alaninamide

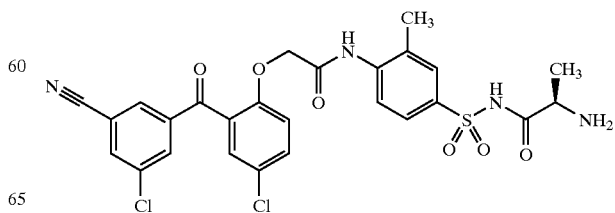

84

Step A:

85

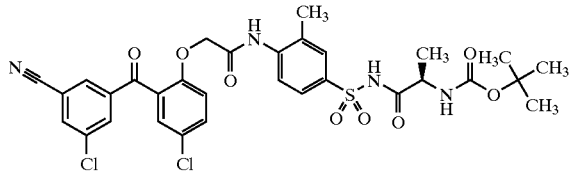

A mixture of 40 (0.2 g, 0.39 mmol), DMAP (Aldrich, 0.1 g, 0.82 mmol), and N-Boc-alanine (Bachem, 0.072 g, 0.38 mmol) in CH$_2$Cl$_2$ (30 mL) was cooled to 0° C. in an ice/water bath. EDAC (Sigma, 0.08 g, 0.38 mmol) was added and the reaction mixture was allowed to warm to rt over 1 h. After 18 h, the reaction was cooled to 0° C. in an ice/water bath, washed with 1 N HCl, the organic layer was separated and was concentrated in vacuo. The concentrate was dissolved in CH$_2$Cl$_2$ and purified by flash chromatography using 5% MeOH/CH$_2$Cl$_2$ to afford 85. The product was used with no further purification.

Step B:

A mixture of 85 and TFA (2 mL) in CH$_2$Cl$_2$ (5 mL) was stirred at rt for 2 h then concentrated in vacuo. Purification by flash chromatography using 5–10% MeOH/CH$_2$Cl$_2$ gave 84 (0.09 g, 40% over 2 steps) as a white solid: $^1$H NMR (CDCl$_3$, 300 MHz) δ 8.68 (s, 1H), 7.80 (m, 2H), 7.55–7.66 (m, 4H), 7.36 (m, 1H), 7.18 (m, 1H), 6.89 (d, 1H), 4.51 (s, 2 H), 3.50 (m, 1H), 2.05 (s, 3H), 1.53 (m, 3H); LC-MS (ES$^+$) m/z 589 (M+H)$^+$, (ES$^-$) m/z 587 (M–H)$^-$.

EXAMPLE 27

N$^1$-{[4-({[4-chloro-2-(3-chloro-5-cyanobenzoyl)phenoxy]acetyl}amino)-3-methylphenyl]sulfonyl}glycinamide

86

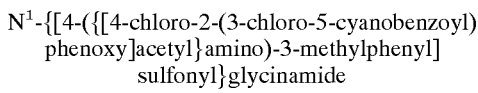

Step A:

87

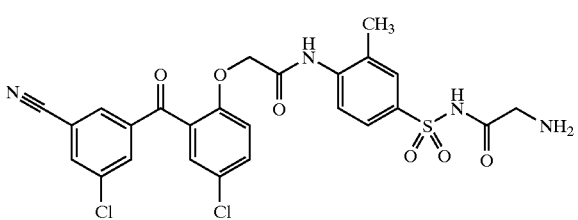

A mixture of 40 (0.2 g, 0.39 mmol), DMAP (Aldrich, 0.1 g, 0.82 mmol), and N-Boc-glycine (Aldrich, 0.067 g, 0.38 mmol) in CH$_2$Cl$_2$ (30 mL) was cooled to 0° C. in an ice/water bath. EDAC (Sigma, 0.08 g, 0.38 mmol) was added and the reaction mixture was allowed to warm to rt over 1 h. After 18 h, the reaction was cooled to 0° C. in an ice/water bath, washed with 1 N HCl, the organic layer was separated and was concentrated in vacuo. The concentrate was dissolved in CH$_2$Cl$_2$ and purified by flash chromatography using 5% MeOH/CH$_2$Cl$_2$ to afford 86. The product was carried on without further purification.

Step B:

A mixture of 86 and TFA (2 mL) in CH$_2$Cl$_2$ (5 mL) was stirred at rt for 2 h then concentrated in vacuo. Purification by flash chromatography using 5–10% MeOH/CH$_2$Cl$_2$ gave 85 (0.12 g, 55% over 2 steps) as a white solid: $^1$H NMR (DMSO-d$_6$, D$_2$O exchange, 300 MHz) δ 9.51 (s, 1H), 8.23 (m, 1H), 8.10 (m, 1H), 8.04 (m, 1H), 7.51–7.70 (m, 4H), 7.19 (d, 1H), 4.78 (s, 2H), 3.47 (s, 2H), 2.15 (s, 3H); LC-MS (ES$^+$) m/z 575 (M+H)$^+$, (ES$^-$) m/z 573 (M–H)$^-$.

EXAMPLE 28

N-{4-[(acetylamino)sulfonyl]-2-methylphenyl}-2-[4-chloro-2-(3-chloro-5-cyanobenzoyl)phenoxy]acetamide, Sodium Salt

88

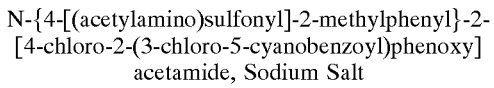

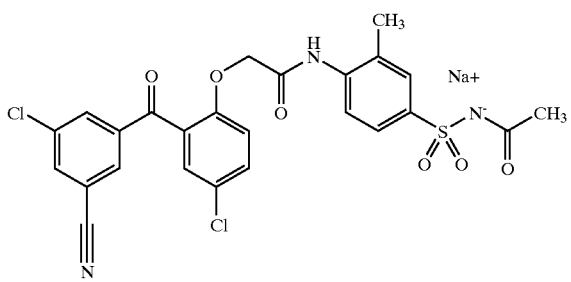

Step A:

89

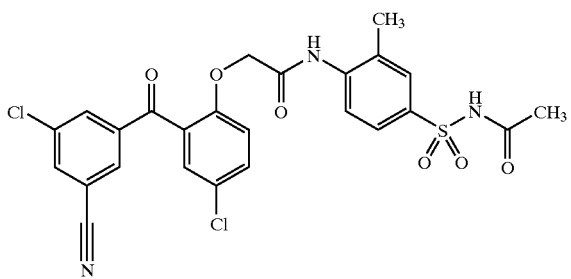

Acetic anhydride (Aldrich, 0.011 mL, 0.117 mmol) was added dropwise to a mixture of 40 (0.05 g, 0.096 mmol) and DMAP (0.012 g, 0.096 mmol) in CH$_2$Cl$_2$ (5 mL) and the resulting solution was stirred at rt. After 2 h, the reaction was cooled to 0° C. and washed twice with 0.5 N HCl. Hexanes (4 mL) was added and the resulting suspension was filtered, washed with Et$_2$O, dried in air, washed with Hexanes, washed with Et$_2$O, then dried under a stream of nitrogen to afford 89 as a white solid (0.024 g, 44%). $^1$H NMR (DMSO-d$_6$, 300 MHz) δ 12.00 (s, 1H), 9.48 (s, 1H), 8.28 (m, 1H), 8.15 (m, 1H), 8.08 (m, 1H), 7.65–7.79 (m, 4H), 7.54 (d, 1H), 7.22 (d, 1H), 4.84 (s, 2H), 2.22 (s, 3H), 1.90 (s, 3H); LC-MS (ES$^+$) m/z 560 (M+H)$^+$, (ES$^-$) m/z 558 (M–H)$^-$.

Step B:

Benzophenone 89 (0.024 g, 0.043 mmol) was combined with 1 N NaOH (0.043 mL, 0.043 mmol) then water (150 mL) was added until the solid dissolved. The resulting solution was lyophilized to afford 88 as an off-white solid (0.032 g, >99%). $^1$H NMR (DMSO-d$_6$, 300 MHz) δ 9.31 (s, 1H), 8.31 (m, 1H), 8.15 (m, 1H), 8.08 (m, 1H), 7.67 (dd, 1H), 7.45–7.53 (m, 3H), 7.36 (d, 1H), 7.22 (d, 1H), 4.78 (s, 2H), 2.10 (s, 3H), 1.60 (s, 3H); LC-MS (ES$^+$) m/z 560 (M+H)$^+$, (ES$^+$) m/z 582 (M+Na)$^+$.

EXAMPLE 29

N-{[4-({[4-chloro-2-(3-chloro-5-cyanobenzoyl)phenoxy]acetyl}amino)-3-methylphenyl]sulfonyl}-1-methylprolinamide, Sodium Salt

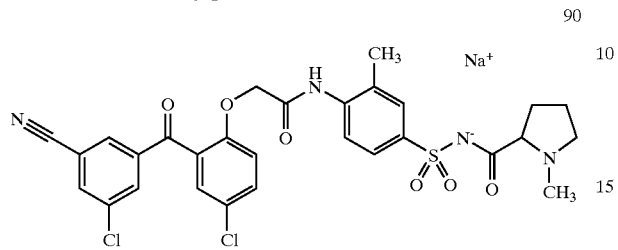

90

Step A:

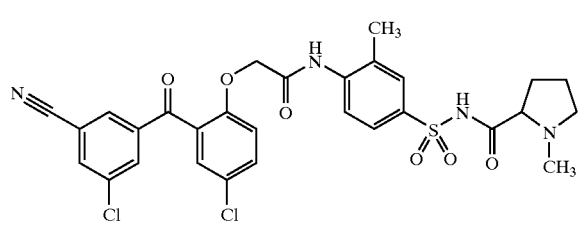

91

A mixture of 40 (0.05 g, 0.096 mmol), DMAP (Aldrich, 0.06 g, 0.49 mmol), and N-methyl-L-proline (Aldrich, 0.065 g, 0.5 mmol) in CH$_2$Cl$_2$ (5 mL) was cooled to 0° C. in an ice/water bath. EDAC (Sigma, 0.04 g, 0.21 mmol) was added and the resulting mixture was allowed to stir for 1 h. After 18 h, the reaction was cooled to 0° C. in an ice/water bath, washed with 1 N HCl, the organic layer was separated and was concentrated in vacuo. The concentrate was dissolved in CH$_2$Cl$_2$ and purified by flash chromatography using 5% MeOH/CH$_2$Cl$_2$ to afford 91 (0.038 g, 12%). $^1$H NMR (DMSO-d$_6$, 300 MHz) δ 9.37 (s, 1H), 9.10 (bs, 1H), 8.31 (m, 1H), 8.16 (m, 1H), 8.12 (m, 1H), 7.53–7.70 (m, 4H), 7.44 (d, 1H), 7.22 (d, 1H), 4.79 (s, 2H), 3.73 (m, 1H), 3.70–3.48 (m, 1H), 2.97 (m, 1H), 2.74 (s, 3H), 2.24–2.29 (m, 1H), 2.13 (s, 3H), 1.68–1.95 (m, 3H); LC-MS (ES$^+$) m/z 629 (M+H)$^+$, (ES$^-$) m/z 627 (M–H)$^-$.

Step B:

Compound 91 (0.038 g, 0.06 mmol) was combined with 1 N NaOH (0.065 mL, 0.065 mmol), water (300 mL), and acetone (5 mL). The resulting solution was lyophilized to afford 90 as an off-white solid (0.040 g, >99%). $^1$H NMR (DMSO-d$_6$, 300 MHz) δ 9.35 (s, 1H), 8.31 (m, 1H), 8.16 (m, 1H), 8.08 (m, 1H), 7.51–7.69 (m, 4H), 7.43 (d, 1H), 7.23 (d, 1H), 4.79 (s, 2H), 3.25 (s, 1H), 3.18 (s, 1H), 2.72 (s, 2H), 2.45 (s, 1H), 2.40 (s, 1H), 2.29 (s, 1H), 2.12 (s, 3H), 1.65–1.82 (m, 3H); LC-MS (ES$^+$) m/z 651 (M+Na)$^+$, (ES$^-$) m/z 629 (M+H)$^+$.

Example 30

2-[4-chloro-2-(3-chloro-5-cyanobenzoyl)phenoxy]-N-(4-{[isobutyryl(methyl)amino]sulfonyl}-2-methylphenyl)acetamide

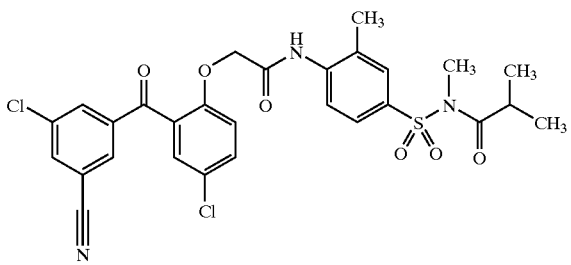

91

Sodium hydride (60% oil suspension, Aldrich, 0.006 g, 0.14 mmol) was added to a mixture of 43 (0.157 g, 0.54 mmol) in DMF (2 mL) at rt. After 10 min, methyl iodide (2 mL) was added and the reaction was stirred overnight at rt. After 18 h, the reaction was warmed to 65° C. After another 5 h, the reaction mixture was poured into water and extracted with CH$_2$Cl$_2$ (3×10 mL). The combined organic layers were loaded onto a silica gel pad and eluted with 1:1 hexanes: EtOAc to afford a white solid 91 (0.023 g, 30%): $^1$H NMR (DMSO-d$_6$, 300 MHz) δ 9.46 (s, 1H), 8.28 (m, 1H), 8.15 (s, 1H), 8.08 (m, 1H), 7.64–7.83 (m, 4H), 7.54 (d, 1 H), 7.23 (s, 1H), 4.84 (s, 2 H), 3.33 (s, 3H), 3.10 (m, 1H), 2.23 (s, 3H), 0.94 (s, 3H), 0.91 (s, 3H); LC-MS (ES$^+$) m/z 602 (M+H)$^+$, (ES$^-$) m/z 600 (M–H)$^-$.

Example 31

2-[4-chloro-2-(3-chloro-5-cyanobenzoyl)phenoxy]-N-(2-methyl-4-{[methyl(propionyl)amino]sulfonyl}phenyl)acetamide

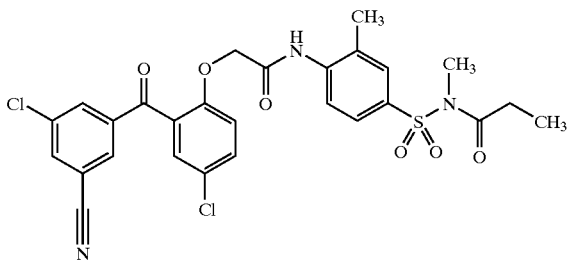

92

Methyl iodide (2 mL) was added to a mixture of 34 (0.033 g, 0.06 mmol) in acetonitrile (2 mL). After 18 h, the reaction mixture was concentrated in vacuo and purified on silica gel, eluting with 1:1 hexanes: EtOAc, to afford 92 as a white solid (0.03 g, 91%). $^1$H NMR (DMSO-d$_6$, 300 MHz) δ 9.46 (s, 1 H), 8.28 (m, 1 H), 8.15 (m, 1H), 8.07 (m, 1H), 7.65–7.81 (m, 4H), 7.53 (m, 1H), 7.22 (s, 1H), 4.83 (s, 2H), 2.56 (s, 3 H), 2.43 (m, 2H), 2.22 (s, 3H), 0.89 (t, 3H); LC-MS (ES$^+$) m/z 588 (M+H)$^+$, (ES$^-$) m/z 586 (M–H)$^-$.

Example 32

N-(4-{[acetyl(methyl)amino]sulfonyl}-2-methylphenyl)-2-[4-chloro-2-(3-chloro-5-cyanobenzoyl)phenoxy]acetamide

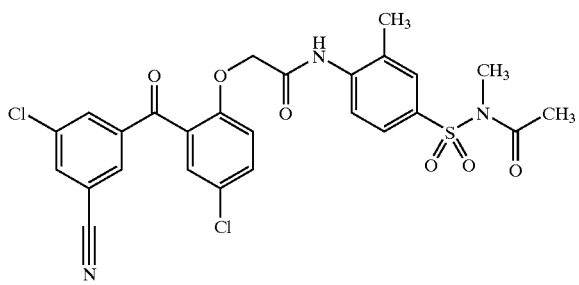

93

A mixture of 89 (0.044 g, 0.79 mmol), pyridine (0.0127 mL, 0.16 mmol), and methyl iodide (0.0074 mL, 0.12 mmol) in THF (4 mL) was stirred in a sealed tube at rt. After 24 h, an additional portion of methyl iodide (0.0074 mL) was added to the reaction mixture. After an additional 24 h, the reaction was concentrated in vacuo and purified on silica gel, eluting with 1:1 hexanes: EtOAc, to afford 93 as an orange solid (0.028 g, 63%). $^1$H NMR (DMSO-d$_6$, 300 MHz) δ 9.47 (s, 1H), 8.29 (m, 1H), 8.15 (m, 1H), 8.08 (m, 1H), 7.65–7.84 (m, 4H), 7.54 (d, 1H), 7.23 (s, 1H), 4.84 (s, 2H), 3.26 (s, 3H), 2.24 (6H); LC-MS (ES$^+$) m/z 574 (M+H)$^+$, (ES$^-$) m/z 572 (M–H)$^-$.

Example 33

2-[4-chloro-2-(3-chloro-5-cyanobenzoyl)phenoxy]-N-{4-[(hexanoylamino)sulfonyl]-2-methylphenyl}acetamide, Sodium Salt

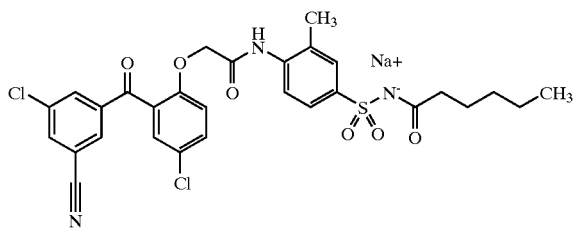

94

Step A:

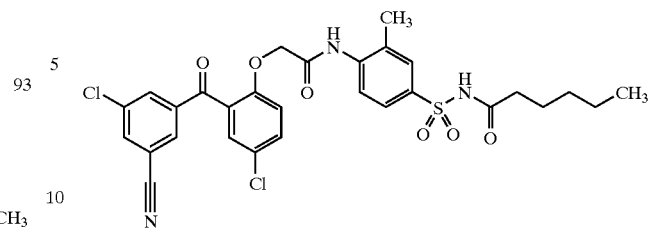

95

Hexanoyl chloride (Aldrich, 0.026 mL, 0.19 mmol) was added dropwise to a mixture of 40 (0.085 g, 0.16 mmol) and DMAP (0.05 g, 0.41 mmol) in CH$_2$Cl$_2$ (6 mL) and the resulting solution was stirred at rt. After 2 h, the reaction was cooled to 0° C., washed with 1 N HCl (2×), water (1×), and brine. The organic layer was separated and concentrated in vacuo. The resulting residue was purified by silica gel TLC prep plate eluted with 1:1 EtOAc: hexanes to afford 95 as a white solid (0.045 g, 45%). $^1$H NMR (DMSO-d$_6$, 300 MHz) δ 11.95 (bs, 1H), 9.47 (s, 1H), 8.28 (m, 1H), 8.15 (m, 1H), 8.07 (m, 1H), 7.64–7.79 (m, 4H), 7.53 (d, 1H), 7.22 (d, 1H), 4.83 (s, 2H), 2.22 (s, 3H), 2.16 (m, 2H), 1.38 (m, 2H), 1.06–1.22 (m, 4H), 0.78 (t, 3H); LC-MS (ES$^+$) m/z 616 (M+H)$^+$, (ES$^-$) m/z 614 (M–H)$^-$.

Step B:

Benzophenone 95 (0.045 g, 0.073 mmol) was combined with 1 N NaOH (0.08 mL, 0.08 mmol), water (400 mL) and 1,4-dioxane (0.5 mL). The resulting solution was lyophilized to afford 94 as an off-white solid (0.039 g, 83%). $^1$H NMR (DMSO-d$_6$, 300 MHz) δ 9.31 (s, 1H), 8.30 (s, 1H), 8.15 (s, 1H), 8.08 (s, 1H), 7.44–7.67 (m, 4H), 7.36 (d, 1H), 7.22 (d, 1H), 4.78 (s, 2H), 2.10 (s, 3H), 1.84 (m, 2H), 1.35 (m, 2H), 1.12–1.22 (m, 4H), 0.81 (t, 3H); LC-MS (ES$^+$) m/z 616 (M+H)$^+$, (ES$^-$) m/z 638 (M+Na)$^+$.

Example 34

2-[4-chloro-2-(3-chloro-5-cyanobenzoyl)phenoxy]-N-{4-[(heptanoylamino)sulfonyl]-2-methylphenyl}acetamide, Sodium Salt

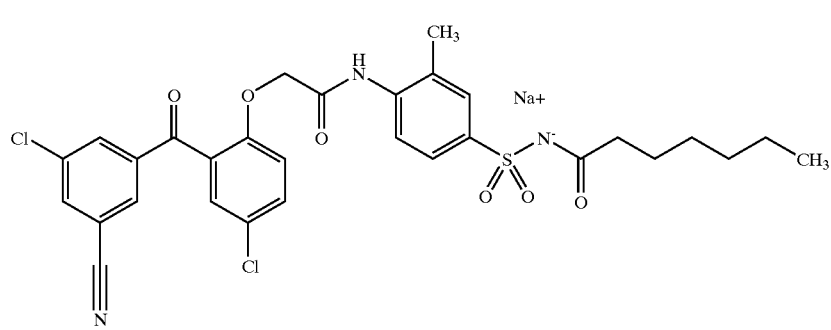

96

Step A:

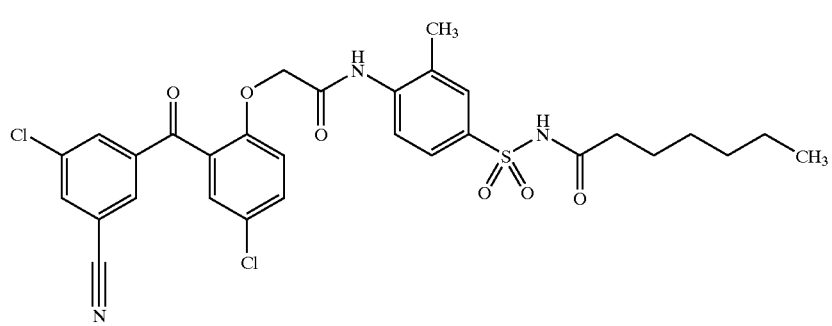

97

Heptanoyl chloride (Aldrich, 0.028 mL, 0.18 mmol) was added dropwise to a mixture of 40 (0.077 g, 0.15 mmol) and DMAP (0.05 g, 0.41 mmol) in $CH_2Cl_2$ (6 mL) and the resulting solution was stirred at rt. After 2 h, the reaction was then cooled to 0° C., washed with 1 N HCl (2×), water (1×) and brine. The organic layer was separated and concentrated in vacuo. The resulting residue was purified by silica gel TLC prep plate eluted with 1:1 EtOAc: hexanes to afford 97 as a white solid (0.058 g, 61%). $^1$H NMR (DMSO-$d_6$, 300 MHz) δ 11.94 (s, 1H), 9.47 (s, 1H), 8.28 (m, 1H), 8.15 (m, 1H), 8.07 (m, 1H), 7.78 (d, 1H), 7.64–7.71 (m, 3H), 7.54 (d, 1H), 7.22 (d, 1H), 4.83 (s, 2H), 2.22 (s, 3H), 2.16 (m, 2H), 1.37 (m, 2H), 1.10–1.22 (m, 5H), 0.79 (m, 3H); LC-MS (ES$^+$) m/z 630 (M+H)$^+$, (ES$^-$) m/z 628 (M–H)$^-$.

Step B:

Benzophenone 97 (0.058 g, 0.092 mmol) was combined with 1 N NaOH (0.10 mL, 0.10 mmol) and water (300 mL). The resulting solution was lyophilized to afford 96 as an off-white solid (0.047 g, 78%). $^1$H NMR (DMSO-$d_6$, 300 MHz) δ 9.31 (s, 1H), 8.30 (m, 1H), 8.15 (m, 1H), 8.08 (m, 1H), 7.67 (dd, 1H), 7.37–7.53 (m, 4H), 7.22 (d, 1H), 4.78 (s, 2H), 2.10 (s, 3H), 1.86 (m, 2H), 1.34 (m, 2H), 1.12–1.25 (m, 7H), 0.82 (m, 3H); LC-MS (ES$^+$) m/z 630 (M+H)$^+$, (ES$^+$) m/z 652 (M+Na)$^+$.

Example 35

2-[4-chloro-2-(3-chloro-5-cyanobenzoyl)phenoxy]-N-{2-methyl-4-[(octanoylamino)sulfonyl]phenyl}acetamide, Sodium Salt

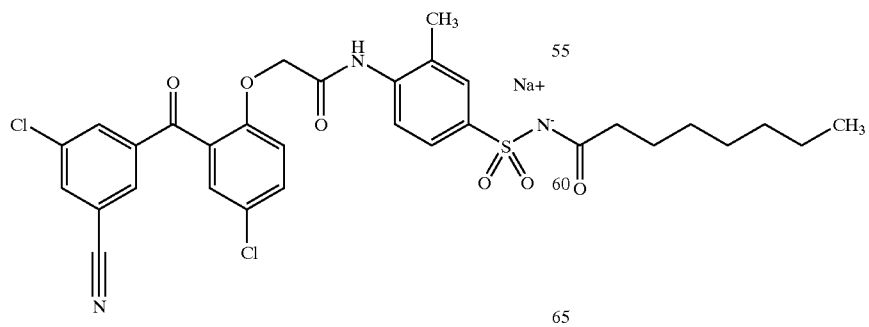

98

Step A:

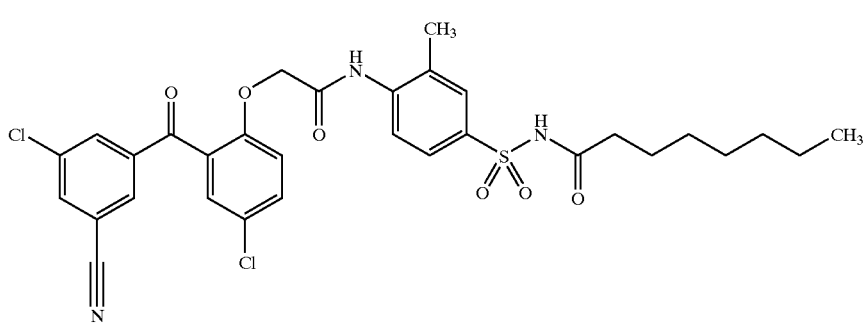

Octanoyl chloride (Aldrich, 0.0304 mL, 0.178 mmol) was added dropwise to a mixture of 40 (0.077 g, 0.15 mmol) and DMAP (0.05 g, 0.41 mmol) in $CH_2Cl_2$ (6 mL) and the resulting solution was stirred at rt. After 2 h, the reaction was then cooled to 0° C., washed with 1 N HCl (2×), water (1×), and brine. The organic layer was then separated and was concentrated in vacuo. The resulting residue was purified by silica gel TLC prep plate eluted with 1:1 EtOAc: hexanes to afford 99 as a white solid (0.044 g, 45%). $^1$H NMR (DMSO-$d_6$, 300 MHz) δ 11.94 (bs, 1H), 9.45 (s, 1H), 8.28 (m, 1H), 8.15 (m, 1H), 8.07 (m, 1H), 7.62–7.76 (m, 4H), 7.53 (d, 1H), 7.22 (d, 1H), 4.83 (s, 2H), 2.21 (s, 3H), 2.11–2.17 (m, 2H), 1.37 (m, 2H), 1.15–1.23 (m, 8H), 0.77–0.85 (m, 3H); LC-MS (ES$^+$) m/z 644 (M+H)$^+$, (ES$^-$) m/z 642 (M–H)$^-$.

Step B:

Benzophenone 99 (0.044 g, 0.068 mmol) was combined with 1 N NaOH (0.075 mL, 0.075 mmol), water (300 mL) and THF (5 mL). The resulting solution was lyophilized to afford 98 as an off-white solid (0.023 g, 51%). $^1$H NMR (DMSO-$d_6$, 300 MHz) δ 9.31 (s, 1H), 8.30 (m, 1H), 8.15 (m, 1H), 8.08 (m, 1H), 7.43–7.69 (m, 4H), 7.36 (d, 1H), 7.22 (d, 1H), 4.78 (s, 2H), 2.10 (s, 3H), 1.84 (m, 2H), 1.16–1.39 (m, 10H), 0.80–0.86 (m, 3H); LC-MS (ES$^+$) m/z 644 (M+H)$^+$, (ES$^+$) m/z 666 (M+Na)$^+$.

Example 36

2-[4-chloro-2-(3-chloro-5-cyanobenzoyl)phenoxy]-N-{2-methyl-4-[(nonanoylamino)sulfonyl]phenyl}acetamide, sodium salt Step A:

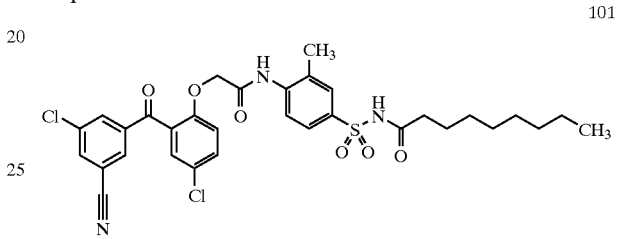

Nonanoyl chloride (Aldrich, 0.038 mL, 0.18 mmol) was added dropwise to a mixture of 40 (0.077 g, 0.15 mmol) and DMAP (0.05 g, 0.41 mmol) in $CH_2Cl_2$ (6 mL) and the resulting solution was stirred at rt. After 2 h, the reaction was then cooled to 0° C., washed with 1 N HCl (2×), water (1×), and brine. The organic layer was then separated and concentrated in vacuo. The resulting residue was purified by silica gel TLC prep plate eluted with 1:1 EtOAc: hexanes to afford 101 as a white solid (0.043 g, 44%). $^1$H NMR (DMSO-$d_6$, 300 MHz) δ 11.94 (s, 1H), 9.46 (s, 1H), 8.27 (m, 1H), 8.15 (m, 1H), 8.07 (m, 1H), 7.78 (d, 1H), 7.64–7.71 (m, 3H), 7.53 (d, 1H), 7.22 (d, 1H), 4.83 (s, 2H), 2.22 (s, 3H), 2.16 (m, 2H), 1.39 (m, 2H), 1.16–1.23 (m, 11H), 0.81 (t, 3H); LC-MS (ES$^+$) m/z 658 (M+H)$^+$, (ES$^-$) m/z 656 (M–H)$^-$.

Step B:

Benzophenone 101 (0.043 g, 0.065 mmol) was combined with 1 N NaOH (0.072 mL, 0.072 mmol) water (350 mL). The resulting solution was lyophilized to afford 100 as an

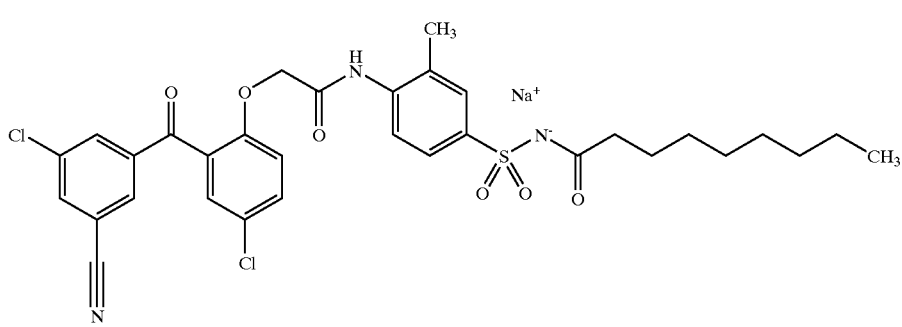

off-white solid (0.037 g, 84%). $^1$H NMR (DMSO-$d_6$, 300 MHz) δ 9.30 (s, 1H), 8.30 (m, 1H), 8.15 (m, 1H), 8.08 (m, 1H), 7.44–7.67 (m, 4H), 7.36 (d, 1H), 7.22 (d, 1H), 4.78 (s, 2H), 2.10 (s, 3H), 1.84 (m, 2H), 1.20–1.38 (m, 14H), 0.81–0.85 (m, 3H); LC-MS (ES$^+$) m/z 658 (M+H)$^+$, (ES$^+$) m/z 680 (M+Na)$^+$.

Example 37

Isopropyl [4-({[4-chloro-2-(3-chloro-5-cyanobenzoyl)phenoxy]acetyl}amino)-3-methylphenyl]sulfonylcarbamate, Sodium Salt

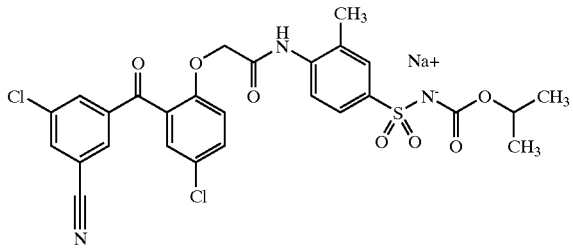

102

Step A:

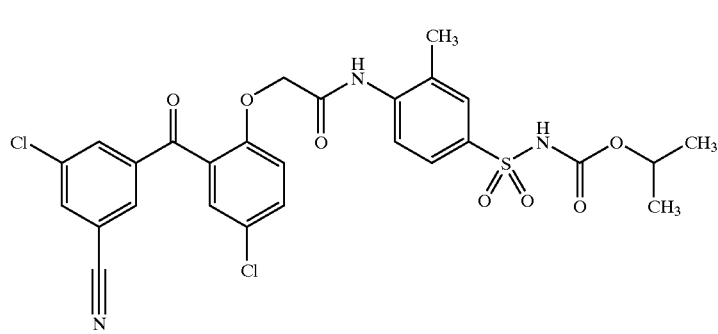

103

Isopropyl chloroformate (1.0 M in Toluene, Aldrich, 0.24 mL, 0.24 mmol) was added dropwise to a mixture of 40 (0.1 g, 0.2 mmol) and DMAP (0.024 g, 0.19 mmol) in CH$_2$Cl$_2$ (6 mL) and the resulting solution was stirred at rt. After 3 h, the reaction was cooled to 0° C. and washed with 1 N HCl (2×). Hexane was added to the cloud point and the resulting suspension was cooled to 0° C. for 15 min, filtered, washed with cold 1:1 CH$_2$Cl$_2$:hexanes (8 mL) and air dried. The resulting solid was dissolved in CH$_2$Cl$_2$, cooled to 0° C., and washed with 0.5 M NaOH. The aqueous layer was acidified with 1 N HCl, extracted with CH$_2$Cl$_2$, the organic layer was separated, dried over MgSO$_4$, filtered and concentrated in vacuo to afford 103 as a yellow glass (0.042 g, 36% crude yield). The product was carried on without further purification. LC-MS (ES$^+$) m/z 604 (M+H)$^+$, (ES$^-$) m/z 602 (M-H)$^-$.

Step B:

Benzophenone 103 (0.042 g, 0.07 mmol) was combined with 1 N NaOH (0.076 mL, 0.076 mmol) and water (50 mL). The resulting solution was lyophilized to afford 102 as an off-white solid (0.028 g, 64%). $^1$H NMR (DMSO-$d_6$, 300 MHz) δ 9.32 (s, 1H), 8.30 (m, 1H), 8.15 (m, 1H), 8.08 (m, 1H), 7.67 (dd, 1H), 7.51–7.53 (m, 2H), 7.46 (dd, 1H), 7.38 (d, 1H), 7.22 (d, 1H), 4.78 (s, 2H), 3.66 (q, 2H), 2.11 (s, 3H), 1.00 (t, 3H); LC-MS (ES$^+$) m/z 612 (M+H)$^+$, (ES$^-$) m/z 610 (M-H)$^-$.

Example 38

Ethyl [4-({[4-chloro-2-(3-chloro-5-cyanobenzoyl)phenoxy]acetyl}amino)-3-methylphenyl]sulfonylcarbamate, Sodium Salt

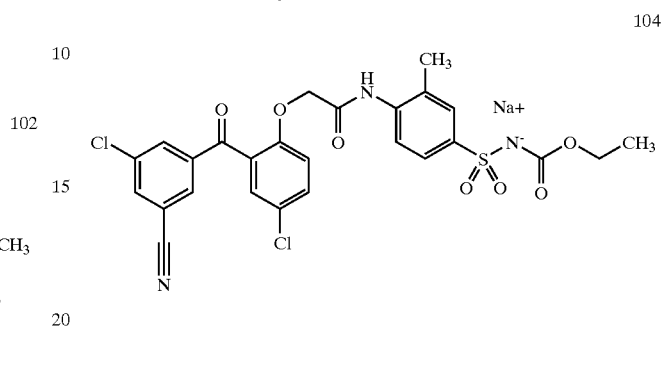

104

Step A:

105

Ethyl chloroformate (Aldrich, 0.022 mL, 0.23 mmol) was added dropwise to a mixture of 40 (0.1 g, 0.2 mmol) and DMAP (0.024 g, 0.19 mmol) in CH$_2$Cl$_2$ (6 mL) and the resulting solution was stirred at rt. After 1 h, the reaction was washed with 1 N HCl (2×), hexane (6 mL) was added. The resulting suspension was cooled to 0° C. for an hour, filtered, washed with Et$_2$O, and air-dried to afford 105 as a white solid (0.095 g, 83%). $^1$H NMR (DMSO-$d_6$, 400 MHz) δ 11.91 (bs, 1H), 9.49 (s, 1H), 8.28 (m, 1H), 8.16 (s, 1H), 8.07 (s, 1H), 7.79 (d, 1H), 7.71 (m, 1H), 7.67 (dd, 2H), 7.54 (d, 1H), 7.23 (d, 1H), 4.84 (s, 2H), 4.00 (q, 2H), 2.22 (s, 3H), 1.10 (t, 3H).

Step B:

Benzophenone 105 (0.095 g, 0.161 mmol) was combined with 1 N NaOH (0.177 mL, 0.177 mmol) and water (180 mL). The resulting solution was lyophilized to afford 104 as a white solid (0.083 g, 85%). $^1$H NMR (DMSO-$d_6$, 300 MHz) δ 9.32 (s, 1H), 8.30 (m, 1H), 8.15 (m, 1H), 8.08 (m, 1H), 7.67 (dd, 1H), 7.51–7.53 (m, 2H), 7.46 (dd, 1H), 7.38 (d, 1H), 7.22 (d, 1H), 4.78 (s, 2H), 3.66 (q, 2H), 2.11 (s, 3H), 1.00 (t, 3H); LC-MS (ES$^+$) m/z 612 (M+H)$^+$, (ES$^-$) m/z 610 (M-H)$^-$.

Example 39

Methyl [4-({[4-chloro-2-(3-chloro-5-cyanobenzoyl)phenoxy]acetyl}amino)-3-methylphenyl]sulfonylcarbamate, Sodium Salt

106

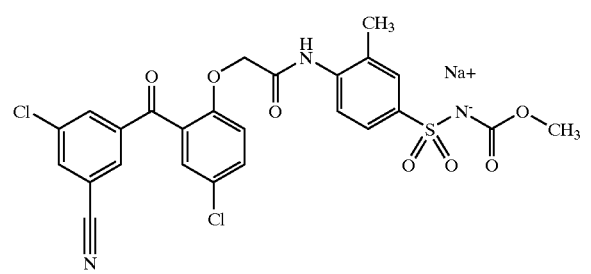

Step A:

107

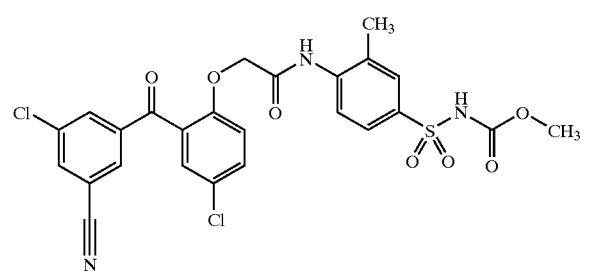

Methyl chloroformate (Acros, 0.018 mL, 0.23 mmol) was added dropwise to a mixture of 40 (0.1 g, 0.2 mmol) and DMAP (0.024 g, 0.19 mmol) in CH$_2$Cl$_2$ (6 mL) and the resulting solution was stirred at rt. After 1 h, the reaction was washed with 1 N HCl (2x), and hexane (6 mL) was added. The resulting suspension was cooled to 0° C. for 1 h, filtered, washed with Et$_2$O, and air-dried to afford 107 as a white solid (0.102 g, 87%). $^1$H NMR (1) DMSO-$d_6$, 300 MHz) δ 12.00 (s, 1H), 9.50 (s, 1H), 8.29 (s, 1H), 8.16 (m, 1H), 8.07 (m, 1H), 7.79 (d, 1H), 7.65–7.71 (m, 3H), 7.54 (d, 1H), 7.23 (d, 1H), 4.84 (s, 2H), 3.56 (s, 3H), 2.23 (s, 3H).

Step B:

Benzophenone 107 (0.097 g, 0.168 mmol) was combined with 1 N NaOH (0.185 mL, 0.185 mmol) and water (200 mL). The resulting solution was lyophilized to afford 106 as an off-white solid (0.082 g, 82%). $^1$H NMR (DMSO-$d_6$, 300 MHz) δ 9.32 (s, 1H), 8.31 (m, 1H), 8.15 (m, 1H), 8.08 (m, 1H), 7.67 (dd, 1H), 7.51–7.53 (m, 2H), 7.46 (dd, 1H), 7.38 (d, 1H), 7.22 (d, 1H), 4.78 (s, 2H), 3.23 (s, 3H), 2.11 (s, 3H); LC-MS (ES$^+$) m/z 598 (M+H)$^+$, (ES$^-$) m/z 596 (M-H)$^-$.

Example 40

2-[4-chloro-2-(3-chloro-5-cyanobenzoyl)phenoxy]-N-{2-methyl-4-[(propionylamino)sulfonyl]phenyl}acetamide, Sodium Salt

34

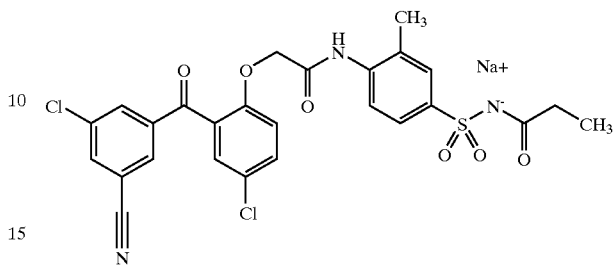

Step A:

35

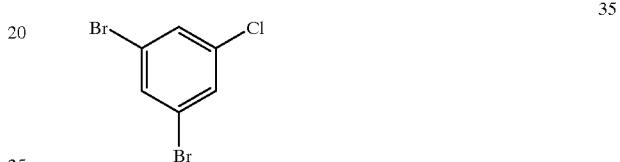

A solution of 1,3,5-tribromobenzene (9.44 g, 30 mmol) in 120 mL of ether was cooled to −78° C. in a dry ice/acetone bath. n-Butyllithium (13.2 mL of 2.5 M solution in hexanes, 33 mmol) was added dropwise over 10 min. The resulting mixture was stirred at −78° C. for an additional 10 min, then hexachloroethane (7.15 g, 30.2 mmol) was added in small portions over 3 min. The reaction mixture was then stirred for 15 min at −78° C., followed by 3.2 h at rt. The mixture was partitioned between 100 mL of water and 100 mL of EtOAc. The aqueous layer was separated and extracted with an additional 100 mL of EtOAc. The combined organic layers were then dried over MgSO$_4$, filtered, and concentrated in vacuo to give 35 as a pale brown solid (7.72 g, 95%). $^1$H NMR (CDCl$_3$, 300 MHz) δ 7.57 (t, 1 H), 7.47 (d, 2 H).

Step B:

36

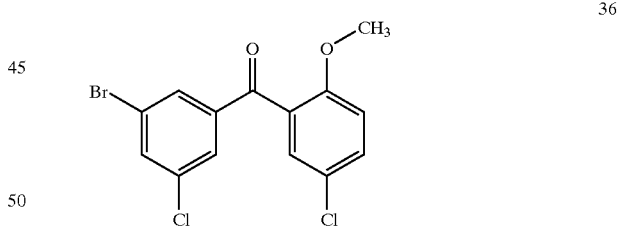

A reactor (reactor 1) was charged with amide 7 (1.0 wt) and methyl tert-butyl ether (MTBE, 12 vol). A separate reactor (reactor 2) was charged with 35 (1.76 wt) and MTBE (12 vol). The reactors were cooled to −50° C. and n-BuLi (2.5 M, 2.08 vol) was added to reactor 1 at a rate to maintain temperature at less than −40° C. When the addition was complete, the reaction was stirred for an additional 5 min. The slurried contents of reactor 2 were transferred rapidly to reactor 1 by vacuum transfer line. The temperature was allowed to rise to 5° C. over 60 min and 4N HCl (2.1 vol) was stirred into the mixture. After 5 min, stirring was stopped and the phases were allowed to separate. The aqueous phase was discarded. A second portion of 4N HCl (2.1 vol) was added, the mixture was stirred, allowed to separate and the aqueous phase was discarded. The mixture was then heated until 14 volumes was removed. Heptane (9 vol) was added and distillation was continued until the internal temperature reached 83° C. (at this point the solvent ratio was 14% MTBE/86% heptane). The temperature was allowed to rise to 20° C. over 8 h. The mixture was cooled to 0° C. for 1 h, the product was collected by filtration, and was washed with a minimum volume of heptane. The product was dried at 45° C. for 16 h in vacuo to afford 36 (72–85%). $^1$H NMR (CDCl$_3$, 300 MHz) δ 7.76 (t, 1H), 7.70 (t, 1 H), 7.65 (t, 1 H), 7.47 (dd, 1 H), 7.36 (d, 1 H), 6.95 (d, 1 H), 3.72 (s, 3 H).

Step C:

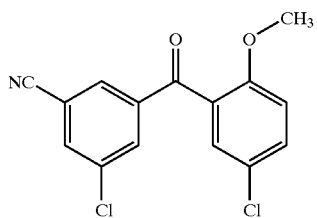

37

This procedure is a modification of that described by Maligres et al [Tet Letters 40, (1999), 8193]. DMF (5.0 vol) was degassed for 1 h using a slow stream of argon gas well dispersed into the solvent via a sub-surface gas dispersion tube. A second reactor, also fitted with a gas dispersion tube, was thoroughly purged with nitrogen, and is charged with 36 (1.0 wt), Zn(CN)$_2$ (0.183 wt) and 1,1-bis(diphenylphosphino)ferrocene (0.012 wt). Tris(dibenzylideneacetone)dipalladium(0) chloroform adduct (0.009 wt) was dissolved in a portion of the de-gassed DMF (~0.01 vol). The reactor was charged with the balance of the de-gassed DMF and the Pd catalyst/DMF mixture was added to the stirred reaction mixture. Sub-surface argon sparging was initiated and the mixture was warmed to 70° C. over 1 h. The mixture was stirred for 3–5 h until remaining starting material constituted less than <1% by LC. The mixture was cooled to 0° C. and a solution consisting of water (4.5 vol), saturated aqueous NH$_4$Cl (3.6 vol) and concentrated NH$_4$OH (0.9 vol) was added at a rate such that internal temperature was maintained below 20° C. After stirring for 1 h the reaction mixture was filtered and the filter cake was washed with a total of 3 volumes of water and suctioned dry. The resulting solid was suspended in water (4 vol) and filtered. The filter cake was re-suspended in methanol—water (9:1) (3 vol) and collected on medium filter paper. The filter cake was rinsed twice with cold (0° C.) methanol (2 vol each). The resulting cake was transferred to a drying oven and dried under vacuum at 45° C. for 40 h to afford 37 (93%). $^1$H NMR (CDCl$_3$, 400 MHz) δ 7.93 (t, 1 H), 7.82 (t, 1 H), 7.76 (t, 1 H), 7.47 (dd, 1 H), 7.37 (d, 1H), 6.93 (d, 1 H), 3.67 (s, 3 H).

Step D:

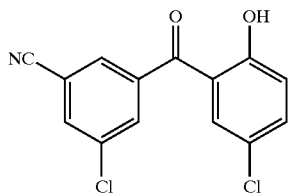

38

To a reactor were added 37 (1.0 wt) and dichloromethane (1.8 vol). Neat BBr$_3$ (0.424 wt) was added at such a rate as to maintain the reaction temperature ≦35° C. The temperature was kept >28° C. for most of the addition to maintain solution. The reaction mixture was held at 30–35° C. for about 10 min and reaction progress was monitored by LC. The mixture was allowed to cool to near rt, and during this time crystallization of the orange borate ester occurred. To the precipitate was added 2-propanol (3.6 vol), while the temperature was maintained at ≦32° C. The mixture was cooled to 0° C. and was allowed to stir for 30 min. The solid was collected, washed with isopropanol (1.5 vol), and allowed to dry under vacuum overnight at 50–60° C. to afford 38 (93%). $^1$H NMR (CDCl$_3$, 400 MHz) δ 11.43 (s, 1 H), 7.84–7.82 (m, 2 H), 7.78 (t, 1 H), 7.49 (dd, 1 H), 7.34 (d, 1 H), 7.05 (d, 1H).

Step E:

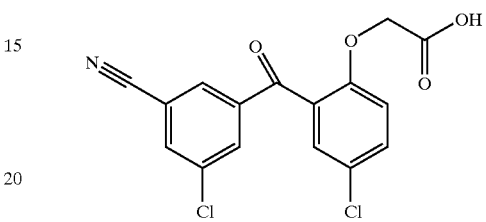

39

A reaction vessel was charged with 38 (1.0 wt), potassium carbonate (1.57 equiv, 0.74 wt), and THF (5.0 vol). The resulting mixture was heated to about 50° C., and ethyl bromoacetate (1.53 equiv, 0.87 wt) was added. The mixture was allowed to stir at 50° C. and was monitored by LC. The mixture was filtered, and the filter cake was washed with hot THF (3.0 vol). Water (20 vol) was added to the mixture and it was cooled to –5° C. Lithium hydroxide monohydrate (2.0 equiv, 0.28 wt) was added and the resulting mixture was stirred at 0° C. for about 60 min. The mixture was acidified by the addition of 1.5 N HCl (6–7 vol) to bring the pH to about 4.5. The layers were separated and the lower layer was concentrated under vacuum to approximately one-third volume. Isopropanol (4 vol) was added and the mixture was concentrated under vacuum to approximately one-third volume. Water (7 vol) was added and the resulting mixture was stirred rapidly for 1.5 h, cooled to 0–5° C. for 30 min and filtered. The filter cake was washed with hot water (50° C., 6 vol) and dried under vacuum to constant weight at 40–60° C. to afford 39 (88–89%). $^1$H NMR (DMSO-d$_6$, 300 MHz) δ 13.19 (broad s, 1 H), 8.32 (s, 1 H), 8.12 (s, 1 H), 8.06 (s, 1 H), 7.63 (dd, 1 H), 7.51 (d, 1 H), 7.15 (d, 1 H), 4.70 (s, 2 H).

Step F:

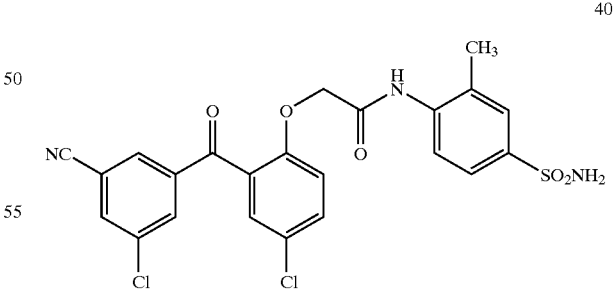

40

A reactor was charged with 39 (1 wt, 1 eq) and dry acetonitrile (10 vol). The mixture was heated to 35° C. and oxalyl chloride (0.362 wt, 1 eq) was slowly added over a period of about 1 h. After 30 min, the completeness of reaction was checked and the presence of unreacted oxalyl chloride was checked. More oxalyl chloride was added if needed. Upon completion of the reaction, excess oxalyl chloride was removed by the application of vacuum (420 mbar) with a nitrogen bleed through the reactor dome. The resulting mixture was cooled to 20° C. and 5 was added as a solid (0.638 wt, 1.2 eq). Vacuum was applied to the reactor (420 mbar) and the reaction mixture was heated to reflux (approx. 55° C.) until conversion to 40 was complete, as evidenced by LC. The mixture was cooled to 20° C., water was added (2 vol), and the resulting mixture was allowed to stir for 30 min. The mixture was then filtered, the solid was washed with acetonitrile (2 vol), and allowed to dry in vacuo at 60° C. (92–96%). $^1$H NMR (DMSO-d$_6$, 400 MHz) δ 9.42 (s, 1 H), 8.26 (s, 1 H), 8.11 (s, 1 H), 8.03 (t, 1 H), 7.63 (dd, 1 H), 7.60–7.53 (m, 3 H), 7.49 (d, 1 H), 7.22 (s, 2 H), 7.19 (d, 1H), 4.77 (s, 2 H), 2.14 (s, 3 H).

Step G:

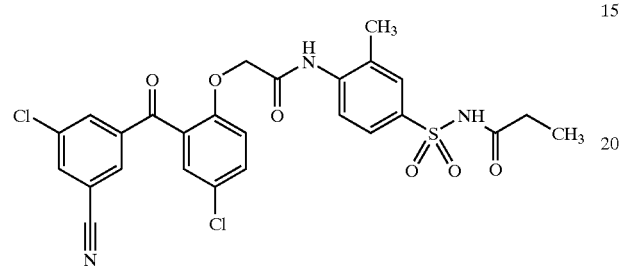

41

Compound 40 (1.0 wt) was suspended in acetonitrile (16 wt), and propionic anhydride (1.0 wt) was added in one portion. The resulting white suspension was heated 60° C. over a period of 60 min, after which time sulfuric acid (0.0022 vol) was added in one portion. The internal temperature was maintained at 60° C. for 2 h. The mixture was allowed to cool to 20° C. over a period of 60 min. The reaction was deemed complete by HPLC (<1% 40 remaining). Upon completion, the mixture was brought to 20° C. over a period of 60 min. After 2 h at 20° C., the mixture was filtered, the filter cake was rinsed with acetonitrile (3×4.0 wt), and dried under N$_2$ at 75° C. in vacuo (ca. 5 mm Hg, 127 Torr) (90–95%) to afford 41. $^1$H NMR (DMSO-d$_6$, 300 MHz) δ 11.93 (bs, 1H), 9.44 (s, 1H), 8.28 (s, 1H), 8.15 (m, 1H), 7.62–7.69 (m, 4H), 7.53 (d, 1H), 7.22 (d, 1H), 4.82 (s, 2H), 2.20 (s, 3H), 2.13 (m, 2H), 0.86 (t, 3H); LC-MS (ES$^+$) m/z 574 (M+H)$^+$, (ES$^-$) m/z 572 (M–H)$^-$.

Step H:

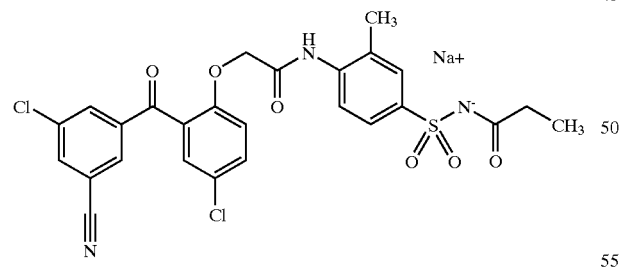

34

To a reaction vessel were added 41 (1.0 wt), sodium carbonate (0.203 wt), acetone (7.9 wt), and DMSO (0.44 wt). The mixture was heated to 55° C. over a period of 1 h, stirred at this temperature for 3–4 h, and was allowed cooled to 40° C. over 20 min. The mixture was filtered (clarifying filtration) into a second reactor (jacket temperature=55° C.) and rinsed with acetone (2×0.79 wt). The filtrate was heated to 55° C., treated with filtered toluene (6.9 wt) while maintaining the internal temperature above 50° C., causing the product to precipitate. The mixture was held at 55° C. for 3 h. The mixture was allowed to cool to 20° C. over 1 h, held at this temperature for 3 h, filtered and rinsed with EtOAc (2×4.5 wt, filtered). The filter cake was dried in the filter funnel and then re-charged into a second reactor, to which ethyl acetate was added (9.0 wt, filtered). The resulting white slurry was heated to 55° C. over a period of 1 h, held at this temperature for 3 h, was allowed to cool to 20° C. over 1 h, was held at this temperature for 3 h, filtered and rinsed with EtOAc (2×4.5 wt, filtered). The filter cake was air-dried in the filter funnel, transferred to a vacuum oven at dried 90° C., and placed under a slight bleed of nitrogen in vacuo (85%) to afford 34. $^1$H NMR (DMSO-d$_6$, 300 MHz) δ 9.32 (s, 1H), 8.30 (s, 1H), 8.14 (s, 1H), 8.08 (s, 1H), 7.67 (dd, 1H), 7.46–7.53 (m, 3H), 7.36 (d, 1H), 7.22 (d, 1H), 4.78 (s, 2H), 2.10 (s, 3H), 1.88 (q, 2H), 0.83 (t, 3H).

Example 41

2-[4-chloro-2-(3-chloro-5-cyanobenzoyl)phenoxy]-N-{2-methyl-4-[(propionylamino)sulfonyl]phenyl}acetamide, Sodium Salt, Form 9

2-[4-chloro-2-(3-chloro-5-cyanobenzoyl)phenoxy]-N-{2-methyl-4-[(propionylamino)sulfonyl]phenyl}acetamide (1.0 wt) and sodium carbonate (0.203 wt) were suspended in acetone (7.9 wt) and DMSO (0.44 wt), and the mixture was heated to 55° C. over a period of 1 h. After 3–4 h, the mixture was cooled to 40° C. over 20 min, filtered and placed into a second reaction vessel and rinsed with acetone (2×0.79 wt). The pale yellow filtrate was heated to 55° C. and then treated with toluene (6.9 wt) while maintaining the temperature above 50° C. When crystallization began to occur, the mixture was held at 55° C. for 3 h. The mixture was heated to 20° C. over 1 h, held at this temperature for 3 h, filtered, and rinsed with EtOAc (2×4.5 wt). The filter cake was dried in the filter funnel. The material was placed into another reactor, along with ethyl acetate (9.0 wt). The resulting white slurry was heated to 55° C. over a period of 1 h, and held at this temperature for 3 h. The mixture was cooled to 20° C. over 1 h, held at this temperature for 3 h, filtered, and rinsed with EtOAc (2×4.5 wt). The filter cake was air-dried in the filter funnel, and then transferred to a vacuum oven, where the product was dried at 90° C. under a slight bleed of nitrogen in vacuo (ca. 5 mm Hg, 127 Torr) (80–82%). $^1$H NMR (DMSO-d$_6$, 300 MHz) δ 9.32 (s, 1H), 8.30 (s, 1H), 8.14 (s, 1H), 8.08 (s, 1H), 7.67 (dd, 1H), 7.46–7.53 (m, 3H), 7.36 (d, 1H), 7.22 (d, 1H), 4.78 (s, 2H), 2.10 (s, 3H), 1.88 (q, 2H), 0.83 (t, 3H).

Example 42

2-[4-chloro-2-(3-chloro-5-cyanobenzoyl)phenoxy]-N-{2-methyl-4-[(propionylamino)sulfonyl]phenyl}acetamide, Sodium Salt, Form 10

In a 10 mL round-bottom flask, 2-[4-chloro-2-(3-chloro-5-cyanobenzoyl)phenoxy]-N-{2-methyl-4-[(propionylamino)sulfonyl]phenyl}acetamide (100 mg) and Na$_2$CO$_3$ (37 mg) were suspended in acetone (2.0 mL) and DMSO (100 μL), and the flask was heated to 55° C. for 1 h. The mixture was cooled to rt, filtered, and the cake rinsed with acetone (1.0 mL). The filtrate was heated to 55° C. and treated with diisopropyl ether (2.0 mL) until cloudiness appeared. Acetone (1.0 mL) was added which rendered the mixture homogeneous. After several hours, more diisopropyl ether (0.5 mL; total=2.5 mL) was added to induce cloudiness. Isopropyl alcohol (500 μL) was added to render the mixture homogeneous followed by more diisopropyl ether (0.9 mL; total=3.4 mL) to induce cloudiness. The mixture had returned to a homogeneous state. More diisopropyl ether (1.7 mL; total=4.2 mL) and isopropyl alchohol (500 μL; total=1.0 mL) were added and the mixture was again stirred overnight at 55° C. A white precipitate formed along the walls of the flask. Vigorous shaking of the flask by hand broke up most of the precipitate, which then dispersed throughout the mixture. More diisopropyl ether (1.0 mL; total=5.2 mL) was added and the mixture was cooled to ambient temperature, filtered though a fritted funnel, and rinsed several times with tert-butyl methyl ether. The solid was dried in a vacuum oven (ca. 20 in Hg) under a bleed of $N_2$ at 80° C. to afford 76 mg (73%) of the title compound.

Example 43

2-[4-chloro-2-(3-chloro-5-cyanobenzoyl)phenoxy]-N-{2-methyl-4-[(propionylamino)sulfonyl]phenyl}acetamide, Sodium Salt, Form 12

A flask was charged with 2-[4-chloro-2-(3-chloro-5-cyanobenzoyl)phenoxy]-N-{2-methyl-4-[(propionylamino)sulfonyl]phenyl}acetamide (1 wt) and THF (10 vol). Sodium tert-butoxide (1.03 eq., 0.17 wt), dissolved in isopropyl alcohol (4 vol)/THF (1 vol), was added dropwise over 10 min. The solution was stirred for 10 min at rt and metyl isobutyl ketone (MEBK, 10 vol) was added, along with a crystal (0.3%). The resulting mixture was allowed to stir at rt for 3 h and was then filtered. The cake was washed with MIBK (5 vol) and partially dried on the filter. Further drying under reduced pressure (20 in Hg) at 75° C. yielded the title compound (80–91%).

Example 44

2-[4-chloro-2-(3-chloro-5-cyanobenzoyl)phenoxy]-N-{2-methyl-4-[(propionylamino)sulfonyl]phenyl}acetamide, Potassium Salt A flask was charged with 2-[4-chloro-2-(3-chloro-5-cyanobenzoyl)phenoxy]-N-{2-methyl-4-[(propionylamino)sulfonyl]phenyl}acetamide (1 wt), $K_2CO_3$ (1.5 eq, 0.36 wt), and acetonitrile (14 vol). The mixture was heated to 70° C. and was stirred for 0.5 h. The suspension was allowed to cool to rt and was filtered into clean flask. Isopropyl alcohol (10 vol) and a seed of pre-formed potassium salt were added. The resulting suspension was allowed to stir at rt overnight. The solid was isolated by filtration and the cake was washed with isopropyl alcohol (3 vol). The cake was partially dried on the filter under $N_2$ and then further dried further under reduced pressure (20 in Hg) at 90° C. to afford the title compound (57%).

Example 45

2-[4-chloro-2-(3-chloro-5-cyanobenzoyl)phenoxy]-N-{2-methyl-4-[(propionylamino)sulfonyl]phenyl}acetamide, Choline Salt, Form I 2-[4-chloro-2-(3-chloro-5-cyanobenzoyl)phenoxy]-N-{2-methyl-4-[(propionylamino)sulfonyl]phenyl}acetamide (20.00 g) was suspended in THF (8.0 Vol) and deionized water (0.16 Vol). The resulting suspension was heated to 50° C. over a period of 30 min. When this temperature was reached, aqueous choline bicarbonate solution (75%, 0.37 Vol) was added over a period of 5 min. Upon completion of base addition the internal temperature was maintained at 50° C. for 30 min. During this time, the reaction mixture turned homogeneous of pale yellow color and the gas evolution ceased. The mixture was then diluted with THF (12 Vol) at a rate to maintain the batch temperature above 45° C. Within 1 h a heavy white precipitate formed, and stirring was continued for an additional 1 h. The mixture was allowed to cool to 20° C. over a period of 60 min. After 2 h at 20° C., the mixture was filtered and the filter cake rinsed with THF (3×5.0 Vol). The isolated material was dried under $N_2$ at 50° C. in vacuo to afford the title compound (87–92%). $^1$H NMR (300 MHz) δ 9.32 (s, 1H), 8.31 (dd, 1H, J=2.2, 1.4 Hz), 8.16 (t, 1H, J=1.4 Hz), 8.08 (dd, 1H, J=2.2, 1.4 Hz), 7.67 (dd, 1H, J=8.8, 2.8 Hz), 7.53 (bd, 2H, J=2.8 Hz), 7.47 (dd, 1H, J=8.3, 2.2 Hz), 7.36 (d, 1H, J=8.3 Hz), 7.23 (d, 1H, J=8.8 Hz), 5.32 (s, 1H), 4.78 (s, 2H), 3.84–3.79 (m, 2H), 3.40–3.36 (m, 2H), 3.09 (s, 9H), 2.10 (s, 3H), 1.88 (q, 2H, J=7.5 Hz), 0.82 (t, 3H, J=7.5 Hz).

Example 46

2-[4-chloro-2-(3-chloro-5-cyanobenzoyl)phenoxy]-N-{2-methyl-4-[(propionylamino)sulfonyl]phenyl}acetamide, Choline Salt, Form 1

2-[4-chloro-2-(3-chloro-5-cyanobenzoyl)phenoxy]-N-{2-methyl-4-[(propionylamino)sulfonyl]phenyl}acetamide (20.00 g) was suspended in THF (8.0 Vol) and deionized water (0.16 Vol). The resulting suspension was heated to 50° C. over a period of 30 min. When this temperature was reached, aqueous choline bicarbonate solution (75%, 0.37 Vol) was added over a period of 5 min. Upon completion of base addition the internal temperature was maintained at 50° C. for 30 min. During this time, the reaction mixture turned homogeneous of pale yellow color and the gas evolution ceased. The mixture was then diluted with THF (12 Vol) at a rate to maintain the batch temperature above 45° C. Upon completion of addition, seed crystals of the choline salt were added. Within 1 h a heavy white precipitate formed, and stirring was continued for an additional 1 h. The mixture was allowed to cool to 20° C. over a period of 60 min. After 2 h at 20° C., the mixture was filtered and the filter cake rinsed with THF (3×5.0 Vol). The isolated material was dried under $N_2$ at 50° C. in vacuo to afford the title compound (87–92%). $^1$H NMR (300 MHz) δ 9.32 (s, 1H), 8.31 (dd, 1H, J=2.2, 1.4 Hz), 8.16 (t, 1H, J=1.4 Hz), 8.08 (dd, 1H, J=2.2, 1.4 Hz), 7.67 (dd, 1H, J=8.8, 2.8 Hz), 7.53 (bd, 2H, J=2.8 Hz), 7.47 (dd, 1H, J=8.3, 2.2 Hz), 7.36 (d, 1H, J=8.3 Hz), 7.23 (d, 1H, J=8.8 Hz), 5.32 (s, 1H), 4.78 (s, 2H), 3.84–3.79 (m, 2H), 3.40–3.36 (m, 2H), 3.09 (s, 9H), 2.10 (s, 3H), 1.88 (q, 2H, J=7.5 Hz), 0.82 (t, 3H, J=7.5 Hz).

Example 47

2-[4-chloro-2-(3-chloro-5-cyanobenzoyl)phenoxy]-N-{2-methyl-4-[(propionylamino)sulfonyl]phenyl}acetamide, Calcium Salt, Form 3

Into a flask were placed 2-[4-chloro-2-(3-chloro-5-cyanobenzoyl)phenoxy]-N-{2-methyl-4-[(propionylamino)sulfonyl]phenyl}acetamide (500 mg), calcium acetylacetonate hydrate (124 mg), and THF (15 mL). The flask was heated to 55° C., during which time, the mixture became extremely thick. MTBE (5 mL) was added to facilitate stirring, after which the mixture was heated at 55° C. was allowed to stir overnight. The mixture was then allowed to cool to ambient temperature (20° C.), filtered, and washed three times with MTBE. The white solid was dried in a vacuum oven (ca. 18" Hg) under a bleed of $N_2$ at 75° C. overnight to afford the title compound (86%).

Example 48

2-[4-chloro-2-(3-chloro-5-cyanobenzoyl)phenoxy]-N-{2-methyl-4-[(propionylamino)sulfonyl]phenyl}acetamide, Calcium Salt, Form 2

2-[4-chloro-2-(3-chloro-5-cyanobenzoyl)phenoxy]-N-{2-methyl-4-[(propionylamino)sulfonyl]phenyl}acetamide was suspended in THF containing Ca(OMe)$_2$ (1 eq) and warmed to 55° C. The mixture was stirred overnight at 50° C., and was allowed to cool to rt, and was diluted with isoproopyl alcohol. The solvent was evaporated under reduced pressure and further diluted again with isopropyl alcohol to effect a solvent swap. The mixture was evaporated to dryness and re-suspended in isopropyl alcohol. It was stirred at room temperature for about 48 h, after which time it was filtered and dried in a vacuum oven overnight at 50° C.

Example 49

2-[4-chloro-2-(3-chloro-5-cyanobenzoyl)phenoxy]-N-{2-methyl-4-[(propionylamino)sulfonyl]phenyl}acetamide, Magnesium Salt 2-[4-chloro-2-(3-chloro-5-cyanobenzoyl)phenoxy]-N-{2-methyl-4-[(propionylamino)sulfonyl]phenyl}acetamide (200 mg) was suspended in THF (5 mL) and Mg(OMe)$_2$ added as a solution in MeOH (8.7 wt %). The suspension was warmed to 35° C. The solvent was removed under reduced pressure to afford an oil that was re-suspended in CH$_3$CN (2 mL) and warmed to dissolve. Upon cooling to approximately 43° C., crystallization ensued. Water was added in 50 µL increments (150 µL total) to increase the yield. The suspension was re-heated to 35° C. and then allowed to cool slowly to rt. The solvent volume was reduced by half under reduced pressure. The sample was allowed to stand at rt, without stirring, for about 30 min, after which time it was filtered and dried in a vacuum oven overnight (50° C., ca. 9.9 mm Hg).

Example 50

2-[4-chloro-2-(3-chloro-5-cyanobenzoyl)phenoxy]-N-{2-methyl-4-[(propionylamino)sulfonyl]phenyl}acetamide, Ethanolamine Salt 2-[4-chloro-2-(3-chloro-5-cyanobenzoyl)phenoxy]-N-{2-methyl-4-[(propionylamino)sulfonyl]phenyl}acetamide (500 mg) was suspended in 5.0–10 mL of THF at rt. To this suspension was added 1.0 eq. (53 µL) of ethanolamine at rt. After several minutes, crystallization occurred. The solid was filtered under a N$_2$ blanket and dried in a vacuum oven overnight at 65° C. (house vacuum). $^1$H NMR (DMSO-d$_6$, 300 MHz) δ 8.33 (s, 1H), 8.31 (s, 1H), 8.16 (s, 1H), 8.09 (s, 1H), 7.78 (dd, J=9.0, 3.0 Hz, 1H), 7.70–7.49 (m, 5H), 7.40 (d, J=−6.0 Hz, 1H), 7.24 (d, J=9.0 Hz, 1H), 5.10 (br s, 1H), 4.79 (s, 2H), 3.56 (m, 2H), 2.84 (t, J=6.0 Hz, 2H), 2.12 (s, 3H), 1.91 (q, J=6.0 Hz, 2H), 0.84 (t, J=6.0 Hz, 3H).

Example 51

2-[4-chloro-2-(3-chloro-5-cyanobenzoyl)phenoxy]-N-{2-methyl-4-[(propionylamino)sulfonyl]phenyl}acetamide, Triethylamine salt 2-[4-chloro-2-(3-chloro-5-cyanobenzoyl)phenoxy]-N-{2-methyl-4-[(propionylamino)sulfonyl]phenyl}acetamide (100 mg) was dissolved in warm THF (2.5 ml, 40° C.). To this solution was added Et$_3$N (25 µL). Crystallization ensued within 20 min to produce a white powder. The product was collected on Whatman No. 2 filter paper and dried in a vacuum oven with N$_2$ bleed (50° C., house vacuum). $^1$H NMR (DMSO-d$_6$, 300 MHz) δ 9.37 (s, 1H), 8.31 (m, 1H), 8.16 (m, 1H), 8.09 (m, 1H), 7.68 (dd, J=9.0, 3.0 Hz, 1H), 7.60–7.49 (m, 4H), 7.24 (d, J=9.0 Hz, 1H), 4.81 (s, 2H), 2.88 (q, J=6 Hz, 6H), 2.15 (s, 3H), 2.0 (q, J=6.0 Hz, 2H), 1.09 (t, J=6 Hz, 9H), 0.85 (t, J=6.0 Hz, 3H).

Example 52
Inhibition of Viral Replication
I. HeLa Cell Assay

The HeLa cell assay was performed according to a modifcation of Kimpton J. and Emerman M., Detection of replication-competent and pseudotyped human inmmunodeficiency virus with a sensitive cell line on the basis of activation of an integrated β-galactosidase gene, *J. Virol.* 66:2232–2239 (1992), in which HIV-1 infection is detected by the activation of an HIV-LTR driven β-galactosidase reporter that is integrated into the genome of a CD4$^+$ HeLa cell line. Quantitation of β-galactosidase is achieved by measuring the activation of a chemiluminescent substrate (Tropix). The concentration of each compound required to inhibit 50% (IC$_{50}$) of the HIV-1 induced β-galactosidase signal, relative to untreated controls, was determined for each isogenic, recombinant virus.

A. Materials
HeLa-CD4-LTR-β-gal cell line (AIDS Research and Reference Reagent Program,
Division of AIDS, NIAD)
DMEM (GibcoBRL # 12430-047)
Trypsin-EDTA (GibcoBRL #25300-054)
Heat inactivated Fetal Bovine Serum (FBS) (Hyclone # SH30070.03)
Geneticin (GibcoBRL # 10131-035)
Hygromycin B (GibcoBRL # 1687-010)
96-well, black, clear-bottom, tissue culture-treated plates (Costar # 3904)
Phosphate Buffered Saline (PBS) (GibcoBRL #14190-144)
Dimethyl Sulfoxide (DMSO) (ATCC # 741625)
Galacto-Star Mammalian Reporter Gene Assay System (Tropix # 8085)

B. Growth and Maintenance of the CD4-HIV LTR-β-gal HeLa Cell Line.

HeLa-CD4-LTR-β-gal cells are propagated in DMEM containing 10% fetal bovine serum+0.2 mg/ml geneticin+0.1 mg/ml hygromycin B. Cells are split by standard trypsinization when confluency reaches 80% (roughly every 2 to 3 days).

C. Construction of HIV-1 Reverse Transcriptase (RT) Mutants

DNA encoding the HIV-1 reverse transcriptase was subcloned from a M13 phage into a general shuttle vector, pBCSK+, as a ~1.65 kbp EcoRI/HindIII ended DNA fragment. The HIV DNA insert of the resulting plasmid, pRT2, was completely sequenced on both strands prior to use in site directed mutagenesis experiments. Specific amino acid replacements were made using Stratagene Quick Change reagents and mutagenic oligonucleotides from Oligos. Following mutagenesis, the entire mutant RT coding sequence was verified by sequencing both DNA strands.

D. Construction of Isogenic HIV-1 RT Mutant Virus

Mutant HIV-1 strains were isolated by a modified Recombinant Virus Assay (Kellamn P. and Larder B., Recombinant virus assay: a rapid, phenotypic assay for assessment of drug susceptibility of human immunodeficiency virus type 1 isolates, *Antimicrobial Agents and Chemotherapy*, 38:23–30,1994). 1×10$^7$ MT4 T-cells (maintained in RPMI containing 10% fetal bovine serum, split 1:5 every 5 to 6 days) were co-transfected with EcoRI/HindIII digested mutant RT plasmid and Bst EII-digested HIV-1$_{HXB2\Delta RT}$ DNA in the presence of DMRIE-C transfection reagent (Gibco) according to supplier's recommended protocol. Each mutant RT coding sequence was crossed into the RT-deleted HIV-1 viral DNA backbone by in vivo homologous recombination. Transfected cell cultures were expanded and monitored until syncitia formation and CPE were extensive. Virus was harvested by clear spin of the culture supernatants and frozen at −80° C. as primary stock. Recombinant progeny virus was sequenced in the RT region to confirm the mutant genotype. Virus stocks were further expanded by infection of MT4 cells, harvested and stored as frozen aliquots. Stocks were titered in HeLa MAGI cells for assay.

E. Titering of Virus Stocks

HIV-1 virus stocks must be titered in the MAGI assay system to establish the appropriate infecting dose. The endpoint for this assay is relative light units (RLUs), and titer is recorded as RLUs/ml. Virus stocks are diluted (serial 1:2) into DMEM containing 10% FBS plus 25 ug/ml DEAE-dextran and assayed as described in the "procedure" section below without test compound.

A "multiplicity of infection" (MOI) defined as infectious units per cell is usually not calculated but is typically <<1.0. Relationship of RLUs/ml to other measures of infectivity such as HeLa PFU/ml or MT4 TCID50/ml may not be consistent from lot to lot or strain to strain and should be determined for each lot.

F. Experimental Protocol

Day 1

1. Seed 96-well plate(s) (Costar #3904) with HeLa-CD4-LTR-β-gal @ 3×103 cells per well in 100 ul DMEM containing 10% FBS. Incubate @ 37° C., 5% $CO_2$ overnight.

Day 2

1. Thaw virus stock in a water bath (room temperature) and dilute into DMEM+10% FBS+25 ug/ml DEAE-dextran to an infectious dose of 1500 to 2000 RLU/ml. The dilution of virus will vary depending on the titer of the stock (see advanced preparation section above).
2. Remove all of the media from every well with an 8 or 12-channel manifold aspirator. Work with one plate at a time to prevent drying of the HeLa-CD4-LTR-β-gal monolayer. Add 35 ul (75 to 100 total RLUs) of diluted virus to each well. Incubate @ 37° C., 5% $CO_2$ for 2 hours.
3. During the virus adsorption period prepare compound titration plates at 1.35× final concentration. In general, test compounds are titrated robotically in a five-fold stepwise manner from 2.7 uM (2 uM final) down to 1.35 nM (1 nM final). This scheme will allow for 8 test compounds per 96-well plate with 10 dilution points and 2 controls per compound (n=1). Test compounds are titrated into DMEM+10% FBS+0.135% DMSO (0.1% final). The final volume of titrated compound in each well should be at least 150 ul and DMSO should be at 0.135% (0.1% final) including the no compound controls.
4. Remove 100 ul of titrated compound from every well of the titration plate prepared in step 3 above and add to the virus adsorption plate (step 2 above).
5. Incubate @ 37° C., 5% $CO_2$ for 72 hours.

Day 5

1. Remove supernatants from every well with an 8 or 12-channel manifold aspirator. Work with one plate at a time to prevent drying of infected HeLa-CD4-LTR-β-gal monolayer.
2. Wash each well with 100 ul PBS
3. Aspirate PBS as in step 1 above.
4. Add 15 ul lysis buffer provided by Tropix kit. Gently tap plate to disperse lysis buffer across bottom of well.
5. Incubate @ room temperature for at least 10 mins.
6. Dilute Tropix substrate (kit reagent) 1:50 into room temperature substrate dilution buffer (kit reagent) and add 100 ul to each well.
7. Read each plate in a luminometer (Topcount, Packard works best). The signal is linear and constant for up to 2 hr after the addition of substrate. Plates can be read at any time during this 2 hr period.

G. Data Analysis

Raw data are transformed into % of control by the following formula: (raw signal in each well/average raw signal for the two no compound controls in the same row)*100. Percent of control is plotted vs. compound concentration using Either Robsage or Robofit programs (GW). The default model is $Y=Vmax*1-x^n/(K^n+x^n)$, however, any other model giving a reasonable estimation of the $IC_{50}$ ("K" in formula) may be used.

II. MT4 Cell Assay

A. Experimental Procedure

Antiviral HIV activity and compound-induced cytotoxicity were measured in parallel by means of a propidium iodide based procedure in the human T-cell lymphotropic virus transformed cell line MT4. Aliquots of the test compounds were serially diluted in medium (RPMI 1640, 10% fetal calf serum (FCS), and gentamycin) in 96-well plates (Costar 3598) using a Cetus Pro/Pette. Exponentially growing MT4 cells were harvested and centrifuged at 1000 rpm for 10 min in a Jouan centrifuge (model CR 4 12). Cell pellets were resuspended in fresh medium (RPMI 1640, 20% FCS, 20% IL-2, and gentamycin) to a density of 5×105 cells/ml. Cell aliquots were infected by the addition of HIV-1 (strain IIIIB) diluted to give a viral multiplicity of infection of 100×TCID50. A similar cell aliquot was diluted with medium to provide a mock-infected control. Cell infection was allowed to proceed for 1 hr at 37° C. in a tissue culture incubator with humidified 5% $CO_2$ atmosphere. After the 1 hr incubation the virus/cell suspensions were diluted 6-fold with fresh medium, and 125 μl of the cell suspension was added to each well of the plate containing pre-diluted compound. Plates were then placed in a tissue culture incubator with humidified 5% $CO_2$ for 5 days. At the end of the incubation period, cell number and hence HIV-induced cytopathy was estimated by either (A) propidium iodide staining, or by an (B) MTS tetrazolium staining method (ref 5).

A. For propidium iodide readout, 27 μl of 5% Nonidet-40 was added to each well of the incubation plate. After thorough mixing with a Costar multitip pipetter, 60 μl of the mixture was transferred to filter-bottomed 96-well plates. The plates were analyzed in an automated assay instrument (Screen Machine, Idexx Laboratories). The control and standard used was 3'-azido-3'-deoxythymidine tested over a concentration range of 0.01 to 1 μM in every assay. The expected range of $IC_{50}$ values for 3'-azido-3'-deoxythymidine is 0.04 to 0.12 μM. The assay makes use of a propidium iodide dye to estimate the DNA content of each well.

B. For MTS readout, 20 μl CellTiter 96 AQ One Solution reagent (Promega #G3582) was added to each well. At 75 minutes following the addition of MTS reagent, absobance was read at 492 nM using a Tecan Sunrise 96-well plate reader.

B. Analysis

The antiviral effect of a test compound is reported as an $IC_{50}$, i.e. the inhibitory concentration that would produce a 50% decrease in the HIV-induced cytopathic effect. This effect is measured by the amount of test compound required to restore 50% of the cell growth of HIV-infected MT4 cells, compared to uninfected MT4 cell controls. $IC_{50}$ was calculated by RoboSage, Automated Curve Fitting Program, version 5.00, 10 Jul. 1995.

For each assay plate, the results (relative fluorescence units, rfU, or OD values) of wells containing uninfected cells or infected cells with no compound were averaged, respectively. For measurements of compound-induced cytotoxicty, results from wells containing various compound concentrations and uninfected cells were compared to the average of uninfected cells without compound treatment. Percent of cells remaining is determined by the following formula:

Percent of cells remaining=(compound-treated uninfected cells, rfU, or OD values/untreated uninfected cells)×100.

A level of percent of cells remaining of 79% or less indicates a significant level of direct compound-induced cytotoxicity for the compound at that concentration. When this condition occurs the results from the compound-treated infected wells at this concentration are not included in the calculation of $IC_{50}$.

For measurements of compound antiviral activity, results from wells containing various compound concentrations and infected cells are compared to the average of uninfected and infected cells without compound treatment. Percent inhibition of virus is determined by the following formula:

Percent inhibition of virus=(1−((ave. untreated uninfected cells−treated infected cells)/(ave. untreated uninfected cells−ave. untreated infected cells)))×100

REFERENCES

1. Averett, D. R., Anti-HIV compound assessment by two novel high capacity assays, *J. Virol. Methods* 23: 263–276, 1989.
2. Schwartz, O., et al., A rapid and simple colorimetric test for the study of anti-HIV agents, *AIDS Res. and Human Retroviruses* 4 (6): 441–447, 1988.
3. Daluge, S. M., et al., 5-chloro-2'3'-deoxy-3'fluorouridine (935U83), a selective anti-human immunodeficiency virus agent with an improved metabolic and toxicological profile. *Antimicro. Agents and Chemother.* 38 (7): 1590–1603, 1994.
4. Dornsife, R. E., et al., Anti-human immnunodeficiency virus synergism by zidovudine (3'-azidothymidine) and didanosine (dideoxyinosine) contrasts with the additive inhibition of normal human marrow progenitor cells, *Antimicro. Agents and Chemother.* 35 (2): 322–328, 1991.
6. Promega Technical Bulletin #TB245. CellTiter 96 AQ One Solution Cell Proliferation Assay.

Antiviral Activity of Parent Compounds

Compounds of the present invention, have anti-HIV activity and deliver compounds that have anti-HIV activity in the range $IC_{50}$=1–1000 nM against wild type and mutant viruses. Table 1 shows a comparison between the anti-HIV activity of compounds delivered by the compounds of the present invention and compounds 1e–1g of Wyatt et al. *J. Med. Chem.* 1995, vol. 38, p. 1657–1665. WT indicates wild type virus; Nev-R indicates mutant virus.

TABLE 1

Cpds A, 58, 40, 71

Cpds 1e–1g

| Cpd No. | Structure | Wt (nM) | Nev-R (nM) |
|---|---|---|---|
| A | 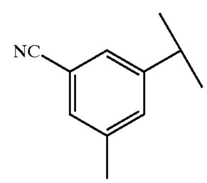 | 0.5–0.6 | 0.5–0.8 |
| 58 | 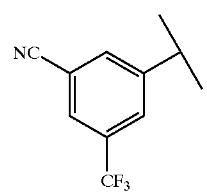 | 2.4 | 0.9 |
| 40 | 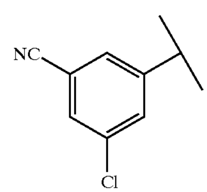 | 0.5–1.8 | 0.4–1.2 |
| 71 | 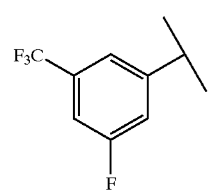 | 0.1–28 | 0.4–14 |
| 1e | R = OCH2CH2N(Et)2 | 88–280 | 970–1670 |
| 1f | R = OCH2CH2CH2N(Et)2 | 31–47 | 260–370 |
| 1g | R = H | 22 | 276–320 |

EXAMPLE 53

Pharmacokinetic Studies in Male Beagle Dogs

Compound 34 (634A in tables and on plots) was dosed as a solid as well as in solution form to male beagle dogs according to the following protocol. Plasma samples were analyzed using the following methods:

Blood samples from the test animals were drawn at periodic intervals, before, and after administration of the test articles. The samples were dispensed into chilled (~+4° C.) blood tubes containing EDTA anticoagulant which were stored "on ice" (~+4° C.) prior to centrifugation and separation of the plasma fractions. The plasma samples were transferred to frozen storage (−20° C.) within 30 minutes of blood sampling.

0.4 mL/minute. An Aqua $C_{18}$ HPLC column (3 micron particle size, 20 mm×2 mm[id], Phenomenex Inc.) was used to separate the sample extracts prior to detection by MS-MS.

Gradient Conditions

Mobile phase "A"; 0.1% acetic acid (aq.) pH adjusted to 4.6 with ammonium hydroxide: acetonitrile (95:5 v/v)

Mobile phase "B"; acetonitrile: acetic acid (99.9:0.1 v/v)

| Dosing Session | Gr. No. | No. of Males | Test Article | Dose mg/kg | Conc. (mg/mL) | Dose Vol. (mL/kg) | Vehicle | Route | Flush Vol. |
|---|---|---|---|---|---|---|---|---|---|
| | | | | | | Treatment | | | |
| 3 | 3 | 3 | Cmpd. 34 | 10 | 5 | 2.0 | PEG400:Solutol:Water (30:20:50 Vehicle v/v/v) | PO | 10 mL |
| 3 | 5 | 2 | Cmpd. 34 (solid dose) | 1 | 10 mg/31 mg | 31 mg HPMC Capsule/ 10 kg Dog | Test Article: Crospovidone: Lactose Anhydrate (10:1:20 w/w/w). | PO | 10 mL Water |
| 3 | 6 | 1 | Cmpd. 34 | 1 | 5 | 0.2 | PEG400:Solutol:Water (30:20:50 v/v/v) | IV | 2 mL Vehicle |

Test Article Storage: As Received
Dosage Form, samples: 0.1 g pre-dose
Overnight Fast: Yes
Comments: Protect from light
Storage Of Plasma: −70° C.
Food Return: 4 hours post-dosing

| Dosing Session | Sample Collection Times | | |
|---|---|---|---|
| | Hematology | Clin. Chem. | Blood/Plasma |
| 3 | Prior To Treatment For Study Health Assessment | Pre-Dose, 5, 15, 30 min. and 1, 2, 4, 8, 10, 12, and 24 hrs post-dose | |
| Anticoagulant | EDTA | None | EDTA |
| Volume/ Timepoint | 0.5 mL | 1.8 mL | 5 mL |

Sample Preparation

The plasma samples were thawed at room temperature, vortex-mixed for 10 seconds, and 100 μL aliquots transferred to 96-well micro-plates. Aliquots (100 μL) of spiked plasma calibration standards (typical concentration range= 1–250 μg/L) together with quality control (QC) samples were dispensed into the micro-plates alongside the samples. Acetonitrile (400 μL) was added to each sample, standard and QC sample to precipitate plasma proteins. The micro-plates were placed on a plate shaker for two minutes to mix the contents of the wells and then centrifuged (3000×g for 10 minutes).

The supernatant fractions of the wells were transferred to a fresh micro-plate and then evaporated to dryness at 37° C. under a stream of ($O_2$-free) nitrogen. The well residues were reconstituted in 100 μL volumes of acetonitrile:water:acetic acid (40:59.9:0.1 v/v/v) and 20 μL volumes were analyzed by HPLC-MS-MS.

HPLC-MS-MS Conditions

HPLC Conditions

A model BP1100 binary (high pressure mixing) solvent delivery system (Agilant Technologies) was used to generate the mobile phase gradient described below at a flow rate of Gradient Profile;

| Time | % B | Event |
|---|---|---|
| 0 | 20 | Inject Sample |
| 1 | 95 | Sample Separation |
| 2 | 95 | " |
| 2.5 | 20 | Re-equilibration |
| 4 | 20 | Stop Time |

MS-MS Conditions

Autosampler; HTS-PAL (Leap Technologies)
MS-MS System; Sciex API 365 or API 3000 (Sciex Inc.)
Source: Turbo IonSpray
Ionization: Negative
Dwell Time: 150 msec/analyte
Compound Specific Conditions;

| Compound | MWT | Q1 m/z | Q3 m/z | Orifice | Ring | Collision Energy |
|---|---|---|---|---|---|---|
| 34 | 596.4 | 572.1 | 289.7 | 30 | 160 | 40 eV |

Data Reduction

The measurement of signal peaks areas, calibration and quantification were carried out using the Turbo-Quan V1.5 (Sciex Inc.) data acquisition and processing software (DAQ) suite. The DAQ software generated sample concentration results tables in Excel 97 (Microsoft Inc.) spreadsheet format. These data were processed using the proprietary Excel VBA macro "PK Solutions 2" (Summit Research Services) to calculate the values of the cited pharmacokinetic parameters using a "non-compartmental" approach based on area under the concentration-time curve (AUC) measurements using the classical trapezoidal rule.

TABLE 2

Summary of the pharmacokinetic data for compound 34 in male beagle dogs

| Cmpd. Dosed | Dose (mg/kg) | Route | Mean Cmpd. 40 $C_{max}$ (μg/L) | Mean Cmpd. 40 $T_{max}$ (μg/L) | Mean Cmpd. 40 Elim. $t_{1/2}$ (hours) | Mean Cmpd. 40 $AUC_{0-inf(area)}$ (mg-hr/L) | Mean Cmpd. 40 $Cl_{(area)}$ (L/hr/kg) | Mean Cmpd. 40 $V_{d(area)}$ (L/kg) | Mean % f |
|---|---|---|---|---|---|---|---|---|---|
| 34 | 1.057 | PO (solution) | 148 | 3.3 | 11.7 | 2.74 | 0.41 | 6.5 | 90 |
| 34 | 10.57 | PO (solution) | 1920 | 4.0 | 8.5 | 32.3 | 0.35 | 4.1 | 106 |
| 34 | 0.874 | PO (solid) | 91.3 | 4.0 | 9.9 | 1.61 | 0.57 | 7.8 | 64 |

The results demonstrate that the oral administration of compound 34 resulted in excellent bioavailability. Results also show that the active inhibitor, compound 40, appears in the plasma following administration of compound 34.

Example 54
Oral Bioavailability in Male Sprague-Dawley Rats
Methods

Compound Specific Conditions:

| Cpd | MWT | Q1 m/z | Q3 m/z | Orifice | Ring | Collision Energy |
|---|---|---|---|---|---|---|
| 41 | 574.4 | 572.1 | 289.7 | 30 | 160 | 40 eV |
| 40 | 518.4 | 516.1 | 289.7 | 30 | 160 | 40 eV |

TABLE 3

Oral Bioavailability in Male Sprague-Dawley (CD) Rats

| Test Substance | | | Administration | | | Mean Exposures of 40[a] | |
|---|---|---|---|---|---|---|---|
| Cpd | Salt Form | Crystal Form | Route | Dose (mg/kg) | Vehicle/Excipient | $AUC_{0-\infty}$ (hr · ng/mL) | $F_{app}$ (%) |
| 40 | Free acid | Amorph. | IV | 1 | PEG400:Solutol:Water (30:20:50) | 1744 ± 363 | N/A |
| | | | PO (soln) | 1 | DMSO:Tween-80:5% Mannitol (20:0.1:79.9) | 128 (n = 1) | 7 |
| | | Form 1 | PO (susp) | 1 | 0.5% HPMC, 0.1% Tween-80 | NC | NC |
| 41[b] | Free acid 41 | Amorph | PO (soln) | 0.87 | PEG400:Solutol:Water (30:20:50) | 951 ± 123 | 63 |
| | | Amorph | PO (susp) | 0.87 | 0.5% HPMC, 0.1% Tween-80 | 126 ± 69 | 8 |
| | Na 34 | Amorph. | PO (soln) | 0.87 | PBS | 766 ± 396 | 50 |
| | | Form 1 | PO (solid) | 0.79 | Lactose anhydrate (2:1) | 549 ± 187 | 40 |

[a] $AUC_{0-\infty}$, area under the plasma concentration-time curve extrapolated to infinity; $F_{app}$, approximate oral bioavailability, based on ratio of dose-normalized mean $AUC_{0-\infty}$ values for 40 following PO administration of 40 or 41 and salts thereof and IV administration of 40, expressed as a percentage; NC, not calculable (plasma levels below detection limit).
[b] Doses of 41 and salts thereof expressed as molar equivalent doses of 40.
[c] ND, not determined.

Methods used were generally as described in Example 53, with the following modifications: Sample Collection—In addition to anticoagulant (EDTA), an enzyme inhibitor cocktail containing 50 μL of 100 mM AEBSF (4-(2-aminoethyl)benzenessulfonylfluoride HCl, CalBioChem, cat. no. 101500); 200 mM Benzamide(CalBioChem, cat. no. 199001); and 200 mM EACA (Epislon Amino-n-caproic acid, CalBioChem cat. no. 1381) in FTA Hemaglutionation Buffer (Becton Dickson, cat. no. 4311248) per 1 mL of blood was added to rat blood samples at the time of collection.

HPLC-MS-MS Conditions—Chromatography was performed on a Phenomenex Aqua $C_{18}$ HPLC Mercury Cartridge (3-micron particle size, 20 mm×2 mm id) or Luna $C_{18}$ column (50×2 mm).

The results demonstrate that oral administration of compound 34 resulted in improved bioavailability in comparison to the parent compound 40. Results also show that the active inhibitor, compound 40, appears in the plasma following administration of compound 34 or 41.

Example 55
Solubility
Method

An excess amount of the compound was added to a 5 ml vial containing 1 ml of 0.1N HCl, water, or pH 9 bicarbonate buffer. A stir bar was put in the vial. The vials were closed with caps and placed on stir plate. The samples were stirred at room temperature. After equilibration, the samples were centrifuged. An accurate aliquot of clear solution was transferred to a HPLC vial by micropipette. The solubility was determined by HPLC with UV detector and against standard.

TABLE 4

Solubility of compounds 40, 41 and salts of compound 41

| Salt Form | Crystal Form | Solvent | Solubility (mg/ml) |
|---|---|---|---|
| compound 40 | Form 1 | 0.1 N HCl | ND |
| | | Phosphate buffer (pH 7.4) | ND |
| | | SIF | 0.0029 |
| compound 41 | Form 1 | 0.1 N HCl | ND |
| sodium salt | Form 1 | water | 92 |
| | Form 4 | water | 2.5 |
| | Form 9 | water | >100 |
| | Form 10 | water | >100 |
| | Form 12 | water | >100 |
| | Amorphous | water | >100 |
| Calcium salt | Form 2 | water | 0.7 |
| Ethanolamine | Form 1 | water | 2.5 |
| Choline | Form 1 | water | 66 |

ND = not detectable
Note: All the salts will convert to free acid in 0.1 N HCl

The results demonstrate that compound 41 and salts thereof have improved solubility in comparison with compound 40.

Example 56
Crystal Structure of 2-[4-chloro-2-(3-chloro-5-cyanobenzoyl)phenoxy]-N-{2-methyl-4-[(propionylamino)sulfonyl]phenyl}acetamide, Choline Salt Form 1

The crystal and molecular structures of Form 1 of the choline salt of 2-[4-chloro-2-(3-chloro-5-cyanobenzoyl)phenoxy]-N-{2-methyl-[(propionylamino)sulfonyl]phenyl}acetamide were determined from three-dimensional X-ray diffraction data collected at 150(2)K using a crystal produced by recrystallization from acetonitrile using slow cooling techniques. Final lattice parameters were determined from a refinement of the reflections measured on a Nonius KappaCCD diffractometer. 49834 data on the diffractometer over the range $5.92° \leq 2\theta \leq 50.69°$ using graphite monochromated molybdenum radiation ($\lambda K\alpha=0.71073$ Å). The structure was solved by direct methods and refined using a full-matrix least-squares procedure which converged ($\Delta/\sigma_{max}=0.09$) to values of the conventional crystallographic residuals R1=0.050 for observed data, and R1=0.067 (wR2=0.132) for all data. Powder patterns calculated using the single crystal results show good agreement in peak positions with the measured x-ray powder diffraction results (Table 5).

TABLE 5

Sampling of d-spacing, 2-theta and relative intensity calculated from the single crystal XRD structural parameters.

| d-spacing+ | 2-theta | relative intensity* |
|---|---|---|
| 16.9 | 5.2 | 3 |
| 12.8 | 6.9 | 6 |
| 10.1 | 8.8 | 57 |
| 8.5 | 10.5 | 17 |
| 7.3 | 12.1 | 40 |
| 6.7 | 13.2 | 29 |
| 6.2 | 14.2 | 12 |
| 5.9 | 15.0 | 14 |
| 5.6 | 15.7 | 68 |
| 5.3 | 16.8 | 23 |
| 5.2 | 17.0 | 43 |
| 4.4 | 20.0 | 30 |
| 4.4 | 20.4 | 22 |
| 4.3 | 20.6 | 26 |
| 4.3 | 20.8 | 51 |
| 4.3 | 20.9 | 4 |
| 4.2 | 21.0 | 27 |
| 4.2 | 21.3 | 44 |
| 4.2 | 21.4 | 40 |
| 4.1 | 21.7 | 30 |
| 4.1 | 22.0 | 23 |
| 4.0 | 22.1 | 69 |
| 4.0 | 22.3 | 100 |
| 4.0 | 22.4 | 13 |
| 3.9 | 23.1 | 45 |
| 3.8 | 23.2 | 15 |
| 3.8 | 23.3 | 24 |
| 3.8 | 23.7 | 34 |
| 3.7 | 23.8 | 13 |
| 3.7 | 24.2 | 21 |
| 3.7 | 24.3 | 56 |
| 3.6 | 25.0 | 80 |
| 3.5 | 25.1 | 70 |

*As is well known in XRPD studies, preferred orientation can significantly distort relative intensities
+The room temperature unit cell is a = 20.911 Å, b = 7.854 Å, c = 21.462 Å, β = 105.96°, V = 3389.3 Å$^3$ and the wavelength, ($\lambda$Cu, K$\alpha$ = 1.54 Å)

What is claimed is:
1. A compound of formula (IA)

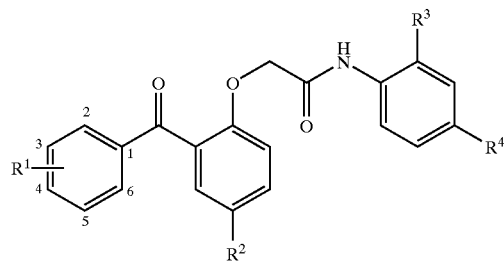

(IA)

wherein:
R$^1$ is one or more substituents independently selected from the group consisting of halogen, —CF$_3$, C$_{1-8}$alkyl, aminoC$_{1-8}$alkyl, alkoxy, —CN, —NO$_2$, —NH$_2$, —SR$^8$, —S(O)R$^8$, —S(O)$_2$R$^8$, —C(O)R$^8$; C$_{2-6}$alkenyl which may be optionally substituted with a substituent selected from the group consisting of hydroxy, halogen, C$_{3-6}$cycloalkyl, C$_{6-14}$aryl and heterocycle; C$_{2-6}$alkynyl which may be optionally substituted with a substituent selected from the group consisting of hydroxy, halogen, C$_{6-14}$aryl, C$_{3-6}$cycloalkyl, and heterocycle; and heterocycle, optionally substituted with one or more substituents selected from the group consisting of halogen, C$_{1-8}$alkyl, —CN, C$_{1-8}$alkylC$_{6-14}$aryl and heterocycle;
R$^2$ is selected from the group consisting of hydrogen, halogen, C$_{1-8}$alkyl, —NO$_2$, —NH$_2$, C$_{1-8}$alkylamino, —CF$_3$ and alkoxy;
R$^3$ is selected from the group consisting of hydroxy, halogen, —CF$_3$, —NO$_2$ and C$_{1-8}$alkyl;
R$^4$ is selected from the group consisting of —S(O)$_2$NR$^5$R$^6$, —S(O)$_2$N=C(OR$^7$)$_2$ and —S(O)$_2$N=CR$^7$(OR$^7$);

$R^5$ is selected from the group consisting of hydrogen, $C_{6-14}$aryl, $C_{1-8}$alkyl, $C_{3-6}$cycloalkyl$C_{1-8}$alkyl and $C_{3-6}$cycloalkyl;

$R^6$ is selected from the group consisting of —C(O)$R^7$, —C(O)O$R^7$, —C(O)C(O)O$R^7$, —C(O)CH(N$R^{12}R^{13}$) $R^{11}$, alkoxy$C_{1-8}$alkyl and —CH$_2$O—(CH$_2$CH$_2$O)$_n$—CH$_2$CH$_2$OCH$_3$, wherein n is 0–4;

$R^7$ is selected from the group consisting of $C_{3-6}$cycloalkyl$C_{1-8}$alkyl, hydroxy$C_{1-8}$alkyl, $C_{6-14}$aryl, heterocycle optionally substituted with $C_{1-8}$alkyl, $C_{6-14}$aryl$C_{1-8}$alkyl, —(CH$_2$CH$_2$—O)$_n$—CH$_3$, where n=1–4, alkoxy$C_{1-8}$alkyl and $C_{1-8}$alkyl optionally substituted with —O—C(O)$R^{12}$;

$R^8$ is selected from the group consisting of $C_{1-8}$alkyl, $C_{3-6}$cycloalkyl$C_{1-8}$alkyl, $C_{3-6}$cycloalkyl, $C_{6-14}$aryl and heterocycle;

$R^{11}$ is selected from the group consisting of hydrogen,

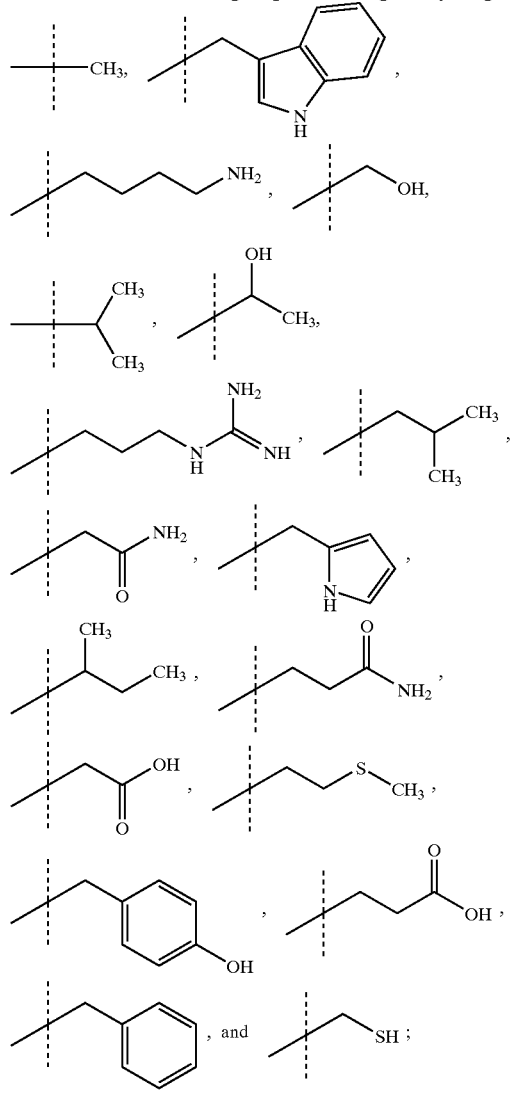

$R^{12}$ and $R^{13}$ are independently selected from the group consisting of hydrogen, $C_{1-8}$alkyl, $C_{3-6}$cycloalkyl and $C_{6-14}$aryl;

or a pharmaceutically acceptable derivative thereof.

2. A compound of formula (IA) according to claim 1 wherein:

$R^1$ is a substituent in either the 3 or 5 position, or both the 3 and 5 positions, independently selected from the group consisting of halogen, —CF$_3$, $C_{1-8}$alkyl, amino$C_{1-8}$alkyl, alkoxy, —CN, —NO$_2$, —NH$_2$, —S$R^8$, —S(O)$R^8$, —S(O)$_2R^8$, —C(O)$R^8$; $C_{2-6}$alkenyl which may be optionally substituted with a substituent selected from the group consisting of hydroxy, halogen, $C_{3-6}$cycloalkyl, $C_{6-14}$aryl and heterocycle; $C_{2-6}$alkynyl which may be optionally substituted with a substituent selected from the group consisting of hydroxy, halogen, $C_{6-14}$aryl, $C_{3-6}$cycloalkyl, and heterocycle; and heterocycle, optionally substituted with one or more substituents selected from the group consisting of halogen, $C_{1-8}$alkyl, —CN, $C_{6-14}$aryl$C_{1-8}$alkyl and heterocycle;

$R^2$ is selected from the group consisting of hydrogen, halogen, $C_{1-8}$alkyl, —NO$_2$, —NH$_2$, $C_{1-8}$alkylamino, —CF$_3$ and alkoxy;

$R^3$ is selected from the group consisting of hydroxy, halogen, —CF$_3$, —NO$_2$ and $C_{1-8}$alkyl;

$R^4$ is selected from the group consisting of —S(O)$_2$N$R^5R^6$, —S(O)$_2$N=C(O$R^7$)$_2$ and —S(O)$_2$N=C$R^7$(O$R^7$);

$R^5$ is selected from the group consisting of hydrogen, $C_{6-14}$aryl, $C_{1-8}$alkyl, $C_{3-6}$cycloalkyl$C_{1-8}$alkyl and $C_{3-6}$cycloalkyl;

$R^6$ is selected from the group consisting of —C(O)$R^7$, —C(O)O$R^7$, —C(O)C(O)O$R^7$, —C(O)CH(N$R^{12}R^{13}$) $R^{11}$, alkoxy$C_{1-8}$alkyl and —CH$_2$O—(CH$_2$CH$_2$O)$_n$—CH$_2$CH$_2$OCH$_3$, wherein n is 0–4;

$R^7$ is selected from the group consisting of $C_{3-6}$cycloalkyl$C_{1-8}$alkyl, hydroxy$C_{1-8}$alkyl, $C_{6-14}$aryl, heterocycle optionally substituted with $C_{1-8}$alkyl, $C_{6-4}$aryl$C_{1-8}$alkyl, —(CH$_2$CH$_2$—O)$_n$—CH$_3$, where n=1–4, alkoxy$C_{1-8}$alkyl and $C_{1-8}$alkyl optionally substituted with —O—C(O)$R^{12}$;

$R^8$ is selected from the group consisting of $C_{1-8}$alkyl, $C_{3-6}$cycloalkyl$C_{1-8}$alkyl, $C_{3-6}$cycloalkyl, $C_{6-14}$aryl and heterocycle;

$R^{11}$ is selected from the group consisting of hydrogen,

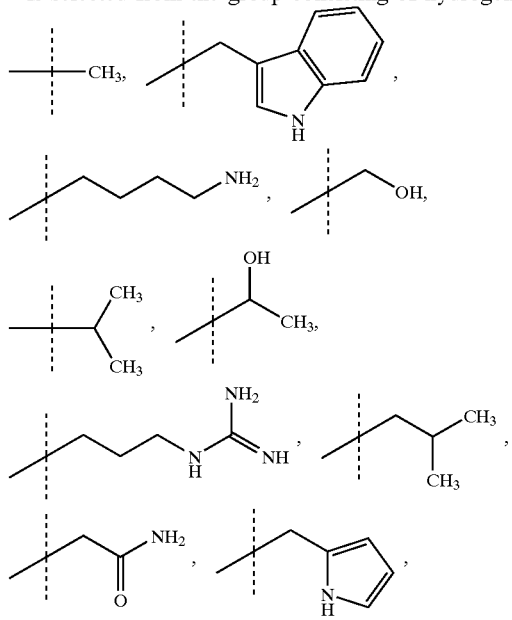

-continued

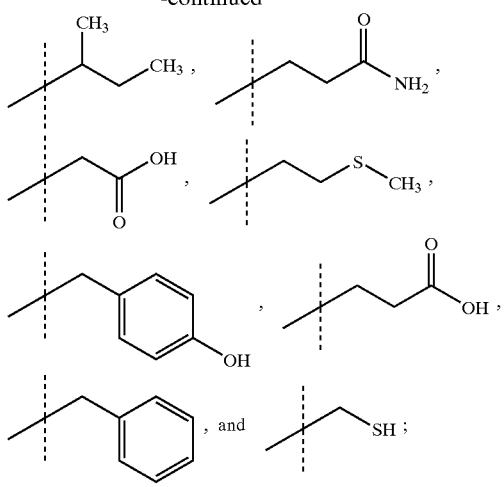

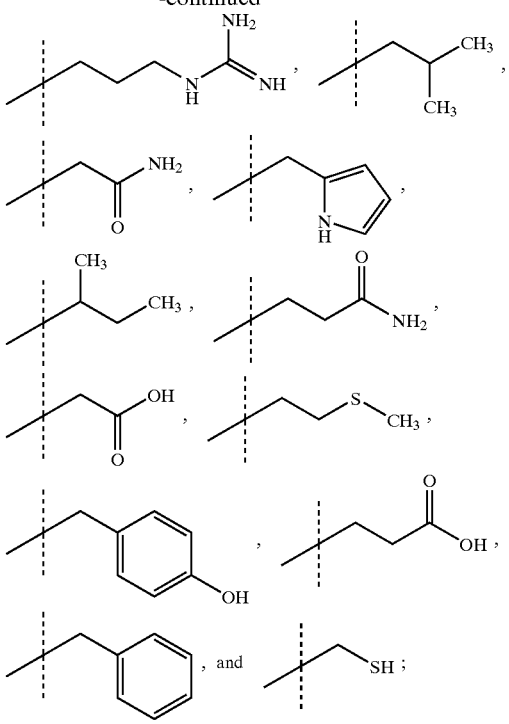

$R^{12}$ and $R^{13}$ are independently selected from the group consisting of hydrogen, $C_{1-8}$alkyl, $C_{3-6}$cycloalkyl and $C_{6-14}$aryl;

or a pharmaceutically acceptable derivative thereof.

3. A compound of formula (IA) according to claim 1 wherein:

$R^1$ is a substituent in the 3 or 5 position, or in both the 3 and 5 positions, independently selected from the group consisting of halogen, $C_{1-8}$alkyl, —$CF_3$ and —CN;

$R^2$ is selected from the group consisting of halogen, $C_{1-8}$alkyl, —$NO_2$, —$CF_3$ and alkoxy;

$R^3$ is $C_{1-8}$alkyl;

$R^4$ is selected from the group consisting of —$S(O)_2$ $NR^5R^6$, —$S(O)_2N\!=\!C(OR^7)_2$ and —$S(O)_2N\!=\!CR^7 (OR^7)$;

$R^5$ is selected from the group consisting of hydrogen, $C_{6-14}$aryl, $C_{1-8}$alkyl, $C_{3-6}$cycloalkyl$C_{1-8}$cycloalkyl and $C_{3-6}$cycloalkyl;

$R^6$ is selected from the group consisting of —C(O)$R^7$, —C(O)O$R^7$, —C(O)CH(N$R^{12}R^{13}$)$R^{11}$, —C(O)OC(O) O$R^7$, alkoxy$C_{1-8}$alkyl and —$CH_2O$—($CH_2CH_2O)_n$— $CH_2CH_2OCH_3$, wherein n is 0–4;

$R^7$ is selected from the group consisting of $C_{3-6}$cycloalkyl$C_{1-8}$alkyl, hydroxy$C_{1-8}$alkyl, $C_{6-14}$aryl, heterocycle optionally substituted with $C_{1-8}$alkyl, $C_{6-14}$aryl$C_{1-8}$alkyl, —($CH_2CH_2$—O)$_n$—$CH_3$, where n=1–4, alkoxy$C_{1-8}$alkyl and $C_{1-8}$alkyl optionally substituted with —O—C(O)$R^{12}$;

$R^{11}$ is selected from the group consisting of hydrogen

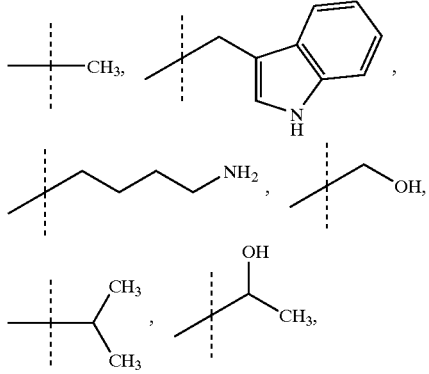

$R^{12}$ and $R^{13}$ are independently selected from the group consisting of hydrogen, $C_{1-8}$alkyl, $C_{3-6}$cycloalkyl and $C_{6-14}$aryl;

or a pharmaceutically acceptable derivative thereof.

4. A compound of formula (IA) according to claim 1 wherein:

$R^1$ is a substituent in the 3 or 5 position, or in both the 3 and 5 positions, independently selected from the group consisting of halogen, $C_{1-8}$alkyl, —$CF_3$ and —CN;

$R^2$ is halogen;

$R^3$ is $C_{1-8}$alkyl;

$R^4$ is selected from the group consisting of —$S(O)_2$ $NR^5R^6$, —$S(O)_2N\!=\!C(OR^7)_2$ and —$S(O)_2N\!=\!CR^7 (OR^7)$;

$R^5$ is selected from the group consisting of hydrogen, $C_{6-14}$aryl, $C_{1-8}$alkyl, $C_{3-6}$cycloalkyl$C_{1-8}$alkyl and $C_{3-6}$cycloalkyl;

$R^6$ is selected from the group consisting of —C(O)$R^7$, —C(O)O$R^7$, —C(O)CH(N$R^{12}R^{13}$)$R^{11}$, alkoxy$C_{1-8}$ alkyl and —$CH_2O$—($CH_2CH_2O)_n$—$CH_2CH_2OCH_3$, wherein n is 0–4;

$R^7$ is selected from the group consisting of $C_{3-6}$cycloalkyl$C_{1-8}$alkyl, hydroxy$C_{1-8}$alkyl, $C_{6-14}$aryl, heterocycle optionally substituted with $C_{1-8}$alkyl, $C_{6-14}$aryl$C_{1-8}$alkyl, —($CH_2CH_2$—O)$_n$—$CH_3$, where n=1–4, alkoxy$C_{1-8}$alkyl and $C_{1-8}$alkyl optionally substituted with —O—C(O)$R^{12}$;

$R^{11}$ is selected from the group consisting of hydrogen and

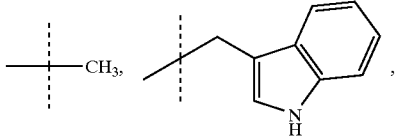

-continued

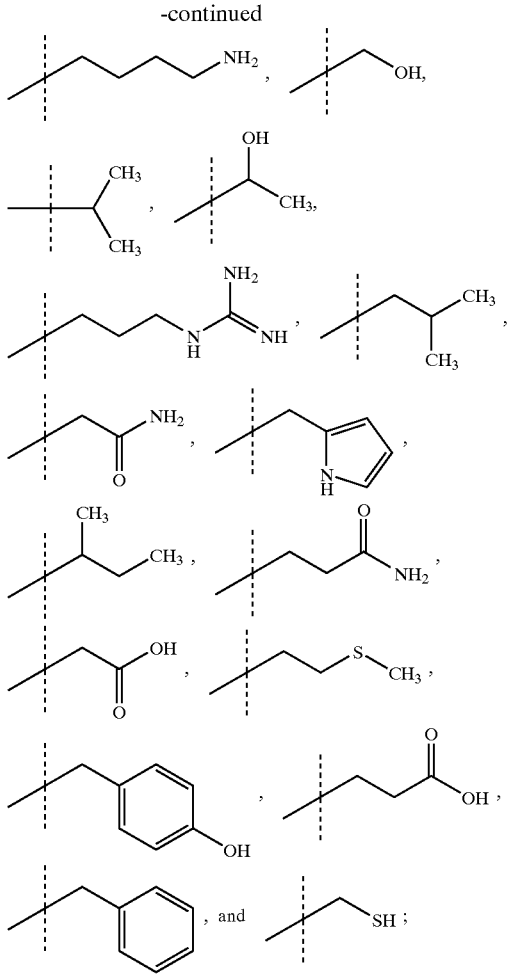

$R^{12}$ and $R^{13}$ are independently selected from the group consisting of hydrogen, $C_{1-8}$alkyl, $C_{3-6}$cycloalkyl and $C_{6-14}$aryl;

or a pharmaceutically acceptable derivative thereof.

5. A compound of formula (IA) according to claim 1 wherein:
   $R^1$ is a substituent in the 3 or 5 position, or in both the 3 and 5 positions, independently selected from the group consisting of halogen, $C_{1-8}$alkyl, —$CF_3$ and —CN;
   $R^2$ is halogen;
   $R^3$ is $C_{1-8}$alkyl;
   $R^4$ is —$S(O)_2NR^5R^6$;
   $R^5$ is selected from the group consisting of hydrogen, $C_{1-8}$alkyl, $C_{3-6}$cycloalkyl$C_{1-8}$alkyl and $C_{3-6}$cycloalkyl;
   $R^6$ is selected from the group consisting of —$C(O)R^7$ and —$C(O)OR^7$;
   $R^7$ is selected from the group consisting of $C_{3-6}$cycloalkyl$C_{1-8}$alkyl, hydroxy$C_{1-8}$alkyl, —$(CH_2CH_2—O)_n$—$CH_3$, where n=1–4, alkoxy$C_{1-8}$alkyl and $C_{1-8}$alkyl optionally substituted with —O—C(O)$R^{12}$;
   $R^{12}$ is $C_{1-8}$alkyl, $C_{3-6}$cycloalkyl and $C_{6-14}$aryl;

or a pharmaceutically acceptable derivative thereof.

6. A compound of formula (IA) according to claim 1 wherein:
   $R^1$ is a substituent in the 3 or 5 position, or in both the 3 and 5 positions, independently selected from the group consisting of halogen, $C_{1-8}$alkyl, —$CF_3$ and —CN;
   $R^2$ is halogen;
   $R^3$ is $C_{1-8}$alkyl;
   $R^4$ is —$S(O)_2NR^5R^6$;
   $R^5$ is hydrogen;
   $R^6$ is selected from the group consisting of —$C(O)R^7$ and —$C(O)OR^7$;
   $R^7$ is $C_{1-8}$alkyl;

or a pharmaceutically acceptable derivative thereof.

7. A compound of formula (IA), according to claim 1, wherein
   $R^1$ is a substituent in both the 3 and 5 positions, independently selected from the group consisting of halogen, $C_{1-8}$alkyl, —$CF_3$ and —CN;
   $R^2$ is halogen;
   $R^3$ is $C_{1-8}$alkyl;
   $R^4$ is —$S(O)_2NR^5R^6$;
   $R^5$ is hydrogen;
   $R^6$ is selected from the group consisting of —$C(O)R^7$ and —$C(O)OR^7$;
   $R^7$ is $C_{1-8}$alkyl;

or a pharmaceutically acceptable derivative thereof.

8. A compound of formula (IA')

(IA')

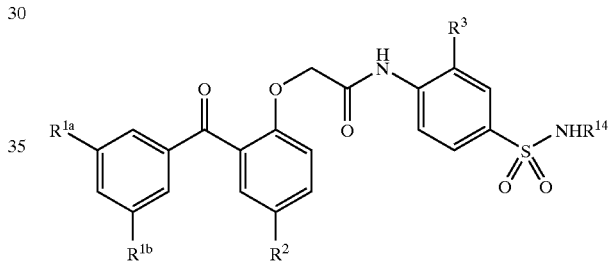

wherein, $R^{1a}$ and $R^{1b}$ are independently selected from the group consisting of hydrogen, halogen, $C_{1-8}$alkyl, —$CF_3$ and —CN;

$R^2$ is halogen;

$R^3$ is $C_{1-8}$alkyl;

$R^{14}$ is selected from the group consisting of

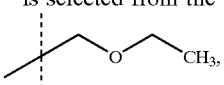

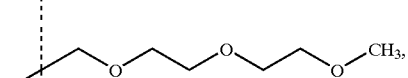

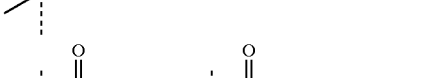

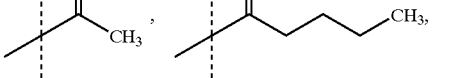

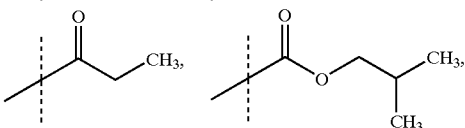

-continued

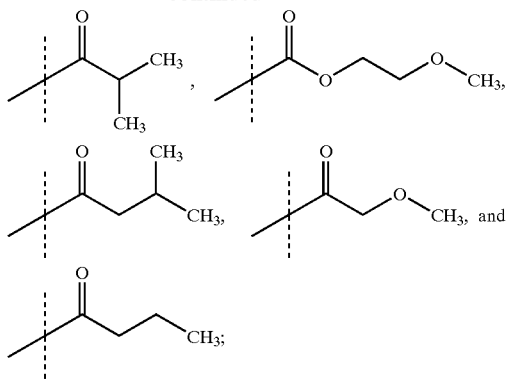

or a pharmaceutically acceptable derivative thereof;
provided that both $R^{1a}$ and $R^{1b}$ are not hydrogen.

9. A compound according to formula IA' according to claim 8 wherein $R^{1a}$ and $R^{1b}$ are independently selected from the group consisting of halogen, —$CF_3$ and —CN;

$R^2$ is halogen;
$R^3$ is $C_{1-8}$alkyl;
$R^{14}$ is selected from the group consisting of

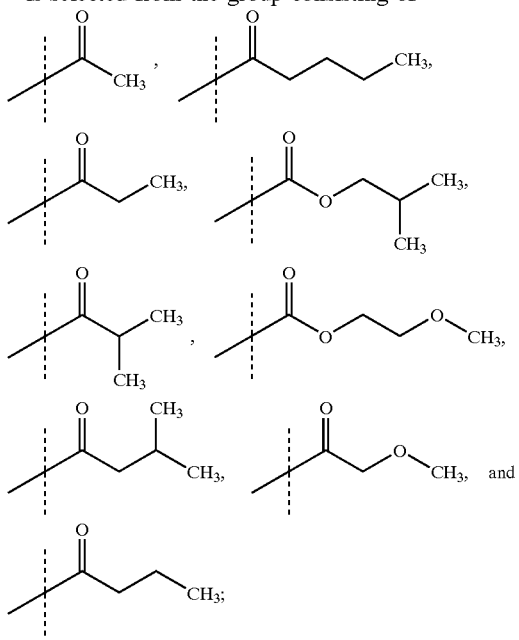

or a pharmaceutically acceptable derivative thereof.

10. A compound of formula (IB)

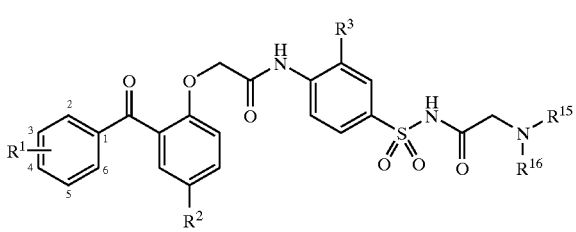

(IB)

wherein:

$R^1$ is one or more substituents independently selected from the group consisting of halogen, —$CF_3$, $C_{1-8}$alkyl, amino$C_{1-8}$alkyl, alkoxy, —CN, —$NO_2$, —$NH_2$, —$SR^8$, —$S(O)R^8$, $S(O)_2R^8$, —$C(O)R^8$; $C_{2-6}$alkenyl which may be optionally substituted with a substituent selected from the group consisting of hydroxy, halogen, $C_{6-14}$aryl, $C_{3-6}$cycloalkyl, $C_{6-14}$aryl and heterocycle; $C_{2-6}$alkynyl which may be optionally substituted with a substituent selected from the group consisting of hydroxy, halogen, $C_{3-6}$cycloalkyl, $C_{6-14}$aryl and heterocycle; and heterocycle, optionally substituted with one or more substituents selected from the group consisting of halogen, $C_{1-8}$alkyl, —CN, $C_{1-8}$alkyl$C_{6-14}$aryl and heterocycle;

$R^2$ is selected from the group consisting of hydrogen, halogen, $C_{1-8}$alkyl, —$NO_2$, —$NH_2$, $C_{1-8}$alkylamino, —$CF_3$ and alkoxy;

$R^3$ is selected from the group consisting of hydroxy, halogen, —$CF_3$, —$NO_2$ and $C_{1-8}$alkyl;

$R^8$ is selected from the group consisting of $C_{1-8}$alkyl, $C_{3-6}$cycloalkyl$C_{1-8}$alkyl, $C_{3-6}$cycloalkyl, $C_{6-14}$aryl and heterocycle;

$R^{15}$ and $R^{16}$ are independently selected from the group consisting of hydrogen, $C_{1-8}$alkyl, $C_{3-6}$cycloalkyl and $C_{6-14}$aryl, or $R^{15}$ and $R^{16}$ together with the atom to which they are attached form a ring, which optionally includes one or more heteroatoms selected from the group consisting of N, O and S, wherein N may be optionally substituted with a substituent selected from the group consisting of hydrogen, $C_{1-8}$alkyl and $C_{6-14}$aryl$C_{1-8}$alkyl;

or a pharmaceutically acceptable derivative thereof.

11. A compound of formula (IB) according to claim 8 wherein:

$R^1$ is a substituent in either the 3 or 5 position, or in both the 3 and 5 positions, independently selected from the group consisting of halogen, —$CF_3$, $C_{1-8}$alkyl, amino$C_{1-8}$alkyl, alkoxy, —CN, —$NO_2$, —$NH_2$, —$SR^8$, —$S(O)R^8$, —$S(O)_2R^8$, —$C(O)R^8$, $C_{2-6}$alkenyl which may be optionally substituted with a substituent selected from the group consisting of hydroxy, halogen, $C_{3-6}$cycloalkyl, $C_{6-14}$aryl and heterocycle; $C_{2-6}$alkynyl which may be optionally substituted with a substituent selected from the group consisting of hydroxy, halogen, $C_{6-14}$aryl, $C_{3-6}$cycloalkyl, and heterocycle; and heterocycle, optionally substituted with one or more substituents selected from the group consisting of halogen, $C_{1-8}$alkyl, —CN, $C_{1-8}$alkyl$C_{6-14}$aryl and heterocycle;

$R^2$ is selected from the group consisting of hydrogen, halogen, $C_{1-8}$alkyl, —$NO_2$, —$NH_2$, $C_{1-8}$alkylamino, —$CF_3$ and alkoxy;

$R^3$ is selected from the group consisting of hydroxy, halogen, —$CF_3$, —$NO_2$ and $C_{1-8}$alkyl;

$R^8$ is selected from the group consisting of $C_{1-8}$alkyl, $C_{3-6}$cycloalkyl$C_{1-8}$alkyl, $C_{3-6}$cycloalkyl, $C_{6-14}$aryl and heterocycle;

$R^{15}$ and $R^{16}$ are independently selected from the group consisting of hydrogen, $C_{1-8}$alkyl, $C_{3-6}$cycloalkyl and $C_{6-14}$aryl, or $R^{15}$ and $R^{16}$ together with the atom to which they are attached form a ring, which optionally includes one or more heteroatoms selected from the group consisting of N, O and S, wherein N may be optionally substituted with a substituent selected from the group consisting of hydrogen, $C_{1-8}$alkyl and $C_{6-14}$aryl$C_{1-8}$alkyl;

or a pharmaceutically acceptable derivative thereof.

12. A compound of formula (IB) according to claim 10 wherein:
- $R^1$ is a substituent in either the 3 or 5 position, or in both the 3 and 5 positions, selected from the group consisting of halogen, $C_{1-8}$alkyl, —$CF_3$ and —CN;
- $R^2$ is selected from the group consisting of halogen, $C_{1-8}$alkyl, —$NO_2$, —$CF_3$ and alkoxy;
- $R^3$ is $C_{1-8}$alkyl;
- $R^{15}$ and $R^{16}$ are independently selected from the group consisting of hydrogen, $C_{1-8}$alkyl, $C_{3-6}$cycloalkyl and $C_{6-14}$aryl, or $R^{15}$ and $R^{16}$ together with the atom to which they are attached form a ring, which optionally includes one or more heteroatoms selected from the group consisting of N, O and S, wherein N may be optionally substituted with a substituent selected from the group consisting of hydrogen, $C_{1-8}$alkyl and $C_{6-14}$aryl$C_{1-8}$alkyl;

or a pharmaceutically acceptable derivative thereof.

13. A compound according of formula (IB) according to claim 10 wherein:
- $R^1$ is a substituent in either the 3 or 5 position, or both the 3 and 5 positions, independently selected from the group consisting of halogen, $C_{1-8}$alkyl, —$CF_3$ and —CN;
- $R^2$ is halogen;
- $R^3$ is $C_{1-8}$alkyl;
- $R^{15}$ and $R^{16}$ are independently selected from the group consisting of $C_{1-8}$alkyl, $C_{3-6}$cycloalkyl and $C_{6-14}$aryl, or $R^{15}$ and $R^{16}$ together with the atom to which they are attached form a ring, which optionally includes one or more heteroatoms selected from the group consisting of N, O and S, wherein N may be optionally substituted with a substituent selected from the group consisting of hydrogen, $C_{1-8}$alkyl and $C_{6-14}$aryl$C_{1-8}$alkyl;

or a pharmaceutically acceptable derivative thereof.

14. A compound of formula (IB) according to claim 10 wherein:
- $R^1$ is a substituent in either the 3 or 5 position, or in both the 3 and 5 positions, independently selected from the group consisting of halogen, $C_{1-8}$alkyl, —$CF_3$ and —CN;
- $R^2$ is halogen;
- $R^3$ is $C_{1-8}$alkyl;
- $R^{15}$ and $R^{16}$ together with the atom to which they are attached form a ring, which optionally includes one or more heteroatoms selected from the group consisting of N, O and S, wherein N may be optionally substituted with a substituent selected from the group consisting of hydrogen, $C_{1-8}$alkyl and $C_{6-14}$aryl$C_{1-8}$alkyl;

or a pharmaceutically acceptable derivative thereof.

15. A compound selected from the group consisting of:
- N-{4-[(acetylamino)sulfonyl]-2-methylphenyl}-2-[4-chloro-2-(3-cyano-5-methylbenzoyl)phenoxy]acetamide;
- 2-[4-chloro-2-(3-cyano-5-methylbenzoyl)phenoxy]-N-{4-[(isobutyrylamino)sulfonyl]-2-methylphenyl}acetamide;
- 2-[4-chloro-2-(3-cyano-5-methylbenzoyl)phenoxy]-N-{2-methyl-4-[(propionylamino)sulfonyl]phenyl}acetamide;
- 2-[4-chloro-2-(3-cyano-5-methylbenzoyl)phenoxy]-N-(2-methyl-4-{[(1-pyrrolidinylacetyl)amino]sulfonyl}phenyl)acetamide;
- 2-[4-chloro-2-(3-cyano-5-methylbenzoyl)phenoxy]-N-(2-methyl-4-{[(1-piperidinylacetyl)amino]sulfonyl}phenyl)acetamide;
- 2-[4-chloro-2-(3-cyano-5-methylbenzoyl)phenoxy]-N-(2-methyl-4-{[(4-morpholinylacetyl)amino]sulfonyl}phenyl)acetamide;
- 2-{4-chloro-2-[3-cyano-5-(trifluoromethyl)benzoyl]phenoxy}-N-{2-methyl-4-[(propionylamino)sulfonyl]phenyl}acetamide;
- 2-{4-chloro-2-[3-cyano-5-(trifluoromethyl)benzoyl]phenoxy}-N-{4-[(isobutyrylamino)sulfonyl]-2-methylphenyl}acetamide;
- 2-{4-chloro-2-[3-cyano-5-(trifluoromethyl)benzoyl]phenoxy}-N-(2-methyl-4-{[(3-methylbutanoyl)amino]sulfonyl}phenyl)acetamide;
- 2-[4-chloro-2-(3-chloro-5-cyanobenzoyl)phenoxy]-N-{2-methyl-4-[(propionylamino)sulfonyl]phenyl}acetamide;
- 2-[4-chloro-2-(3-chloro-5-cyanobenzoyl)phenoxy]-N-{4-[(isobutyrylamino)sulfonyl]-2-methylphenyl}acetamide;
- 2-[4-chloro-2-(3-chloro-5-cyanobenzoyl)phenoxy]-N-(2-methyl-4-{[(3-methylbutanoyl)amino]sulfonyl}phenyl)acetamide;
- 2-[4-chloro-2-(3-chloro-5-cyanobenzoyl)phenoxy]-N-(2-methyl-4-{[(1-pyrrolidinylacetyl)amino]sulfonyl}phenyl)acetamide;
- N-{4-[(butyrylamino)sulfonyl]-2-methylphenyl}-2-[4-chloro-2-(3-chloro-5-cyanobenzoyl)phenoxy]acetamide;
- 2-[4-chloro-2-(3-chloro-5-cyanobenzoyl)phenoxy]-N-{2-methyl-4-[(pentanoylamino)sulfonyl]phenyl}acetamide;
- isobutyl {4-[({4-chloro-2-[3-cyano-5-(trifluoromethyl)benzoyl]phenoxy}acetyl)amino]-3-methylphenyl]sulfonylcarbamate;
- isobutyl [4-({[4-chloro-2-(3-chloro-5-cyanobenzoyl)phenoxy]acetyl}amino)-3-methylphenyl]sulfonylcarbamate;
- 2-methoxyethyl [4-({[4-chloro-2-(3-chloro-5-cyanobenzoyl)phenoxy]acetyl}amino)-3-methylphenyl]sulfonylcarbamate;
- 2-[4-chloro-2-(3-chloro-5-cyanobenzoyl)phenoxy]-N-(4-{[(methoxyacetyl)amino]sulfonyl}-2-methylphenyl)acetamide;
- 2-{4-chloro-2-[3-fluoro-5-(trifluoromethyl)benzoyl]phenoxy}-N-(4-{[(ethoxymethyl)amino]sulfonyl}-2-methylphenyl)acetamide;
- 2-{4-chloro-2-[3-fluoro-5-(trifluoromethyl)benzoyl]phenoxy}-N-{4-[({[2-(2-methoxyethoxy)ethoxy]methyl}amino)sulfonyl]-2-methylphenyl}acetamide;
- 2-{4-chloro-2-[3-fluoro-5-(trifluoromethyl)benzoyl]phenoxy}-N-(2-methyl-4-{[methyl(4-morpholinylacetyl)amino]sulfonyl}phenyl)acetamide;
- $N^1$-{[4-({[4-chloro-2-(3-chloro-5-cyanobenzoyl)phenoxy]acetyl}amino)-3-methylphenyl]sulfonyl}-L-isoleucinamide;
- $N^1$-{[4-({[4-chloro-2-(3-chloro-5-cyanobenzoyl)phenoxy]acetyl}amino)-3-methylphenyl]sulfonyl}valinamide;
- $N^1$-{[4-({[4-chloro-2-(3-chloro-5-cyanobenzoyl)phenoxy]acetyl}amino)-3-methylphenyl]sulfonyl}-L-leucinamide;
- $N^1$-{[4-({[4-chloro-2-(3-chloro-5-cyanobenzoyl)phenoxy]acetyl}amino)-3-methylphenyl]sulfonyl}-D-alaninamide;

N¹-{[4-({[4-chloro-2-(3-chloro-5-cyanobenzoyl)
  phenoxy]acetyl}amino)-3-methylphenyl]
  sulfonyl}glycinamide;
N-{4-[(acetylamino)sulfonyl]-2-methylphenyl}-2-[4-
  chloro-2-(3-chloro-5-cyanobenzoyl)phenoxy]
  acetamide;
N-{[4-({[4-chloro-2-(3-chloro-5-cyanobenzoyl)phenoxy]
  acetyl}amino)-3-methylphenyl]sulfonyl}-1-
  methylprolinamide;
2-[4-chloro-2-(3-chloro-5-cyanobenzoyl)phenoxy]-N-(4-
  {[isobutyryl(methyl)amino]sulfonyl}-2-methylphenyl)
  acetamide;
2-[4-chloro-2-(3-chloro-5-cyanobenzoyl)phenoxy]-N-(2-
  methyl-4-{[methyl(propionyl)amino]sulfonyl}phenyl)
  acetamide;
N-(4-{[acetyl(methyl)amino]sulfonyl}-2-methylphenyl)-
  2-[4-chloro-2-(3-chloro-5-cyanobenzoyl)phenoxy]
  acetamide;
2-[4-chloro-2-(3-chloro-5-cyanobenzoyl)phenoxy]-N-{4-
  [(hexanoylamino)sulfonyl]-2-
  methylphenyl}acetamide;
2-[4-chloro-2-(3-chloro-5-cyanobenzoyl)phenoxy]-N-{4-
  [(heptanoylamino)sulfonyl]-2-
  methylphenyl}acetamide;
2-[4-chloro-2-(3-chloro-5-cyanobenzoyl)phenoxy]-N-{2-
  methyl-4-[(octanoylamino)sulfonyl]
  phenyl}acetamide;
2-[4-chloro-2-(3-chloro-5-cyanobenzoyl)phenoxy]-N-{2-
  methyl-4-[(nonanoylamino)sulfonyl]
  phenyl}acetamide;
isopropyl [4-({[4-chloro-2-(3-chloro-5-cyanobenzoyl)
  phenoxy]acetyl}amino)-3-methylphenyl]
  sulfonylcarbamate;
ethyl [4-({[4-chloro-2-(3-chloro-5-cyanobenzoyl)
  phenoxy]acetyl}amino)-3-methylphenyl]
  sulfonylcarbamate;
methyl [4-({[4-chloro-2-(3-chloro-5-cyanobenzoyl)
  phenoxy]acetyl}amino)-3-methylphenyl]
  sulfonylcarbamate;
and pharmaceutically acceptable derivatives thereof.

16. A compound according to claim 1 wherein the pharmaceutically acceptable derivative is a salt.

17. A compound according to claim 16 wherein the salt is selected from the group consisting of sodium, calcium, potassium, magnesium, choline, ethanolamine, and triethylamine.

18. A compound selected from the group consisting of:
N-{4-[(acetylamino)sulfonyl]-2-methylphenyl}-2-[4-
  chloro-2-(3-cyano-5-methylbenzoyl)phenoxy]
  acetamide, sodium salt;
2-[4-chloro-2-(3-cyano-5-methylbenzoyl)phenoxy]-N-
  {4-[(isobutyrylamino)sulfonyl]-2-
  methylphenyl}acetamide, sodium salt;
2-[4-chloro-2-(3-cyano-5-methylbenzoyl)phenoxy]-N-
  {2-methyl-4-[(propionylamino)sulfonyl]
  phenyl}acetamide, sodium salt;
2-{4-chloro-2-[3-cyano-5-(trifluoromethyl)benzoyl]
  phenoxy}-N-{2-methyl-4-[(propionylamino)sulfonyl]
  phenyl}acetamide, sodium salt;
2-{4-chloro-2-[3-cyano-5-(trifluoromethyl)benzoyl]
  phenoxy}-N-{4-[(isobutyrylamino)sulfonyl]-2-
  methylphenyl}acetamide, sodium salt;
2-{4-chloro-2-[3-cyano-5-(trifluoromethyl)benzoyl]
  phenoxy}-N-(2-methyl-4-{[(3-methylbutanoyl)amino]
  sulfonyl}phenyl)acetamide, sodium salt;
2-[4-chloro-2-(3-chloro-5-cyanobenzoyl)phenoxy]-N-{2-
  methyl-4-[(propionylamino)sulfonyl]
  phenyl}acetamide, sodium salt;
2-[4-chloro-2-(3-chloro-5-cyanobenzoyl)phenoxy]-N-{2-
  methyl-4-[(propionylamino)sulfonyl]
  phenyl}acetamide, choline salt;
2-[4-chloro-2-(3-chloro-5-cyanobenzoyl)phenoxy]-N-{2-
  methyl-4-[(propionylamino)sulfonyl]
  phenyl}acetamide, ethanolamine salt;
2-[4-chloro-2-(3-chloro-5-cyanobenzoyl)phenoxy]-N-{4-
  [(isobutyrylamino)sulfonyl]-2-
  methylphenyl}acetamide, sodium salt;
2-[4-chloro-2-(3-chloro-5-cyanobenzoyl)phenoxy]-N-(2-
  methyl-4-{[(3-methylbutanoyl)amino]
  sulfonyl}phenyl)acetamide, sodium salt;
N-{4-[(butyrylamino)sulfonyl]-2-methylphenyl}-2-[4-
  chloro-2-(3-chloro-5-cyanobenzoyl)phenoxy]
  acetamide, sodium salt;
2-[4-chloro-2-(3-chloro-5-cyanobenzoyl)phenoxy]-N-{2-
  methyl-4-[(pentanoylamino)sulfonyl]
  phenyl}acetamide, sodium salt;
isobutyl {4-[({4-chloro-2-[3-cyano-5-(trifluoromethyl)
  benzoyl]phenoxy}acetyl)amino]-3-
  methylphenyl}sulfonylcarbamate, sodium salt;
isobutyl [4-({[4-chloro-2-(3-chloro-5-cyanobenzoyl)
  phenoxy]acetyl}amino)-3-methylphenyl]
  sulfonylcarbamate, sodium salt;
2-methoxyethyl [4-({[4-chloro-2-(3-chloro-5-
  cyanobenzoyl)phenoxy]acetyl}amino)-3-
  methylphenyl]sulfonylcarbamate, sodium salt;
2-[4-chloro-2-(3-chloro-5-cyanobenzoyl)phenoxy]-N-(4-
  {[(methoxyacetyl)amino]sulfonyl}-2-methylphenyl)
  acetamide, sodium salt;
N¹-{[4-({[4-chloro-2-(3-chloro-5-cyanobenzoyl)
  phenoxy]acetyl}amino)-3-methylphenyl]
  sulfonyl}glycinamide, sodium salt;
2-[4-chloro-2-(3-chloro-5-cyanobenzoyl)phenoxy]-N-(4-
  {[isobutyryl(methyl)amino]sulfonyl}-2-methylphenyl)
  acetamide;
2-[4-chloro-2-(3-chloro-5-cyanobenzoyl)phenoxy]-N-(2-
  methyl-4-{[methyl(propionyl)amino]sulfonyl}phenyl)
  acetamide;
N-(4-{[acetyl(methyl)amino]sulfonyl}-2-methylphenyl)-
  2-[4-chloro-2-(3-chloro-5-cyanobenzoyl)phenoxy]
  acetamide;
2-[4-chloro-2-(3-chloro-5-cyanobenzoyl)phenoxy]-N-{4-
  [(hexanoylamino)sulfonyl]-2-
  methylphenyl}acetamide, sodium salt;
2-[4-chloro-2-(3-chloro-5-cyanobenzoyl)phenoxy]-N-{4-
  [(heptanoylamino)sulfonyl]-2-
  methylphenyl}acetamide, sodium salt;
2-[4-chloro-2-(3-chloro-5-cyanobenzoyl)phenoxy]-N-{2-
  methyl-4-[(octanoylamino)sulfonyl]phenyl}acetamide,
  sodium salt;
2-[4-chloro-2-(3-chloro-5-cyanobenzoyl)phenoxy]-N-{2-
  methyl-4-[(nonanoylamino)sulfonyl]
  phenyl}acetamide, sodium salt;
isopropyl [4-({[4-chloro-2-(3-chloro-5-cyanobenzoyl)
  phenoxy]acetyl}amino)-3-methylphenyl]
  sulfonylcarbamate, sodium salt;
ethyl [4-({[4-chloro-2-(3-chloro-5-cyanobenzoyl)
  phenoxy]acetyl}amino)-3-methylphenyl]
  sulfonylcarbamate, sodium salt;

methyl [4-({[4-chloro-2-(3-chloro-5-cyanobenzoyl) phenoxy]acetyl}amino)-3-methylphenyl] sulfonylcarbamate, sodium salt;
and pharamceutically acceptable derivatives thereof.

19. Sodium, calcium, potassium, magnesium, choline, ethanolamine, and triethylamine salts of compounds selected from the group consisting of:

N-{4-[(acetylamino)sulfonyl]-2-methylphenyl}-2-[4-chloro-2-(3-cyano-5-methylbenzoyl)phenoxy] acetamide;

2-[4-chloro-2-(3-cyano-5-methylbenzoyl)phenoxy]-N-{4-[(isobutyrylamino)sulfonyl]-2-methylphenyl}acetamide;

2-[4-chloro-2-(3-cyano-5-methylbenzoyl)phenoxy]-N-{2-methyl-4-[(propionylamino)sulfonyl] phenyl}acetamide;

2-[4-chloro-2-(3-cyano-5-methylbenzoyl)phenoxy]-N-(2-methyl-4-{[(1-pyrrolidinylacetyl)amino] sulfonyl}phenyl)acetamide;

2-[4-chloro-2-(3-cyano-5-methylbenzoyl)phenoxy]-N-(2-methyl-4-{[(1-piperidinylacetyl)amino] sulfonyl}phenyl)acetamide;

2-[4-chloro-2-(3-cyano-5-methylbenzoyl)phenoxy]-N-(2-methyl-4-{[(4-morpholinylacetyl)amino] sulfonyl}phenyl)acetamide;

2-{4-chloro-2-[3-cyano-5-(trifluoromethyl)benzoyl] phenoxy}-N-{2-methyl-4-[(propionylamino)sulfonyl] phenyl}acetamide;

2-{4-chloro-2-[3-cyano-5-(trifluoromethyl)benzoyl] phenoxy}-N-{4-[(isobutyrylamino)sulfonyl]-2-methylphenyl}acetamide;

2-{4-chloro-2-[3-cyano-5-(trifluoromethyl)benzoyl] phenoxy}-N-{2-methyl-4-([(3-methylbutanoyl)amino] sulfonyl}phenyl)acetamide;

2-[4-chloro-2-(3-chloro-5-cyanobenzoyl)phenoxy]-N-{2-methyl-4-[(propionylamino)sulfonyl] phenyl}acetamide;

2-[4-chloro-2-(3-chloro-5-cyanobenzoyl)phenoxy]-N-{4-[(isobutyrylamino)sulfonyl]-2-methylphenyl}acetamide;

2-[4-chloro-2-(3-chloro-5-cyanobenzoyl)phenoxy]-N-(2-methyl-4-{[(3-methylbutanoyl)amino] sulfonyl}phenyl)acetamide;

2-[4-chloro-2-(3-chloro-5-cyanobenzoyl)phenoxy]-N-(2-methyl-4-{[(1-pyrrolidinylacetyl)amino] sulfonyl}phenyl)acetamide;

N-{4-[(butyrylamino)sulfonyl]-2-methylphenyl}-2-[4-chloro-2-(3-chloro-5-cyanobenzoyl)phenoxy] acetamide;

2-[4-chloro-2-(3-chloro-5-cyanobenzoyl)phenoxy]-N-{2-methyl-4-[(pentanoylamino)sulfonyl] phenyl}acetamide;

isobutyl {4-[({4-chloro-2-[3-cyano-5-(trifluoromethyl) benzoyl]phenoxy}acetyl)amino]-3-methylphenyl}sulfonylcarbamate;

isobutyl [4-({[4-chloro-2-(3-chloro-5-cyanobenzoyl) phenoxy]acetyl}amino)-3-methylphenyl] sulfonylcarbamate;

2-methoxyethyl [4-({[4-chloro-2-(3-chloro-5-cyanobenzoyl)phenoxy]acetyl}amino)-3-methylphenyl]sulfonylcarbamate;

2-[4-chloro-2-(3-chloro-5-cyanobenzoyl)phenoxy]-N-(4-{[(methoxyacetyl)amino]sulfonyl}-2-methylphenyl) acetamide;

2-{4-chloro-2-[3-fluoro-5-(trifluoromethyl)benzoyl] phenoxy}-N-(4-{[(ethoxymethyl)amino]sulfonyl}-2-methylphenyl)acetamide;

2-{4-chloro-2-[3-fluoro-5-(trifluoromethyl)benzoyl] pbenoxy}-N-{4-[({[2-(2-methoxyethoxy)ethoxy] methyl}amino)sulfonyl]-2-methylphenyl}acetamide;

2-{4-chloro-2-[3-fluoro-5-(trifluoromethyl)benzoyl] phenoxy}-N-(2-methyl-4-{[methyl(4-morpholinylacetyl)amino]sulfonyl}phenyl)acetamide;
and pharmaceutically acceptable derivatives thereof.

20. The sodium salt of a compound according to claim 15.

21. The choline salt of a compound according to claim 15.

22. A compound according to claim 1 in unsolvated form, solvated form, amorphous material, or mixtures of forms, solvates and amporphous material.

23. 2-[4-chloro-2-(3-chloro-5-cyanobenzoyl)phenoxy]-N-{2-methyl-4-[(propionylamino)sulfonyl] phenyl}acetamide sodium salt forms 1, 9, 10, or 12.

24. 2-[4-chloro-2-(3-chloro-5-cyanobenzoyl)phenoxy]-N-{2-methyl-4-[(propionylamino)sulfonyl] phenyl}acetamide choline salt forms 1, 2, 3, or 4.

25. 2-[4-chloro-2-(3-chloro-5-cyanobenzoyl)phenoxy]-N-{2-methyl-4-[(propionylamino)sulfonyl] phenyl}acetamide calcium salt forms 2 or 3.

26. A compound of formula (IA) according to claim 1 in the form of racemates, racemic mixtures, single enantiomers, diastereomeric mixtures and individual diastereoisomers.

27. A pharmaceutical composition comprising an effective amount of a compound according to claim 1 together with a pharmaceutically acceptable carrier.

28. A pharmaceutical composition according to claim 27 in the form of a tablet or capsule.

29. A pharmaceutical composition according to claim 27 in the form of a liquid.

30. A composition according to claim 27, wherein said composition comprises at least one additional therapeutic agent selected from the group consisting of (1-alpha, 2-beta, 3-alpha)-9-[2,3-bis(hydroxymethyl)cyclobutyl]guanine [(−) BHCG, SQ-34514, lobucavir], 9-[(2R,3R,4S)-3,4-bis (hydroxymethyl)-2-oxetanosyl]adenine (oxetanocin-G), TMC-114, BMS-232632, acyclic nucleosides [e.g. acyclovir, valaciclovir, famciclovir, ganciclovir, penciclovir), acyclic nucleoside phosphonates [e.g. (S)-1-(3-hydroxy-2-phosphonyl-methoxypropyl)cytosine (HPMPC), [[[2-(6-amino-9H-purin-9-yl)ethoxy]methyl] phosphinylidene]bis(oxymethylene)-2,2-dimethylpropanoic acid (bis-POM PMEA, adefovir dipivoxil), [[(1R)-2-(6-amino-9H-purin-9-yl)-1-methylethoxy]methyl]phosphonic acid (tenofovir), (R)-[[2-(6-Amino-9H-purin-9-yl)-1-methylethoxy]methyl]phosphonic acid bis-(isopropoxycarbonyloxymethyl)ester (bis-POC-PMPA)], ribonucleotide reductase inhibitors (e.g. 2-acetylpyridine 5-[(2-chloroanilino)thiocarbonyl) thiocarbonohydrazone and hydroxyurea), nucleoside reverse transcriptase inhibitors (e.g., 3'-azido-3'-deoxythymidine (AZT, zidovudine), 2',3'-dideoxycytidine (ddC, zalcitabine), 2',3'-dideoxyadenosine, 2',3'-dideoxyinosine (ddI, didanosine), 2',3'-didehydrothymidine (d4T, stavudine), (−)-beta-D-2,6-diaminopurine dioxolane (DAPD), 3'-Azido-2',3'-dideoxythymidine-5'-H-phosphophonate (phosphonovir), 2'-deoxy-5-iodo-uridine (idoxuridine), as (−)-cis-1-(2- hydroxymethyl)-1,3-oxathiolane 5-yl)-cytosine (lamivudine), or cis-1-(2-(hydroxymethyl)-1,3-oxathiolan-5-yl)-5-fluorocytosine (FTC), 3'-deoxy-3'-fluorothymidine, 5-chloro-2',3'-dideoxy-3'-fluorouridine, (−)-cis-4-[2-amino-6-(cyclopropylamino)-9H-purin-9-yl]-2-cyclopentene-1-methanol (abacavir), 9-[4-hydroxy-2-(hydroxymethyl)but-1-yl]-guanine (H2G), ABT-606 (2HM-H2G) and ribavirin), protease inhibitors (e.g. indinavir, ritonavir, nelfinavir, amprenavir, saquinavir, (R)-N-tert-butyl-3-[(2S,3S)-2-hydroxy-3-N-[(R)-2-N-(isoquinolin-5-yloxyacetyl)amino-3-methylthiopropanoyl]amino-4-phenylbutanoyl]-5,5-dimethyl-1,3-thiazolidine-4-carboxamide (KNI-272), 4R-(4alpha,5alpha,6beta)]-1,3-bis[(3-aminophenyl)methyl] hexahydro-5,6-dihydroxy-4,7-bis(phenylmethyl)-2H-1,3-diazepin-2-one dimethanesulfonate (mozenavir), 3-[1-[3-[2-(5-trifluoromethylpyridinyl)-sulfonylamino]phenyl] propyl]-4-hydroxy-6alpha-phenethyl-6beta-propyl-5,6-dihydro-2-pyranone (tipranavir), N'-[2(S)-Hydroxy-3(S)-[N-(methoxycarbonyl)-1-tert-leucylamino]-4-phenylbutyl-$N^{alpha}$-(methoxycarbonyl)-N'-[4-(2-pyridyl)benzyl]-L-tert-leucylhydrazide (BMS-232632), 3-(2(S)-Hydroxy-3(S)-(3-hydroxy-2-methylbenzamido)-4-phenylbutanoyl)-5,5-dimethyl-N-(2-methylbenzyl)thiazolidine-4(R)-carboxamide (AG-1776), N-(2(R)-Hydroxy-1(S)-indanyl)-2(R)-phenyl-methyl-4(S)-hydroxy-5-(1-(1-(4-benzo[b] furanylmethyl)-2(S)-N'-(tert-butylcarboxamido) piperazinyl)pentanamide (MK-944A), and GW 433908), interferons such as α-interferon, renal excretion inhibitors such as probenecid, nucleoside transport inhibitors such as dipyridamole; pentoxifylline, N-acetylcysteine (NAC), Procysteine, α-trichosanthin, phosphonoformic acid, as well as immunomodulators such as interleukin II or thymosin, granulocyte macrophage colony stimulating factors, erythropoietin, soluble $CD_4$ and genetically engineered derivatives thereof, non-nucleoside reverse transcriptase inhibitors (NNRTIs) for example, TMC-120, TMC-125, nevirapine (BI-RG-587), alpha-((2-acetyl-5-methylphenyl) amino)-2,6-dichloro-benzeneacetamide (loviride), 1-[3-(isopropylamino)-2-pyridyl]-4-[5-(methanesulfonamido)-1H-indol-2-ylcarbonyl]piperazine monomethanesulfonate (delavirdine), (10R, 11S, 12S)-12-Hydroxy-6,6,10,11-tetramethyl-4-propyl-11,12-dihydro-2H, 6H, 10H-benzo(1, 2-b:3,4-b':5,6-b")tripyran-2-one ((+) calanolide A), (4S)-6-Chloro-4-[1E)-cyclopropylethenyl)-3,4-dihydro-4-(trifluoromethyl)-2(1H)-quinazolinone (DPC-083), 1-(ethoxymethyl)-5-(1-methylethyl)-6-(phenylmethyl)-2,4 (1H,3H)-pyrimidinedione (MKC-442), 5-(3,5-dichlorophenyl)thio-4-isopropyl-1-(4-pyridyl)methyl-1H-imidazol-2-ylmethyl carbamate (capravirine), glycoprotein 120 antagonists [e.g. PRO-2000, PRO-542 and 1,4-bis[3-[(2, 4-dichlorophenyl)carbonylamino]-2-oxo-5,8-disodiumsulfanyl]naphthalyl-2,5-dimethoxyphenyl-1,4-dihydrazone (FP-21399)], cytokine antagonists [e.g. reticulose (Product-R), 1,1'-azobis-formamide (ADA), and 1,11-(1,4-phenylenebis(methylene))bis-1,4,8,11-tetraazacyclotetradecane octahydrochloride (AMD-3100)], and fusion inhibitors for example T-20 and T-124.

31. A process for the preparation of compounds of formula (IA)

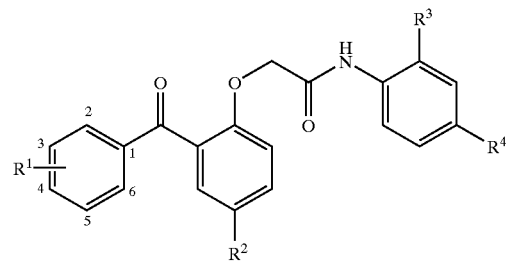

(IA)

wherein:

$R^1$ is one or more substituents independently selected from the group consisting of halogen, —$CF_3$, $C_{1-8}$alkyl, amino$C_{1-8}$alkyl, alkoxy, —CN, —$NO_2$, —$NH_2$, —$SR^8$, —$S(O)R^8$, —$S(O)_2R^8$, $C(O)R^8$; $C_{2-6}$alkenyl which may be optionally substituted with a substituent selected from the group consisting of hydroxy, halogen, $C_{3-6}$cycloalkyl, $C_{6-14}$aryl and heterocycle; $C_{2-6}$alkynyl which may be optionally substituted with a substituent selected from the group consisting of hydroxy, halogen, $C_{6-14}$aryl, $C_{3-6}$cycloalkyl, and heterocycle; and heterocycle, optionally substituted with one or more substituents selected from the group consisting of halogen, $C_{1-8}$alkyl, —CN, $C_{1-8}$alkyl$C_{6-4}$aryl and heterocycle;

$R^2$ is selected from the group consisting of hydrogen, halogen, $C_{1-8}$alkyl, —$NO_2$, —$NH_2$, $C_{1-8}$alkylamino, —$CF_3$ and alkoxy;

$R^3$ is selected from the group consisting of hydroxy, halogen, —$CF_3$, —$NO_2$ and $C_{1-8}$alkyl;

$R^4$ is selected from the group consisting of —$S(O)_2NR^5R^6$, —$S(O)_2N=C(OR^7)_2$ and —$S(O)_2N=CR^7(OR^7)$;

$R^5$ is selected from the group consisting of hydrogen, $C_{6-14}$aryl, $C_{1-8}$alkyl, $C_{3-6}$cycloalkyl$C_{1-8}$alkyl and $C_{3-6}$cycloalkyl;

$R^6$ is selected from the group consisting of —$C(O)R^7$, —$C(O)OR^7$, —$C(O)C(O)OR^7$, —$C(O)CH(NR^{12}R^{13})$ $R^{11}$, alkoxy$C_{1-8}$alkyl and —$CH_2O$—$(CH_2CH_2O)_n$—$CH_2CH_2OCH_3$, wherein n is 0-4;

$R^7$ is selected from the group consisting of $C_{3-6}$cycloalkyl$C_{1-8}$alkyl, hydroxy$C_{1-8}$alkyl, $C_{6-14}$aryl, heterocycle optionally substituted with $C_{1-8}$alkyl, $C_{6-14}$aryl$C_{1-8}$alkyl, —$(CH_2CH_2$—O$)_n$—$CH_3$, where n=1–4, alkoxy$C_{1-8}$alkyl and $C_{1-8}$alkyl optionally substituted with —O—$C(O)R^{12}$;

$R^8$ is selected from the group consisting of $C_{1-8}$alkyl, $C_{3-6}$cycloalkyl$C_{1-8}$alkyl, $C_{3-6}$cycloalkyl, $C_{6-14}$aryl and heterocycle;

$R^{11}$ is selected from the group consisting of hydrogen,

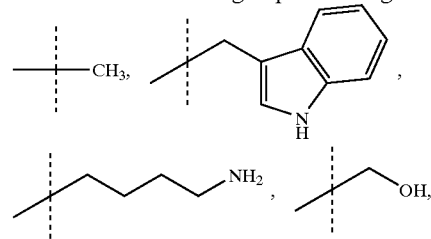

-continued

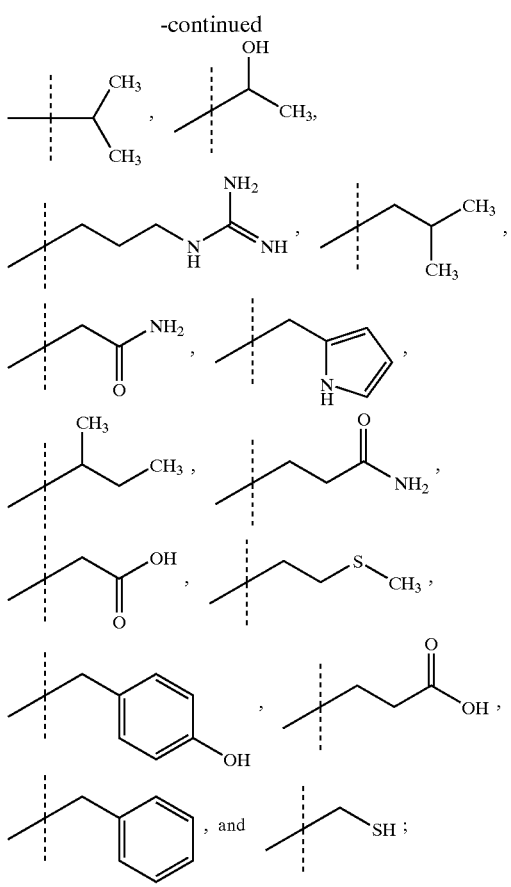

$R^{12}$ and $R^{13}$ are independently selected from the group consisting of hydrogen, $C_{1-8}$alkyl, $C_{3-6}$cycloalkyl and $C_{6-14}$aryl;

comprising coupling compounds of formula (II) and (III)

(II)

(III)

wherein $R^1$, $R^2$, $R^3$ and $R^4$ are herein defined.

32. A compound of formula (IA') according to claim 8 in the form of racemates, racemic mixtures, single enantiomers, diastereomeric mixtures and individual diastereoisomers.

33. A compound of formula (IB) according to claim 10 in the form of racemates, racemic mixtures, single enantiomers, diastereomeric mixtures and individual diastereoisomers.

* * * * *

UNITED STATES PATENT AND TRADEMARK OFFICE
CERTIFICATE OF CORRECTION

PATENT NO.         : 6,995,283 B2                                          Page 1 of 1
APPLICATION NO. : 10/469104
DATED              : February 7, 2006
INVENTOR(S)        : Joseph Howing Chan It is certified that error appears in the above-identified patent and that said Letters Patent is hereby corrected as shown below:

<u>On the Title Page, Item (57)</u>
Line 1 of the Abstract:
    "beazophenone" should read
    -- benzophenone --

Column 106, line 36, Claim 2:
    "$C_{6-4}arylC_{1-8}alky$" should read
    -- $C_{6-14}arylC_{1-8}alkyl$ --

Signed and Sealed this

Sixteenth Day of September, 2008

JON W. DUDAS
*Director of the United States Patent and Trademark Office*